United States Patent [19]
Inglis et al.

[11] Patent Number: 5,837,261
[45] Date of Patent: *Nov. 17, 1998

[54] VIRAL VACCINES

[75] Inventors: Stephen Charles Inglis, Linton; Michael Edward Griffith Boursnell, Cambridge; Anthony Charles Minson, Great Shelford, all of United Kingdom

[73] Assignee: Cantab Pharmaceuticals Research Limited, United Kingdom

[*] Notice: The term of this patent shall not extend beyond the expiration date of Pat. No. 5,665,362.

[21] Appl. No.: 216,260

[22] Filed: Mar. 21, 1994

Related U.S. Application Data

[63] Continuation-in-part of Ser. No. 30,073, May 20, 1993, abandoned, and a continuation-in-part of Ser. No. 168,643, Dec. 16, 1993, abandoned.

[30] Foreign Application Priority Data

| Sep. 25, 1990 | [GB] | United Kingdom | 9020799 |
| Mar. 8, 1991 | [GB] | United Kingdom | 9104903 |
| Dec. 16, 1992 | [GB] | United Kingdom | 9226172 |
| Mar. 19, 1993 | [GB] | United Kingdom | 9305710 |
| Dec. 6, 1993 | [GB] | United Kingdom | 9324964 |

[51] Int. Cl.$^6$ .......................... A61K 39/245; C12N 7/04; C12N 15/00
[52] U.S. Cl. .................... 424/229.1; 424/231.1; 435/235.1; 435/236; 435/172.3; 935/65
[58] Field of Search ............... 424/204.1, 229.1, 424/231.1; 435/235.1, 236, 172.3; 935/65

[56] References Cited

U.S. PATENT DOCUMENTS 5,166,057  11/1992  Palese et al. ........................ 435/69.1

FOREIGN PATENT DOCUMENTS

| 0213894 | 3/1987 | European Pat. Off. | A61K 39/12 |
| 0386882 | 9/1990 | European Pat. Off. | C12N 15/86 |
| 0453242 | 10/1991 | European Pat. Off. | A61K 48/00 |
| WO 8909271 | 10/1989 | WIPO | C12N 15/00 |
| WO 9005538 | 5/1990 | WIPO | A61K 39/00 |
| WO 9010693 | 9/1990 | WIPO | |
| WO 9105055 | 4/1991 | WIPO | C12N 15/86 |
| 9205263 | 4/1992 | WIPO | C12N 15/86 |
| WO 9403207 | 2/1994 | WIPO | |

OTHER PUBLICATIONS

Farrell, H.E., et al., "Vaccine Potential of a Herpes Simplex Virus Type 1 Mutant with an Essential Glycoprotein Deleted", *Journal of Virology*, 68(2):927–932 (1994).

Morrison, L.A., et al., "Immunization with Replication-Defective Mutants of Herpes Simplex Virus Type 1: Sites of Immune Intervention in Pathogenesis of Challenge Virus Infection", *Journal of Virology*, 68(2):689–696 (1994).

Peeters, B., et al., "Non–transmissible pseudorabies virus gp50 mutants a new generation of safe live vaccines", *Vaccine*, 12(4):375–380 (1994).

(List continued on next page.)

*Primary Examiner*—Mary E. Mosher
*Attorney, Agent, or Firm*—Walter H. Dreger; Robin M. Silva

[57] ABSTRACT

The application provides a pharmaceutical which comprises a mutant non-retroviral virus (particularly HSV-1 and/or HSV-2) whose genome is defective in respect of a gene essential for the production of infectious virus. The virus can infect normal cells and undergo replication and expression of viral antigen genes in those cells but cannot produce normal infectious virus. The pharmaceutical is for prophylactic or therapeutic use in generating an immune response in a subject infected therewith. Where the non-retroviral virus is a herpes simplex virus eg HSV-1 or HSV-2, the defect can be in the glycoprotein gH gene. Vaccines and therapeutic pharmaceuticals are provided especially for epithelial, oral, vaginal and nasal administration. Also provided is use of a mutant based on HSV-1 for the preparation of a pharmaceutical for prophylactic or therapeutic use in generating an immune response in a subject against type-2 HSV infection.

41 Claims, 33 Drawing Sheets

OTHER PUBLICATIONS

Nguyen, L.H., et al., "Replication–Defective Mutants of Herpes Simplex Virus (HSV) Induce Cellular Immunity and Protect against Lethal HSV Infection", *Journal of Virology*, 66(12):7067–7072 (1992).

Graham, F.L., et al., "Characteristics of a Human Cell Line Transformed by DNA from Human Adenovirus Type 5", *J. gen. Virol.*, 36:59–72 (1977).

Harrison, T., et al., "Host–Range Mutants of Adenovirus Type 5 Defective for Growth in HeLa Cells", *Virology*, 77:319–329 (1977).

Gluzman, Y., "SV40–Transformed Simian Cells Support the Replication of Early SV40 Mutants", *Cell*, 23:175–182 (1981).

Cai, W., et al., "Linker–Insertion Nonsense and Restriction–Site Deletion Mutations of the gB Glycoprotein Gene of Herpes Simplex Virus Type 1", *Journal of Virology*, 61(3):714–721 (1987).

Ligas, M.W., et al., "A Herpes Simplex Virus Mutant in which Glycoprotein D Sequences are Replaced by β–Galactosidase Sequences Binds to but is Unable to Penetrate into Cells", *Journal of Virology*, 62(5):1486–1494 (1988).

Fuller, A.O., et al., "Neutralizing Antibodies Specific for Glycoprotein H of Herpes Simplex Virus Permit Viral Attachment to Cells but Prevents Penetration", *Journal of Virology*, 63(8):3435–3443 (1989).

DeLuca, N.A., et al., "Isolation and Characterization of Deletion Mutants of Herpes Simplex Virus Type 1 in the Gene Encoding Immediate–Early Regulatory Protein ICP4", *Journal of Virology*, 56(2):558–570 (1985).

Johnson, D.C., et al., "Herpes Simplex Viruses Lacking Glycoprotein D are Unable to Inhibit Virus Penetration: Quantitative Evidence for Virus–Specific Cell Surface Receptors", *Journal of Virology*, 62(12):4605–4612 (1988).

Desai, P.J., et al., "Excretion of Non–infectious Virus Particles lacking Glycoprotein H by a Temperature–sensitive Mutant of Herpes Simplex Virus Type 1: Evidence that gH is Essential for Virion Infectivity", *J. gen. Virol.*, 69:1147–1156 (1988).

Racaniello, V.R., et al., "Cloned Poliovirus Complementary DNA is Infectious in Mammalian Cells", *Science*, 214:916–918 (1981).

Luytjes, W., et al., "Amplification, Expression, and Packaging of a Foreign Gene by Influenza Virus", *Cell*, 59:1107–1113 (1989).

Buller, R.M.L., et al., "Deletion of the Vaccinia Virus Growth Factor Gene Reduces Virus Virulence", *Journal of Virology*, 62(3):866–874 (1988).

Eliot, M., et al., "Construction of a defective adenovirus vector expressing the pseudorabies virus glycoprotein gp50 and its use as a live vaccine", *Journal of General Virology*, 71:2425–2431 (1990).

Forrester, A., et al., "Construction and Properties of a Mutant of Herpes Simplex Virus Type 1 with Glycoprotein H Coding Sequence Deleted", *Journal of Virology*, 66(1):341–348 (1992).

Ragot, T., et al., "Replication–defective recombinant adenovirus expressing the Epstein–Barr virus (EBV) envelope glycoprotein gp340/220 induces protective immunity against EBV–induced lymphomas in the cottontop tamarin", *Journal of General Virology*, 74:501–507 (1993).

Emi, N., et al., "Pseudotype Formation of Murine Leukemia Virus with the G Protein of Vesicular Stomatitis Virus", *Journal of Virology*, 65(3):1202–1207 (1991).

Dion, Michel, et al., "Isolation and Preliminary Characterization of Temperature–Sensitive Mutants of Human Cytomegalovirus." *Virology*, 158:228–230 (1987).

McGeoch, Duncan J., "The Genomes of the Human Herpes Viruses: Contents, Relationships and Evolution." *Annu. Rev. Microbiol.*, 43:235–265 (1989).

Ensinger, Marcia J., et al., "Fine Structure Marker Rescue of Temperature–Sensitive Mutations of Vaccinia Virus within a Central Conserved Region of the Genome." *Journal of Virology*, 56(3):1027–1029 (1985).

Frost, Eric and Jim Williams, "Mapping Temperature–Sensitive and Host–Range Mutations of Adenovirus Type 5 by Marker Rescue." *Virology*, 91:39–50 (1978).

Goebel, Scott J., et al. "The Complete DNA Sequence of Vaccinia Virus." *Virology*, 179:247–266 (1990).

Almond, J.W., et al., "Temperature–Sensitive Mutant of Fowl Plague Virus: Isolation and Genetic Characterization." *Virology*, 92:416–427 (1979).

Straus, Stephen E., et al., "Placebo–Controlled Trial of Vaccination with Recombinant Glycoprotein D of Herpes Simplex Virus Type 2 for Immunotherapy of Genital Herpes." *The Lancet*, 343:1460–1463 (1994).

McGeoch, Duncan J., and Andrew J. Davison, "DNA Sequence of the Herpes Simplex Virus Type I Gene Encoding Glycoprotein gH, and Identification of Homologues in the Genomes of Varicella–Zoster Virus and Epstein–Barr Virus." *Nucleic Acids Research*, 14(10):4281–4292 (1986).

Gao, Min and David M. Knipe, "Genetic Evidence for Multiple Nuclear Functions of the Herpes Simplex Virus ICP8 DNA–Binding Protein." *Journal of Virology*, 63(12):5258–5267 (1989).

McCarthy, Alice M., et al., "Herpes Simples Virus Type 1 ICP27 Deletion Mutants Exhibit altered Patterns of Transcription and Are DNA Deficient." *Journal of Virology*, 63(1):18–27(1989).

Ross, L.J.N., et al., "Nucleotide Sequence and Characterization of the Marek's Disease Virus Homologue of Glycoprotein B of Herpes Simplex Virus." *J. Gen. Virol.*, 70:1789–1804 (1989).

Whitebeck, J. Charles, et al., "Comparison of the Bovine Herpesvirus 1 gI Gene and the Herpes Simplex Virus Type 1 gB Gene." *Journal of Virology*, 62(9):3319–3327 (1988).

Hammerschmidt, Wolfgang, et al., "Conservation of a Gene Cluster Including Glycoprotein B in Bovine Herpesvirus Type 2 (BHV–2) and Herpes Simplex Virus Type 1 (HSV–1)." *Virology*, 165:388–405 (1988).

Chen, Katherine C., et al., "Complete Nucleotide Sequence and Genome Organization of Bovine Parvovirus." *Journal of Virology*, 60(3):1085–1097 (1986).

Cotmore, Susan F., "Identification of the Major Structural and Nonstructural Proteins Encoded by Human Parvovirus B19 and Mapping of Their Genes by Procaryotic Expression of Isolated Genomic Fragments." *Journal of Virology*, 60(2):548–557 (1986).

Mester, Joseph C. and Barry T. Rouse, "The Mouse Model and Understanding Immunity to Herpes Simplex Virus." *Reviews of Infectious Diseases*, 13:S935–S945 (1991).

Long, D., et al., "Glycoprotein D Protects Mice Against Lethal Challenge with Herpes Simplex Virus Types 1 and 2." *Infection and Immunity*, 43:761–764 (1984).

Straus, Stephen E., et al., "Induction and Enhancement of Immune Response to Herpes Simplex Virus Type 2 in Human by Use of a Recombinant Glycoprotein D Vaccine." *The Journal of Infectious Diseases*, 167:1045–1052 (1993).

Pachl, Carol, et al., "Expression of Cell–Associated and Secreted Forms of Herpes Simplex Virus Type 1 Glycoprotein gB in Mammalian Cells." *Journal of Virology*, 61(2):315–325 (1987).

Ghiasi, Homayon, et al., "Expression of Seven Herpes Simplex Virus Type 1 Glycoproteins (gB, gC, gD, gE, gG, gH, and gI): Comparative Protection against Lethal Challenge in Mice." *Journal of Virology*, 68(4):2118–2126 (1994).

Garcia, Nancy, "Vaccine Reduces Herpes Outbreaks." *BioWorld Today*, 4(86):1–4 (1993).

Stanberry, Lawrence R., et al., "Genital Herpes in Guinea Pigs: Pathogenesis of the Primary Infection and Description of Recurrent Disease." *The Journal of Infectios Diseases*, 146(3):397–404 (1982).

Cranage, Martin P., et al., "Identification and Expression of a Human Cytomegalovirus Glycoprotein with Homology to the Epstein–Barr Virus BXLF2 Product, varicella–Zoster Virus gpIII, and Herpes Simplex Virus Type 1 Glycoprotein H." *Journal of Virology*, 62(4):1416–1422 (1988).

Thomas, G. Paul and Michael B. Mathews, "DNA Replication and the Early to Late Transition in Adenovirus Infection." *Cell*, 22:523–533 (1980).

Fiers, W., et al., "Complete Nucleotide Sequence of SV40 DNA." *Nature*, 273:113–120 (1978).

Somogyi, Pal, et al., "Fowlpox Virus Host Range Restriction: Gene Expression, DNA Replication, and Morphogenesis in Nonpermissive Mammalian Cells." *Virology*, 197:439–444 (1993).

Tashiro, Masato, et al., "Cell–Mediated Immunity Induced in Mice after Vaccination with a Protease Activation Mutant, TR–2, of Sendai Virus." *Journal of Virology*, 62:2490–2497 (1988).

Beatrice, Sara T., and Robert R. Wagner, "Immunogenicity in Mice of Temperature–sensitive Mutants of Vesicular Stomatitis Virus: Early Appearance in Bronchial Secretions of an Interferon–like Inhibitor." *J. Gen. Virol.*, 47:529–533 (1980).

Perkus, Marion E., et al. "Vaccinia Virus Host Range Genes." *Virology*, 179:276–286 (1990).

McLaren, Leroy C., and John J. Holland, "Defective Interfering Particles from Poliovirus Vaccine and Vaccine Reference Strains." *Virology*, 60:579–583 (1974).

Konishi, Eiji, et al., "A Highly Attenuated Host Range–Restricted Vaccinia Virus Strain, NYVAC, Encoding the prM, E and NS1 Genes of Japanese Encephalitis Virus Prevents JEV Viremia in Swine." *Virology*, 190:454–458 (1992).

Tartaglia, James, et al., "NYVAC: A Highly Attenuated Strain of Vaccinia Virus." *Virology*, 188:217–232 (1992).

Alkhatib et al., "High–Level Eucaryotic In Vivo Expression of Biologically Active Measles Virus Hemagglutinin by Using an Adenovirus Type 5 Helper–Free Vector System," *Journal of Virology*, 62(8):2718–2727 (1988).

Akrigg, A., et al., "The Structure of the Major Immediate Early Gene of Human Cytomegalovirus Strain AD169," *Virus Research*, 2:107–121 (1985).

Brierly, I., et al., "Characterization of an Efficient Coronavirus Ribosomal Frameshifting Signal: Requirement for an RNA Pseudoknot," *Cell*, 57–537–547 (1989).

Chakrabarti, L., et al., "Sequence of Simian Immunodeficiency Virus from Macaque and Its Relationship to Other Human and Simian Retroviruses," *Nature*, 328(6):543–547 (1987).

Chakrabarti, S., et al., "Vaccinia Virus Expression Vector: Coexpression of β–Galactosidase Provides Visual Screening and Recombinant Virus Plaques," *Molecular and Cellular Biology*, 5(12):3403–3409 (1985).

Everett, R.D., et al., "DNA Sequence Elements Required for Regulated Expression of the HSV–1 Glycoprotein D Gene Lie within 83 bp of the RNA Capsites," *Nucleic Acids Research*, 11(19):6647–6666 (1983).

Gompels, U.A., et al., "Antigenic Properties and Cellular Localization of Herpes Simplex Virus Glycoprotein H Synthesized in a Mammalian Cell Expression System." *Journal of Virology*, 63(11):4744–4755 (1989).

Graham, F.L., et al., "A New Technique for the Assay of Infectivity of Human Adenovirus 5 DNA," *Virology*, 52:456–467 (1973).

Krieg, P.A., et al., "Functional Messenger RNAs are Produced by SP6 in vitro Transcription of Cloned cDNAs," *Nucleic Acids Research*, 12(18):7057–7070 (1984).

McGeoch, D.J., et al., "The Complete DNA Sequence of the Long Unique Region in the Genome of Herpes Simplex Virus Type 1," *J. Gen. Virol.*, 69:1531–1574 (1988).

Twigg, A.J., et al., "Trans–Complementable Copy–Number Mutants of Plasmid ColE1," *Nature*, 283:216–218 (1980).

Vieira, J., et al., "[1] Production of Single–Stranded Plasmid DNA," *Methods in Enzymology*, 153:3–11 (1987).

Hill, T.J., et al., "Acute and Recurrent Infection with Herpes Simplex Virus in The Mouse: A Model for Studying Latency and Recurrent Disease," *J. Gen. Virol.*, 28:341–353 (1975).

Gallichan, W.S., et al., "Mucosal Immunity and Protection after Intranasal Immunization with Recombinant Adenovirus Expressing Herpes Simplex Virus Glycoprotein B," *The Journal of Infectious Diseases*, 168:622–629 (1993).

Stanberry, L.R., et al., "Herpes Simplex Virus Glycoprotein Treatment of Recurrent Genital Herpes," *The Journal of Infectious Diseases*, 157(1):756–163 (1988).

Stanberry, L.R., et al., "Preinfection Prophylaxis with Herpes Simplex Virus Glycoprotein Immunogens: Factor Influencing Efficacy," *J. Gen. Virol.*, 70:3177–3185 (1989).

Baer, R., et al., "DNA Sequence and Expression of the B95–8 Epstein–Barr Virus Genome," *Nature*, 310:207–211 (1984).

Killington, R.A., et al., "Growth, Assay and Purification of Herpesviruses," *Techniques in Virology*, 207–236 (1994).

Peeters, B. et al. 1992. Journal of Virology, vol. 66, pp. 894–905.

Rauh, I. et al. 1991. Journal of Virology, vol. 65, pp. 5384–5356.

Moss, B. 1985. *Virology*. Ed. B. N. Fields et al, Raven press, N.Y., pp. 685–703.

Miner, J.N. et al. 1990. Virus Genes, vol. 3:4, pp. 355–359.

Ballay, A. et al. EMBO journal, vol. 4, No. 13B, pp. 3861–3865, 1985.

Fig. 12a
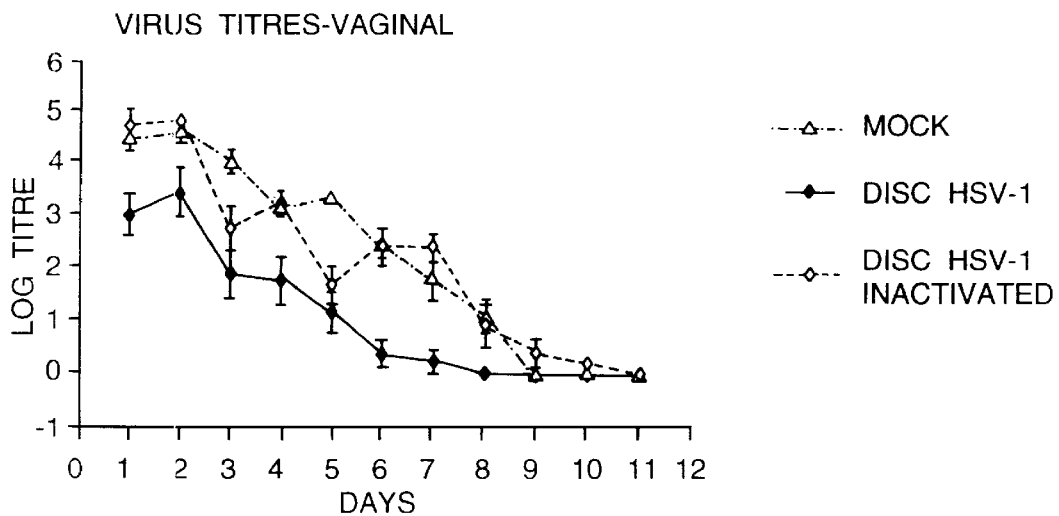
Fig. 12b
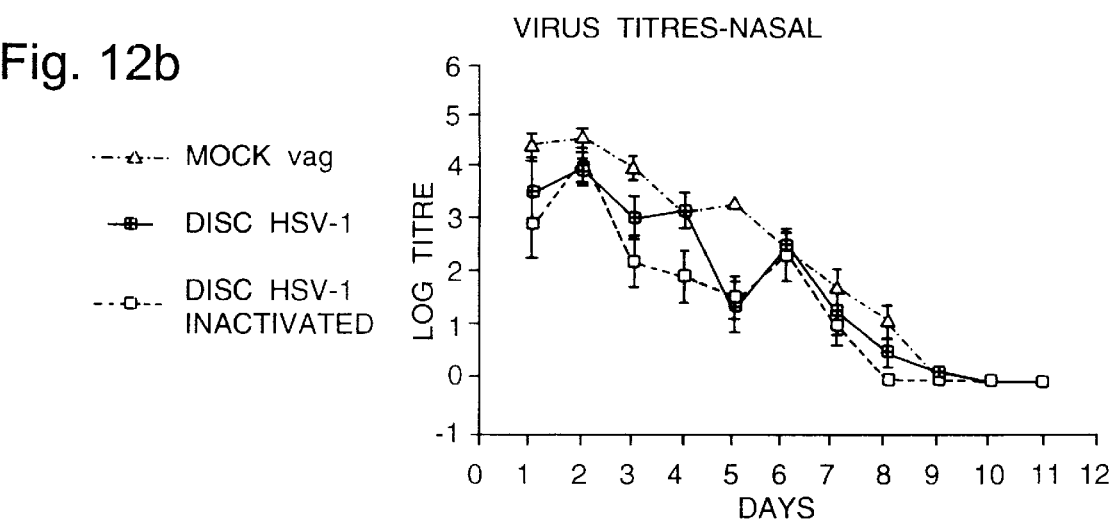
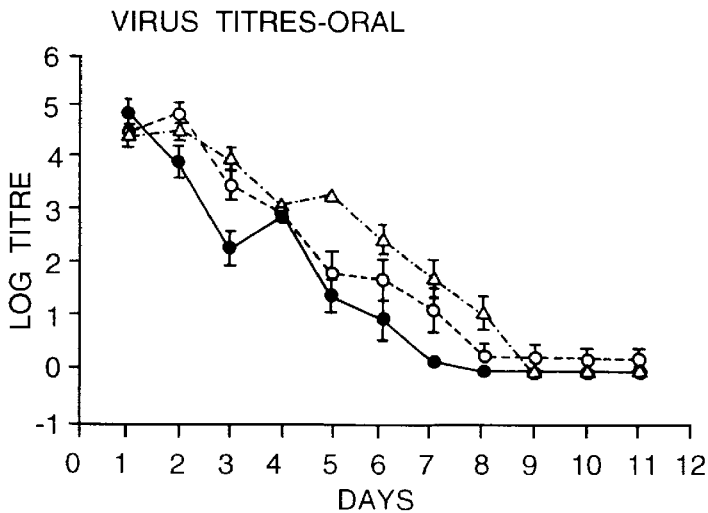
Fig. 12c
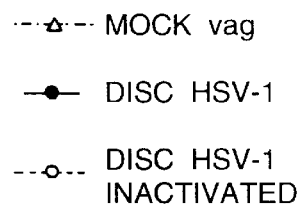

Fig. 18

| | |
|---|---|
| CTGCAGCGCGGCGGGAGGTGGCGGGAGGACTGGGGCCGGCTGACGGGGGTCGCCGCGGCG | 60 |
| ACCCCGCGCCCCGACCCCGAGGACGGCGCGGGGTCTCTGCCCCGCATCGAGGACACGCTG | 120 |
| TTTGCCCTGTTCCGCGTTCCCGAGCTGCTGGCCCCAACGGGGACTTGTACCACATTTTT | 180 |
| GCCTGGGTCTTGGACGTCTTGGCCGACCGCCTCCTTCCGATGCATCTATTTGTCCTGGAT | 240 |
| TACGATCAGTCGCCCGTCGGGTGTCGAGACGCCCTGTTGCGCCTCACCGCCGGGATGATC | 300 |
| CCAACCCGCGTCACAACCGCCGGGTCCATCGCCGAGATACGCGACCTGGCGCGCACGTTT | 360 |
| GCCCGCGAGGTGGGGGGAGTTTAGTTCAAACACGGAAGCCCGAACGGAAGGCCTCCCGGC | 420 |
| GATGACGGCAATAAAAGAACAGAATAAAAGGCATTGTTGTCGTGTGGTGTGTCCATAAGC | 480 |
| GCGGGGGTTCGGGGCCAGGGCTGGCACCGTATCAGCACCCCACCGAAAAACGGAGCGGGC | 540 |
| CGATCCGTCCTTGTTTTCGGTCTGGTACTCCCTTTGTGCTTTTACCCTCACCCCACCCCA | 600 |
| TCCTTTGGCCCGCGCTTACGGCAACAAAGGGCCTCCGATAGCCTCCGAGGTGCGGACGCT | 660 |
| CTTTGGGCCGTGGGTACGGACACCCCCCATCTGCGGACTGGCAGCCGGGACGACGACCA | 720 |
|                                                                                                            M | |
| TGGGCCCCGGTCTGTGGGTGGTGATGGGGGTCCTGGTGGNCGTTGCCGGGGGCCATGACA | 780 |
|  G  P  G  L  W  V  V  M  G  V  L  V  V  V  A  G  H  D  T | |
| CGTACTGGACGGAGCAAATCGACCCGTGGTTTTTGCACGGTCTGGGGTTGGCCCGCACGT | 840 |
|  Y  W  T  E  Q  I  D  P  W  F  L  H  G  L  G  L  A  R  T  Y | |
| ACTGGCGCGACACAAACACCGGGCGTCTGTGGTTGCCCAACACCCCCGACGACCAGCGAC | 900 |
|  W  R  D  T  N  T  G  R  L  W  L  P  N  T  P  D  D  Q  R  P | |
| CCCCAGCGCGGACGCTTGGCGCCCCGGGCAACTCAACCTGACTACGGCATCCGTGCCCA | 960 |
|  P  A  R  T  L  G  A  P  G  Q  L  N  L  T  T  A  S  V  P  M | |
| TGCTTCGGTGGTACGCCGAGCGCTTTTGTTTCGTGTTGGTCACCACGGCCGAGTTTCCTC | 1020 |
|  L  R  W  Y  A  E  R  F  C  F  V  L  V  T  T  A  E  F  P  R | |
| GGGACCCCGGGCAGCTGCTTTACATCCCAAAGACCTATCTGCTCGGCCGGCCTCGGAACG | 1080 |
|  D  P  G  Q  L  L  Y  I  P  K  T  Y  L  L  G  R  P  R  N  A | |
| CGAGCCTGCCCGAGCTCCCCGAGGCGGGGCCCACGTCCCGTCCCCCGCCGAGGTGACCC | 1140 |
|  S  L  P  E  L  P  E  A  G  P  T  S  R  P  P  A  E  V  T  Q | |

Fig. 18a

```
AGCTCAAGGGACTGCTGCACAACCCCGGCGCCTCCGCGATGTTGCGGTCCCGGGCCTGGG        1200
 L  K  G  L  L  H  N  P  G  A  S  A  M  L  R  S  R  A  W  V

TAACATTCGCGGCCGCGCCGGACCGCGAGGGGCTTACGTTCCGCGGGGAGACGACGGGG         1260
 T  F  A  A  A  P  D  R  E  G  L  T  T  P  R  G  D  D  G  A

CGACCGAGAGGCACCCGGACGGCCGACGCAACGCGNCCCCGGGGCCGCCCGCGGGGGCGC        1320
 T  E  R  H  P  D  G  R  R  N  A  A  P  G  P  P  A  G  A  P

CGAGGCATCCGACGACGAACCTGAGCATCGCGCATCTGCACAACGCGTCCGTGANCCTGC        1380
 R  H  P  T  T  N  L  S  I  A  H  L  H  N  A  S  V  V  L  L

TGGCCGCCAGGGGCCTGCTACGGACTCCGGGTCGGTACGTGTACCTCTCCCCGTCGGCCT        1440
 A  A  R  G  L  L  R  T  P  G  R  Y  V  Y  L  S  P  S  A  S

CGACGTGGCCCGTGGGCGTCTGGACGACGGGCGGGCTGGCGTTCGGGTGCGACGCCGCGC        1500
 T  W  P  V  G  V  W  T  T  G  G  L  A  F  G  C  D  A  A  L

TCGTGCGCGCGCGATACGGGAAGGGCTTCATGGGGCTCGTGATATCGATGCGGGACAGCC        1560
 V  R  A  R  Y  G  K  G  F  M  G  L  V  I  S  M  R  D  S  P

CTCCGGCCGAGATCATAGTGGTGCCTGCGGACAAGACCCTCGCTCGGGTCGGAAATCCGA        1620
 P  A  E  I  I  V  V  P  A  D  K  T  L  A  R  V  G  N  P  T

CCGACGAAAACGCCCCGCGTGCTCCCCGCGCTCCGGCCGGCCCCAGGTATCGCGTCTTTG       1680
 D  E  N  A  P  R  A  P  R  A  P  A  G  P  R  Y  R  V  F  V

TCCTGGGGGCCCCGACGCCCGCCGACAACGGCNTCGGCGCTGGACCCCCTCGGCGGGTGG       1740
 L  G  A  P  T  P  A  D  N  G  G  A  G  P  P  R  R  V  A

CCGGCTACCCCGAGGAGAGCACGAACTACGCCCAGTATATGTCGCGGGCCTATGCGGAGT      1800
 G  Y  P  E  E  S  T  N  Y  A  Q  Y  M  S  R  A  Y  A  E  F

TTTTGGGGGAGGACCCGGGCTCCGGCACGGACGACGCGCGTCCGTCCCTGTTCTGGCGCC       1860
 L  G  E  D  P  G  S  G  T  D  D  A  R  P  S  L  F  W  R  L

TCGCGGGGCTGCTCGCCTCGTCGGGGTTTGCGTTCGTCAACGCGGCCCACGCCCACGACG       1920
 A  G  L  L  A  S  S  G  F  A  F  V  N  A  A  H  A  H  D  A

CGATTCGCCTCTCCGACCTGCTGGGTTTTTTGGCCCACTCGCGCGTGCTGGCCGGCCTGG      1980
 I  R  L  S  D  L  L  G  F  L  A  H  S  R  V  L  A  G  L  A

CCGCCCGGGGAGCAGCGGGCTGCGCGGCCGACTCGGTGTTCCTGAACGTGTCCGTGTTGG      2040
 A  R  G  A  A  G  C  A  A  D  S  V  F  L  N  V  S  V  L  D

ACCCGGCGGCCCGTCTGCGGCTGGAGGCGCGCCTCGGGCATCTGGTGGCCGCGATCCTCG      2100
 P  A  A  R  L  R  L  E  A  R  L  G  H  L  V  A  A  I  L  E

AGCGAGAGCAGAGCCTGGCGGCGCACGCGCTGGGCTATCAGCTGGCGTTCGTGTTGGACA     2160
 R  E  Q  S  L  A  A  H  A  L  G  Y  Q  L  A  F  V  L  D  S

GCCCCGCGGCCTATGGCGGGTTGGCCCCGAGCGCGGCCCGCCTGATCGACGCCCTTGTTA     2220
 P  A  A  Y  G  G  L  A  P  S  A  A  R  L  I  D  A  L  V  T

CCGCGCAGTTTCTCGGCGGCCGCGTAACCGCCCCGATGGTCCGCCGAGCGCTGTTTTACG     2280
 A  Q  F  L  G  G  R  V  T  A  P  M  V  R  R  A  L  F  Y  A

CCACGGCCGTCCTCCGGGCGCCGTTCCTGGCGGGCGTGCCCTCGGCCGGGCAGCGGGAAC    2340
 T  A  V  L  R  A  P  F  L  A  G  V  P  S  A  G  Q  R  E  R
```

Fig. 18b

```
GCCCGCGGGGCCTCCTCATAACCACGGCCCTGTGTACGTCCGACGTCGCCGCGGCGACCC     2400
 P  R  G  L  L  I  T  T  A  L  C  T  S  D  V  A  A  A  T  H

ACGCCGATCTCCGGGCCGCGCTACGCAGGACCGACCACCAGAAAAACCTCTTCTGGCTCC     2460
 A  D  L  R  A  A  L  R  R  T  D  H  Q  K  N  L  F  W  L  P

CGGACCACTTTTCCCCATGCGCACGTTCCCTGCCGTTCGATCTCGCCGAGGGCGGGTTCA     2520
 D  H  F  S  P  C  A  R  S  L  P  F  D  L  A  E  G  G  F  I

TCCTGGACGCGCTGGCCATGGCCACCCGATCCGACATCCCGGCGGACGTCATGGCACAAC     2580
 L  D  A  L  A  M  A  T  R  S  D  I  P  A  D  V  M  A  Q  Q

AGACCCGCGGCGTGGCCTCCGCTCTCACGCNCTGGGCGACTCACAACGCCCTGATCCGCG     2640
 T  R  G  V  A  S  A  L  T  T  W  A  T  H  N  A  L  I  R  A

CCTTCGTCCCGGAGGCCACCCACCAGTGTAGCGGCCCGTCGCACAACGNGGAGCCCCGGA     2700
 F  V  P  E  A  T  H  Q  C  S  G  P  S  H  N  N  E  P  R  I

TCCTCGTGCCCATCACCCACAACGCCAGCTACGTCGTCACCCACTACCCCCCTTGCCCCC     2760
 L  V  P  I  T  H  N  A  S  Y  V  V  T  H  Y  P  P  C  P  R

GCGGGATCGGATACAAGCTTACGGGCGTTGACGTCCGCCGCCCGCTGTTTATCACCTATC     2820
 G  I  G  Y  K  L  T  G  V  D  V  R  R  P  L  F  I  T  Y  L

TCACCGCCACCTGCGAAGGGCACGCGCGGGAGATTGAGCCGCCGCGGCTGGTGCGCACCG     2880
 T  A  T  C  E  G  H  A  R  E  I  E  P  P  R  L  V  R  T  E

AAAACCGGCGCGACCTCGGCCTCGTGGGGGCCGTGTTTCTGCGCTACACCCCGGCCGGGG     2940
 N  R  R  D  L  G  L  V  G  A  V  F  L  R  Y  T  P  A  G  E

AGGTCATGTCGGTGCTGCTGGTGGACACGGATGCCACCCAACAGCAGCTGGCCCAGGGGC     3000
 V  M  S  V  L  L  V  D  T  D  A  T  Q  Q  Q  L  A  Q  G  P

CGGTGGCGGGCACCCCGAACGTGTTTTCCAGCGACGTGCCGTCCGTGGCCCTGTTGTTGT     3060
 V  A  G  T  P  N  V  F  S  S  D  V  P  S  V  A  L  L  L  F

TCCCCAACGGAACTGTGATTCATCTGCTGGCCTTTGACACGCTGCCCATCGCCACCATCG     3120
 P  N  G  T  V  I  H  L  L  A  F  D  T  L  P  I  A  T  I  A

CCCCCGGGTTTCTGGCCGCGTCCGCGCTGGGGGTCGTTATGATTACCGCGGCCCTGGCGG     3180
 P  G  F  L  A  A  S  A  L  G  V  V  M  I  T  A  A  L  A  G

GCATCCTCAGGGTGGTCCGAACGTGCGTCCCATTTTTGTGGAGACGCGAATAAACGGGTG     3240
 I  L  R  V  V  R  T  C  V  P  F  L  W  R  R  E  *

TGTGGACGCAGCGGCGTCCAGCCCAACCCAACCGACTCCCTCCGTGTCCGCGGTCTGTTT     3300

GTTATTGTGTCCGCCGTGGCTCCGCTACCGCCTCTGTTCCTTTCCCTTCTCCATTCCTGT     3360

TTCCTTTCCTTCCCCCCCCCCCATAGTCCCCCGTATAGGCATACAACGGCATCCGTGGGT     3420
                       End of HSV2 UL21
TAGAAAACGACTGCACTTTATTGGGATATCTCACACAGACTGGCCGTGCTGGGCGCGAGC     3480
                       *  V  S  Q  G  H

CAGGCAAACGGTAAGCAGCGCGTCCAGGTACCCGGCGGTTCGCGTGCGGCCAGCCGCCCC     3540
```

Fig. 18c

| | |
|---|---|
| CGCCGGCCCGCGGTCAAACGCGGACATCCGGTCGACGTCCCCCACGGTCAGGACCAGGGA | 3600 - |
| CGTCACGCCCGTCAGGCGCNCGGTATGCGTGGCCGCGGCCAGGCGTCCGTGGCCGGCGTA | 3660 |
| CAACACGCCCAGGAACGCGCCGAGGTACATGACGTGCTCGGGCGAGACGGACCCCCCCGG | 3720 |
| GGTCAGGCGTTGCGAGTCCACAAAGCGCAGCAGGGCGGCGCTGTCGGCCCGCGACGTCGC | 3780 |
| TCCCCACCGGCACGTCCTTGGGCGGGAGGAGGTCGAACATGAGGAGCTGCTCGCGA | 3840 |

Fig. 19.

```
  1 CTGCAGGGGCGGCGGGTCGTGGCGGAGGATTGGGGACAGCTTTCGGGGCGGCGTGCCGCCCCCAGGGTGCCGAGCCCCAGAGCAACGCGGCCCACGAC 100
    ||||||  ||||||||| ||  ||||||| |||||  |||||| |||||| ||||||||  ||||| |||||||||||||  ||| ||||||  |||
  1 CTGCACCCGCGGCGGAGTTGGCGGGAGGACTGGGGCCTGACGGCTGGGGCGGACTGGGGGTCGCCGCGGGACCCCGACCCCGAGGACGGCGGGGTCTCTGC 100
    Oligo MB59

101 CCCATATCGGGGACACGTTATTACCCTGTTTCGGGCCCCCCGAGTTGCTGCTGGCCGGACCCTGTATAAACGTGTTTGCCTGGGCTTTGGACGTCTT 200
    |||         ||| |      |||||| ||| |  |||||||  ||  ||| |  |||| |||||  |||||||||||||||||||||||||||
101 CCCGCATCGAGGACACGCTGTTTGCCCTGTTCCCGCGTCCCGAGCTGCTGCCCGGGACTTGTACCACATTTTGCCTGGGTCTTGGACGTCTT 200

201 GGCCAAACGCCTCCGTCCCATGCATGTCTTTATCCTGGATTACGACCAATCGCCCTGCTGCAACTTACCTCCGGGATGGTC 300
    ||||    | ||| |||  ||||||  | |  |   |||||||||||||| |||||| ||||||||| |||||| ||| |
201 GGCCGACCGCCTCCTTCCGATGCATCAGTCGTGTCCTGATTACGACGATCGAGAGACGCCCTGTTGCGCCTGCGCCGGGGATGATC 300

.End of HSV1 TK
301 CAGACCCACGTCACCACCCCAGGCTCCATACCGACGATCTGCGACCTGGCCGGCGCGCACGTTTGCCCGGGAGAT.GGGGAGGCTAACTGAAACACGGAAGGA 399
    ||||||||  ||| |||||| ||   ||| | ||      | | |||||||||||||| ||| ||| ||||||     | | |||||||||||||
301 CCAACCCGCGTCACAACCGCCGGGTCCATCGCCGAGATACGCCGACCTGGCCGCGCGCACGTTTGCCCGACGTTTAGTTCAAACACGGAAG.. 398

End of HSV2 TK
400 GACAATATACCGGAAGGAACCCGCTATGACGGCAATAAAAGACAGAATAAAACGCACGGGTCGTGTTGCGGTCGTTGTTCATAAACGC.GGGGTTCGGTCCC 498
     | |  | || |||| |        |||  |||||||||    |||||||||| || |||    |||| |  |                   ||||  ||
399 ..CCCGAACGGAAGGCCCTCCCCGGCGATGACGGCAATAAAAGAACAGAATAAAAGGCATTGTTGTCGTGTGTCCATAAGCGCGGGGGTTCGGGGCC 496

499 AGGGCTGGCACTCTGTCGATACCCCCACCGAGACCCATTGGACCAATACGCCC........................GCGTTTCTTCCTTTTCCCCAC 573
    ||||||||| | ||||| || |||  |||| |||   || ||||  ||||||                          |||||||  |||  ||||||
497 AGGGCTGGCCACCGTATCAGCGATGGGCACCGAAAAACGGAGCGGGCCCATCCGTCCTTGTTTTCGGGTCTCGGTACTCCCCTTTGTGCTTTTACCCTCACCCCAC 596

574 CCCAACC..................CCCAAGTTCGGGTGAAGGCCCAGGGCTCGCAGCCAACGTTCGGGGCGGCAAGCCTGCCATAGCCACGGGCCCC 653
    ||| |                     |||| ||   |   ||||  ||| | | |||||     |  || ||||| |||  |||
597 CCCATCCTTTGGCCCGCGCTTACGGCAACAAAGGCCCTCCGATAGCCTCCGAGGTGCGACGCTCTTTGGGCCGCTGGGTACGGACACCCCCCATCTGCG 696

Start of HSV1 gH
654 GTGGGTTAGGGACGGGGTCCCCCATGGGGAATGTTTATGGTTCGTGGGGTTATTATTTTGGGCGTTGCGTGGGTCAGTCCACGACTGGACTGAGCA 753
     |||| ||||   | |||  |||||||                ||||||                    |   |||||| ||||||
697 GACTGCAGCCCGGACGACGAGCCGGACCATGGGCCCCGGTTCTGTGGGTGGTGATGGGGGTCCTGGTGGCCGGGGCCATGGACCACGTGACACCTGGACGGAGCA 796

Oligo MB75 Start of HSV2 gH

754 GACAGACCCATGTTTTGGATGGCCTGGGCATGACGGCCATGTACTGGCGCGCGACGACGAACACCGGCTGCCAAAACACCCCGACCCCAA 853
    |    | ||| | ||  || || |||||||| |  |||| | |  ||| | ||||   |||  ||||  |   ||||||  || ||||
797 AATCGACCCGTGTTTTTGCACGGTCTGGGGTTGCCCCAGCGTCAGTGTGGCGTCTGTGGTTGCCGGACACAAACACCGGCGTCACCCCCGACCCCAG 896
```

Fig. 19a

```
 854 AAACCACC..GCGCGGATTTCTGGCGCCGCCGGACGAACTAAACCTGACTACGGCATCTCTGCCCCCTTCTTCGCGTGGTACGAGGAGCGCTTTTGTTTTGTA   952
        |||||||  ||||||||| ||||||||||||||| ||||||||||||||||| |||||:   |||||||||||||||:||
 897 CGACCCCAGCGCGGACGCTTGGCGCCCCCGGGC.AACTCAACCTGACTACGGCATCCGTGCCCATGCCTTCGGTGGTACGCCGAGCGCTTTGTTTCGTG        995

953 TTGGTCACCACGGCCGAGTTTCCGCGGGACCCCGGCCCAGCTGCTTTACATCCGAAGACCTACCTGCTCGGCCGGCCCCCGAACGCGAGCCTGCCCGCCC       1052
     ||||||||||||||:||||||||||||||||||||||||||||:|||||||||||||||||||:|||||||||||:|||||||||||||||||:||||:
 996 TTGGTCACCACGGCCGAGTTTCCTCGGGACCCCGGGCCAGCTGCTTTACATCCAAAGACCTATCTGCTCGGCCGGCCTCGGAACGCGAGCCTGCCCGAGC       1095

1053 CCACCACGCGTCGAGCCGACGGACCCTCCCCCCTCGGTCGCCCCCCTTAAGGGTCTCTTGCACAATCCAGCCGCCTCCCGTTGCGCTTCCGGGC              1152
       ||||||||| ||||||||||||| ||||  ||:|||  ||    |||  ||    |||  ||||||||  |||||||||  |||||||||:|||
1096 TCCCCGAGGCGGGGCCACGTCCCCGTCCCCGCCGAGGTGACCCCAGCTCAAGGGACTGCTGCACAACCCCGGCGCCTCGCGGATGTTGCGGTCCCGGGC       1195

1153 CTGGGTAACGTTTTCGCGCCCGTCCCTGACCCCGAGGCCCTGACGTTCCCGCGGGAGACAACGTGGCGACGGCACCCGAGCGCACCCGGCGGCCCGCTGAATACA       1252
     ||||||||||:|||:||||||||   | ||:|||||||| ||||  ||| |:|||| | ||||| ||| ||| ||| |    ||| ||||  |||||  ||
1196 CTGGGTAACATTCGCGGCCCGTCGCGCGACGCCGAGGGGCTTACGTTNCCGCGGGAGCGGACGACGCACCGCCACCTGCTCACGAGGCACCACCCGGGACACG...CAAC       1292

1253 CCGCCCCCCCGACCGCCGGTTGGGCCCCGGCGGCGCAGGAGCTGACACATCACGACCTGCACAAGCGTCCACGACCTGTTGGCCACCCGGG                     1352
       |||:||||| ||||| |||    || |||| || |||| ||  ||| ||||   |||| | ||| ||||  ||| |||||| |||||||
1293 GGCNCCCCGGGGCGCCGCGCCCGGGGGGCGCGGCGCCGAGGCATCGAGCGAACCTGCACAACGCGCGAACGCGTCCGTGANCCTGCTGGCCCGCCAGGG      1392

1353 GCCTGTTGAGATCCCCAGTAGTACGTGTATTTCTCCCCGTCGGGCTCGACGTGGGCATCTGGACGTTGGACGACGGGGAGCTGGTGCTCGGGTGCGA                1452
     ||||||||||||||||||| ||| |||||||||||||| |||||| ||||||||||||||||||||||| ||||| |||  ||||||| ||||||||
1393 GCCTGCTACGGACTCGGGTCGTGTACGTGTACCTCTCCCCGTCGGCCTCGACGTGCCCGTGATATCGATGGGGACACAGCCCCTGGCGTTCGGGTGCGA      1492

1453 TGCCCGGCCTGCTGGTGCGCGCGCGCTACGGGCGGAATTCATGGGGCTCGTGATATCCATGCACGACAGCCCTCCGGTGAAGTGATGGTCCCCGGGC             1552
     ||||||||| ||| ||||||||| |||| ||| | ||  |||| ||| |||||||| |:||||||||||||| ||||| || || ||  ||||||
1493 CGGCCGGGCTCGTCGTGCGCGCGGATACGGGGAAGGGGCTTCATGAGGCTCGTGATATCGATGCACGACAGCCCCCCGGTCGATGTGGCGCCTGCGGAC       1592

1553 CAGACGCTAGATCGGGTCGGGACAACGGCTCGGCTGGAACGCCCCTCCGCGGGGCCCCCCGGCGGGGC          TCCCCGCGCTCGGCCGCTACCCGGAGGAGGCCACGAACTACGCCCAGTTCCTGCTCGTCGGGGT      1652
     ||||||||||||:||:|||||  ||||||||::|||| |   | |||||||||||:   || ||          |||||:|||||||||||||||||||||||||||||||||||||||||  ||:|  |||
1593 AAGACCCTCGCTCGGGGTCGGGAAATCGACGAAAAACGCCCCGTGC...TCCCCGCGCTCGGCCGCTACCCGGAGGAGGCCACGAACTACGCCCAGTATCGGTCTTTGTCCTAGGGT          1689

1653 CCCTGACGCGGGGCCGACAACGGCTCGGCTGAACGCGCTCGGCTGGAGGAGGCCACGAACTACGCCCAGTTCCTGCTCGTCGGGGC       1752
     ||||:|||||                     ||||||||||||||||||||||||||||||||||||||  ||:|   ||||||
1690 CCCCGACGCGCCCCGACAACGGCNTCGGGTCCCGCTACCCGGAGGAGGCCACGAACTACGCCCAGTATCGCCTGCTCTTTGTCCTGGGGG       1789

1753 ATACGCGGAGTTTTTCTCGGGGACGCGGGCGCCG...AGCAGGCGCCACGCGCACGGACGCCTCGGACGCGCCGCCTAACGGGCCTGCTCGCGACGTCGGGTTTT       1849
     ||||||||||||||||  |||||||||||    |    ||||||||||||||||:||||||||||||||||| ||| || ||||| || | |||| |||||
1790 CTATGCGGAGTTTTTGGGGGAGGACGCGCCCGGCGCTCCGGGCTCCGCCCTCGTCCCCTGTTCTGCGCCGTCCCGGGGCTCTCCGCCTCGCGAGTCGGGTTT       1889
```

Fig. 19b

```
1850 GCTTTCGTGAACGCCCGCCACGCAAACGGGCGGGTCGCCTCCGACCTGCTGCCTCTCCGACCTGCTGCCTCCGGGTTGCCGGGTTGCCGCCCGCG 1949
     || |||||  ||||||  ||||||  ||||  |||    |        |||||||||||        |||||||||||||||||||||
1890 GCGTTCGTCAACGCGGCCCACGCCCACGACGCGATTCGCCTCTCCGACCTGCTGGGTTTTTTGGCCCGTGCTGCTGGCCGCTGGCCCCGGG 1989
1950 GGGCCGCGGGCTGTGCCGCGGATTCTGTGTTTTTTAATGTGTCAGTCTTGATCTTGCAGTCTTGCAGGCCGCCTCCAGCACCTGGTGGC 2049
     |  ||||||   ||||||||||  |  ||||||  |||    |   ||     |||||||||  |||       |  |||||||
1990 GAGCAGCGGGGCTGCGCGGCCGACTCGGTGTTCCTGAACGTGTCCGTGTTGGACCCGGCGGGCCCGTCTGCGCGCTGGAGGCGCGCCTCGGGCATCTGGTGGC 2089
2050 CGAGATTCTGGAGCGCGAACAGAGAGCTTGGCATTACACGCGCTGGGCTGCTATCAGTCGCCCTTCGTGCTGTGGATAGCCCTCGGCGTACGACGCAGTGGCGCCC 2149
     ||  |       ||||||||||| | ||||||    |   |    || ||| ||||| ||||  ||| || | |||     |||||||  |||| ||||
2090 CGCGATCCTGAGCGAGCGAGAGAGCCAGAGCCTGGGCGCGCCACGCGCTGGGCTATCAGTCGCCTGGGCTTCGTGTTGGACAGCCCGGCCCTATGGCGGGTTGGCCCCG 2189
2150 AGCGCAGCCCATCTCACGACGCCCTGTATGCCGAGTTTCTAGGGGCGCCGTGCTGACACCCCGTCTGACCACCCGGCCTATTTTACGCCTCGGCTG 2249
     |||||||  || || ||  ||||||| | |||       |    ||||| |  ||       |     | |    |||  ||| | |||| ||
2190 AGCGCGGCCCCGCCTGATCGACGCCCCTTGTTACCGCGCAGTTTCTCGGCGGCCCGTAACCGCGTAACGGTCGCCGATGGTCCGCCGCGTAACGCCACGCCG 2289
2250 TCCTCCGGCAGCCGTTCTTGGCTGGCGTCCCCTCGGCGGTGCAGCGGGAACGCGCCCGCCGGAGCCTTCTGATAGCCTCGGCCCTGTGTACGTCCGACGT 2349
     ||  | ||||||||  | ||||||| |||  |   |  || ||||| ||||  |  | || | || |||       |||  ||||||||| |||||
2290 TCCTCCGGGCGCCGTTCCTGGCGTGCCCTCGGCCCGCCGCGTGCCCGGCCAGCGGGAACG...CCCGCGGGGGCCTCCCCTCATAACCACGGCCCTGTGTACGTCCGACGT 2386
2350 CGGCCGCAGCGACGACCAACGCCGACCTCCGGACGGCGCTGGCCATCTAGACGAGAGCGTGTGTTTATCCTGGACGCGCTGGCTCAAGCCACCCGAGATCCCGAGACCCCGGTCGCCCAGCAGACCC 2449
     ||  ||||  ||||| |||||||||||  |||||||||||  |||  |||| | ||| |||||     |   | |||||||||| |     |        ||||||     |||||| ||||
2387 CGCCCGGGGCGACCAGCCGACCGATCTCCGGGCGCCACCGCCGGTTCATCTCGGAGGGCGGGGTTCATCGCCGAGGCGCTGGCTCATGGCCACACTTTTCGCCATGCGCACGT 2486
2450 TCCCTGCGCTTTGATCTAGACGAGAGCGTGTGTTTATCCTGGACGCGCTGGCTCAAGCCACCCGAGATCCCGAGACCCCGGTCGCCCAGCAGACCC 2549
     |||||||||  ||||||||||   || |||||||  | ||||||||||||||||| |||||  ||   |  |||||||||||  ||||||||||
2487 TCCCTGCGCTTCGCGCCGATCTCCGGAGGGCGGGGTTCATCGCCGAGGCGCTGGCTCATGGCCACATCCCGGACGTCGACATCCGACATCCGACATCAGACCC 2586
2550 ACGGCCTCGCGCCTCGACCCGACGCGTTGGGCACGCGCCCTGAGCGCCTCACATCGTCGTGCGGGGGCAGTCTGCCAA 2649
     ||| ||  | |||||||||| ||||||:  ||||| || |||||||||| ||||  |||||||||||  ||| || |
2587 GCGGGCGTGCCTCCGCTCCAGCCGACTCACGCNCTGGGGCACTCACAACGCCCGATCCGCGTCCGGAGGCCACCAGTGTAGCGCCCGTCGCACAA 2686
2650 CGTCGAGCCACGGATCCTGGTACCCATCACCCACAAGCCAGCTACGTCGTCACCCACT...CCCCTCTGCCCCGGGGGATCGGCTACAAGCTCACCGC 2746
     || :||||||||||| |||||||||||   |||   | |||||||| |  ||   ||   |||||||  ||||||||||  ||||||||| |||||
2687 CGNGGAGCCCCGGATCCTCGTGCCCATCACCCACAAGCCAGCTACGTCGTCACCCACTACCCCGQCTTGCCCCCGGGGATCGGATACAAGCTTACGGGC 2786
2747 GTCGACGTCCGACGCCACTGTTCCTAACCTACCTCACCGCGAAGGCTCCACCATGCAGACTCCAAGCGGCTGGTGCCGCACCCAAAACC 2846
     || :||||||||||  ||||||    |||    ||||||||||||||||  ||   |  |  || |||||||||||||||||||| ||
2787 GTTGACGTCCGCCGCCGCCGCTGTTTATCACCATCCGCCGCTGTTTATCACCTATCTCACCGCTTTATCACCATCTACCGCCACCTGCGAAGGGCACGCGCGGAGATTGAGCGCGTGCCGACCGAAAACC 2886
```

Fig. 19c

```
3614 ACGCGACGTGCTCGGGGAGATCACCCCCCGGGGACGGCGAGACGTTGCGATTCTATAAAGCGCAGCAGAGACGTGCTGTGCGGCCTGC.ACGTCGCTTC 3712
     || ||||||||||||| |||  ||||  ||||||     |||||| ||   || |||||| |||| |||||||| ||||  ||||| ||  ||||||||
3687 ACATGACGTGCTCGGGGCGAGACGGACCCCCCGG...GGTCAGGCGTTGCGAGTCCACAAAGCGCAGCAGGGCGGCGCTGTCGGCCGACGTCGCTCC 3783

3713 CCACCGGCACGTCCTTGGGGGAGAAGGTCGAACATGAGAGAGCTGCTCG 3762
     |||||||||||||||||||| |||||||||||||||||||||||||||
3784 CCACCGGCACGTCCTTGGGCGGGAGGAGGTCGAACATGAGAGAGCTGCTCG 3833
                              Oligo MB58
```

```
  1 MGNGLWFVGVIILGVAWGQVHDWTEQTDPWFLDGLGMDRMYWRDTNTGRLWLPNTPDPQK  60
    :: :::  :  . .: :: :.    ::::  :::::  :::. : ::::::::::::::: :.
  1 MGFGLW VVMGVLVVAGGHDTYWTEQIDPWFLHGLGLARTYWRDTNTGRLWLPNTPDDQR  59

61 PPRGFLAPPDELNLTTASLPLLRWYEERFCFVLVTTAEFPRDPGQLLYIPKTYLLGRPPN 120
    ::      :...:...::::::.:.:::: ::::::::::::::::::::::::::::: :
 60 PPARTLGAPGQLNLTTASVPMLRWYAERFCFVLVTTAEFPRDPGQLLYIPKTYLLGRPRN 119

121 ASLPAPTTVEPTAQPPPSVAPLKGLLHNPAASVLLRSRAWVTFSAVPDPEALTFPRGDNV 180
    ::::    .::  ::.. : ::::::::.:: .::::::::: WVTF :: :.:: :::::.
120 ASLPELPEAGPTSRPPAEVTQLKGLLHNPGASAMLRSRAWVTFAAAPDREGLT PRGDDG 178

181 ATASHPSGPRDTPPPRPPVGARRHPTTELDITHLHNASTTWLATRGLLRSPGRYVYFSPS 240
    ::   :: : :. :   :: :: :::::..: : ::::::  ..: ::::: ::::::.:::
179 ATERHPDGRRNAPG   PPAGAPRHPTTNLSIAHLHNAS VLLAARGLLRTPGRYVYLSPS 235

241 ASTWPVGIWTTGELVLGCDAALVRARYGREFMGLVISMHDSPPVEVMVVPAGQTLDRVGD 300
    :::::::.:::::.::::::::::::::::..:::::::::::::::::  :...::: :: :::.
236 ASTWPVGVWTTGGLAFGCDAALVRARYGKGFMGLVISMRDSPPAEIIVVPADKTLARVGN 295

301 PADENPPGALPGPPGGPRYRVFVLGSLTRADNGSALDALRRVGGYPEEGTNYAQFLSRAY 360
    : :::.: : :  ..::::::::::::: : :::::.: .. :::.::::::::::..::::
296 PTDENAPRA PRAPAGPRYRVFVLGAPTPADNGGA GPPRRVAGYPEESTNYAQYMSRAY 353

361 AEFFSGDAG AEQGPRPPLFWRLTGLLATSGFAFVNAAHANGAVCLSDLLGFLAHSRALA 419
    :::...:.:  .   ...::  ::::: ::::  ::::::::::::::..: ::::::::::::: ::
354 AEFLGEDPGSGTDDARPSLFWRLAGLLASSGFAFVNAAHADAIRLSDLLGFLAHSRVLA 413

420 GLAARGAAGCAADSVFFNVSVLDPTARLQLEARLQHLVAEILEREQSLALHALGYQLAFV 479
    :::::::::::::::::::::::.:::::::  :::  :::::  ::::  :::::::::: ::::::::::::
414 GLAARGAAGCAADSVFLNVSVLDPAARLRLEARLGHLVAAILEREQSLAAHALGYQLAFV 473

480 LDSPSAYDAVAPSAAHLIDALY AEFLGGRVLTTPVVHRALFYASAVLRQPFLAGVPSAV 538
    :::: :.....::::. .::.::::: : :.:.:::::: :::: ::::::::::
474 LDSPAAYGGLAPSAARLIDALVTAQFLGGRV TAPMVRRALFYATAVLRAPFLAGVPSAG 532

539 QRERARRSLLIASALCTSDVAAATNADLRTALARADHQKTLFWLPDHFSPCAASLRFDLD 598
    ::::.  :..::  :::::::::::: ::  :   :::: ::::::::::::::  :: :::
533 QRERP RGLLITTALCTSDVAAATHADLRAALRRTDHQKNLFWLPDHFSPCARSLPFDLA 591

599 ESVFILDALAQATRSETPVEVLAQQTHGLASTLTRWAHYNALIRAFVPEASHRCGGQSAN 658
    :.. ::::::: ::::.  ::  ::  :::::::::::::::  :  .: : :
592 EGGFILDALAMATRSDIPADVMAQQTRGVASALT WATHNALIRAFVPEATHQCSGPSHN 650

659 VEPRILVPITHNASYVVTH SPLPRGIGYKLTGVDVRRPLFLTYLTATCEGSTRDIESKR 717
    :::::::::::::::::  : ::::::::::::::::::::: :::::::: :..: :
651 EPRILVPITHNASYVVTHYPPCPRGIGYKLTGVDVRRPLFITYLTATCEGHAREIEPPR 709

718 LVRTQNQRDLGLVGAVFMRYTPAGEVMSVLLVDTDNTQQQIAAGPTEGAPSVFSSDVPST 777
    :::::.:: ::::::::::::::::::::::::::::::::::: ::  :: : ::::::::
710 LVRTENRRDLGLVGAVFLRYTPAGEVMSVLLVDTDATQQQLAQGPVAGTPNVFSSDVPSV 769

778 ALLLFPNGTVIHLLAFDTQPVAAIAPGFLAASALGVVMITAALAGILKVLRTSVPFFWRR 837
    :::::::::::::::::::: ..: ::::::::::::::::::::::::: :: :::.::::::
770 ALLLFPNGTVIHLLAFDTLPIATIAPGFLAASALGVVMITAALAGILRVVRTCVPFLWRR 829

838 E 838
    :
830 E 830
```

VIRAL VACCINES

This is a continuation-in-part application of U.S. Ser. No. U.S. Ser. No. 08/030,073, filed May 20, 1993, now abandoned, which is the U.S. National filing of PCT/GB91/01632, filed Sep. 23, 1991, claiming priority to U.K. application 9020799.4, filed Sep. 25, 1990 and U.K. application 9104903.1, filed Mar. 8, 1991, and this is also a continuation-in-part of 08/168,643, filed Dec. 16, 1993, now abandoned.

The present invention relates to viral vaccines.

Viral vaccines are traditionally of two sorts. The first sort are 'killed' vaccines, which are virus preparations which have been killed by treatment with a suitable chemical such as beta-propriolactone. The second type are live 'attenuated' vaccines, which are viruses which have been rendered less pathogenic to the host, either by specific genetic manipulation of the virus genome, or, more usually, by passage in some type of tissue culture system. These two types of vaccine each have their own disadvantages. Since killed vaccines do not replicate in the host, they are usually administered by injection, and hence may generate an inappropriate kind of immune response. For example the Salk vaccine, a killed preparation of poliovirus, produces an imunoglobulin (Ig) G antibody response, but does not stimulate the production of IgA in the gut, the natural site of primary infection. Hence this vaccine, though it can protect the individual from the neurological complications of poliomyelitis, does not block primary infection, and so does not confer "herd immunity". In addition, killed viruses, do not enter and replicate inside host cells. Hence any beneficial immunological response to non-structural proteins produced during replication is not available. They also often fail to stimulate the production of cytotoxic T cells directed against virus antigens. "Dead" antigens can be picked up by antigen presenting cells and presented to T cells. However, the presentation occurs via MHC Class II molecules and leads to stimulation of T helper cell. In turn, the T helper cells help B cells to produce specific antibody against the antigen. In order to stimulate the production of cytotoxic T cells, virus antigens must be processed through a particular pathway inside the infected cell, and presented as broken-up peptide fragments on MHC Class I molecules. This degradation pathway is thought to work most effectively for proteins that are synthesised inside the infected cell, and hence only virus that enters host cells arid expresses immunogenic viral protein is capable of generating virus-specific cytotoxic T cells. Therefore, killed vaccines are poor inducers of cytotoxic T cells against virus infection. From this point of view, live attenuated vaccines are more satisfactory.

To date, live attenuated viruses leave been made by deleting an unessential gene or partly damaging one or more essential genes (in which case, the damage is such that the genes are still functional, but do not operate so effectively). However, live attenuated viruses' often retain residual pathogenicity which can have a deleterious effect on the host. In addition, unless the attenuation is caused by a specific deletion, there remains the possibility of reversion to a more virulent form. Nevertheless, the fact that some viral protein production occurs in the host means that they are often more effective than killed vaccines which cannot produce such viral protein.

Live attenuated viruses, as well as being used as vaccines in their own right, Can also be used as 'vaccine vectors' for other genes, in other words carriers of genes from a second virus (or other pathogen) against which protection is required. Typically, members of the pox virus family eg. vaccinia virus, are used as vaccine vectors. When a virus, is used as a vaccine vector, it is important that it causes no pathogenic effects. In other words it may need to be attenuated in the same way that a simple virus vaccine is attenuated. The same disadvantages as those described above, therefore apply in this case.

It has been found possible to delete an essential gene from a viral genome whilst also providing a so-called 'complementing' cell which provides the virus with the product of the deleted gene. This has been achieved for certain viruses, for example adenoviruses, herpesviruses and retroviruses. For adenoviruses, a human cell line was transformed with fragments of adenovirus type 5 DNA (Graham, Smiley, Russell & Nairn, J. Gen. Virol., 36, 59–72, 1977). The cell line expressed certain viral genes, and it was found that it could support the growth of virus mutants which had those genes deleted or inactivated (Harrison, Graham & Williams, Virology 77, 319–329, 1977). Although the virus grew well on this cell line (the 'complementing cell line') and produced standard viral particles, it could not grow at all on normal human cells. Cells expressing the T-antigen-encoding region of the SV40 virus genome (a papovavirus) have also been shown capable of supporting the replication of viruses specifically deleted in this region (Gluzman, Cell, 23, 182–195, 1981). For herpes simplex virus, cell lines expressing the gB glycoprotein (Cai et al, J. Virol. 62, 714–721, 1987) the gD glycoprotein (Ligas and Johnson, J. Virol. 62, 1486, 1988) and the Immediate Early protein ICP4 (Deluca et al., J. Virol., 56, 558, 1985) have been produced, and these have been shown capable of supporting the replication of viruses with specifically inactivated copies of the corresponding genes.

WO92/05263 published on 2 Apr. 1992 provides a mutant non-retroviral virus whose genome is defective in respect of a gene essential for the production of infectious virus, such that the virus can infect normal cells and undergo replication and expression of viral antigen genes in those cells but cannot produce normal infectious virus.

Mutant non-retroviral viruses in accordance with the teaching of WO92/05263 provide a unique way of combining the efficacy and safety of a killed vaccine with the extra immunological response induced by the in vivo production of viral protein by the attenuated vaccine. In preferred embodiments, the invention of WO92/05263 comprises two features. Firstly, a selected gene is inactivated within the virus genome, usually by creating a specific deletion. This gene will be involved in the production of infectious virus, but preferably not preventing replication of the viral genome. Thus the infected cell can produce more viral protein from the replicated genetic material, and in some cases new virus particles may be produced, but these would not be infectious. This means that the viral infection cannot spread from the site of inoculation.

A second feature of the invention of WO92/05263 is a cell which provides the virus with the product of the deleted gene, thus making it possible to grow the virus in tissue culture. Hence, although the virus lacks a gene encoding an essential protein, if it is grown in the appropriate host cell, it will multiply and produce complete virus particles which are to outward appearances indistinguishable from the original virus. This mutant virus preparation is inactive in the sense that it has a defective genome and cannot produce infectious virus in a normal host, and so may be administered safely in the quantity required to generate directly a humoral response in the host. Thus, the mutant virus need not be infectious for the cells of the host to be protected and merely operates in much the same way as a conventional killed or attenuated virus vaccine. However, preferably the immunising virus is itself still infectious, in the sense that it can bind to a cell, enter it, and initiate the viral replication cycle and is therefore capable of initiating an infection within a host cell of the species to be protected, and producing therein some virus antigen. There is thus the additional opportunity to stimulate the cellular arm of the host immune system.

In particular, it is to be mentioned that WO92/05263 provided in vivo data which showed that intra-epithelial vaccination of mice via the ear with a mutant form (as described above) of HSV-1 gave better protection against later challenge with wild-type HSV-1, than similar vaccination with killed HSV-1. A clear protective effect against the establishment of latent infection in the cervical ganglia was also shown for vaccination with the mutant HSV-1.

The applicants call the above described mutant viruses DISC viruses (standing for defective infectious single cycle) and the basic concept is illustrated In FIG. 1. The present application goes on from the work disclosed in WO92/05263.

The present application makes the disclosures summarised below.

(1) In a study using the mouse ear model the results reported in WO92/05263 were confirmed. Intra-epithelial vaccination of mice with DISC HSV-1 led to complete protection against replication of the challenge virus wild type (w.t.) HSV-1. Little effective protection was provided by equivalent doses of inactivated HSV-1. DISC HSV-1 also protected against the establishment of latent infection in the cervical ganglia.

(2) Also in the mouse ear model it is shown that no significant differences in antibody titres were observed between animals vaccinated with DISC HSV-1 and an equivalent amount of inactivated HSV-1.

(3) Also in the mouse ear model it is shown that at low vaccination doses, inactivated HSV-1 failed to established a delayed-type hypersensitivity (DTH) response, whilst equivalent doses of DISC HSV-1 established a DTH response. At high doses, both DISc HSV-1 and inactivated HSV-1 induced similar DTH responses.

(4) Also in a mouse study it was shown that in contrast to vaccination with inactivated HSV-1, vaccination with DISC HSV-1 induced HSV-1 specific cytotoxic T cell activity.

(5) The in vivo mouse ear model was used to study long term prophylactic effect of DISC HSV-1. Two vaccinations of DISC HSV-1 was found to provide hotter long term protection against challenge with w.t. HSV-1 than two vaccinations of inactivated DISC HSV-1.

(6) The in vivo mouse ear model was used to investigate the prophylactic effect of DISC HSV-2 against HSV-2 infection. Intra-epithelial vaccination of mice with DISC HSV-2 provided better protection against replication of the challenge virus w.t. HSV-2 than inactivated DISC HSV-2.

(7) The in vivo guinea-pig vaginal model was used to study the prophylactic effect of DISC HSV-1 against HSV-2 Infection. It was shown that intra-epithelial or intra-vaginal vaccination with DISC HSV-1 provided a high degree of protection against the primary symptoms of HSV-2 infection. Immunisation with DISC HSV-1 or inactivated virus retarded growth of challenge virus w.t. HSV-2 in the vagina. Further intra-vaginal vaccination with DISC HSV-1 lessened the number of recurrent HSV-2 lesions in a 100 day follow-up period. Intra-epithelial vaccination with DISC HSV-1 and inactivated virus also resulted in reduced recurrent lesions, but compared to intra-vaginal vaccination with DISC HSV-1, the reduction was less.

(8) Oral and intranasal vaccination of guinea-pigs with DISC HSV-1 led to protection against acute disease symptoms following challenge with w.t. HSV-2. The intranasal route appeared to be more effective than the oral route.

The per vaginum vaccination route in comparison to oral or intra-nasal vaccination resulted in significantly lower levels of recovered virus following challenge.

(9) In guinea-pigs which had recovered fully from primary HSV-2 disease, the therapeutic administration of DISC HSV-1 either intra-vaginally or intra-epithelially resulted in an apparent reduction in the frequency of recurrent of disease symptoms compared with mock vaccinated animals.

(10) In guinea-pigs which had recovered fully from primary HSV-2 disease, intra-vaginal therapeutic administration of DISC HSV-2 was more effective in reducing the frequency of recurrence of disease symptoms than treatment with DISC HSV-1.

The present invention provides a pharmaceutical mutant which comprises a mutant non-retroviral virus whose genome is defective in respect of a gene essential for the production of infectious virus such that the virus can infect normal cells and undergo replication and expression of viral antigen genes in those cells but cannot produce normal infectious virus, for prophylactic or therapeutic use in generating an immune response in a subject infected therewith.

The defect may allow the production and release from the cells of non-infectious viral particles.

The present invention provides a pharmaceutical which comprises a mutant non-retroviral virus whose genome is defective in respect of a gene essential for the production of infectious virus such that the virus can infect normal cells and replicate therein to give rise to the production and release from the cells of non-infectious viral particles. The pharmaceutical may be a vaccine capable of protecting a patient immunised therewith against infection or the consequences of infection by a non-retroviral virus. The pharmaceutical may be a vaccine capable of protecting a patient immunised therewith against infection or the consequences of infection by the corresponding wild-type virus.

The pharmaceutical may be a therapeutic capable of treating a patient with an established non-retroviral virus infection. The pharmaceutical may be a therapeutic capable of treating a patient with an infection established by the corresponding wild-type virus.

The pharmaceutical may be sub-cutaneously, intra-muscularly, intra-dermally, epithelially-, (with or without scarification), nasally-, vaginally-, or orally-administrable comprising excipients suitable for the selected administration route.

The mutant may be from a double-stranded DNA virus. The mutant may be from a herpes virus. The mutant may be from a herpes simplex virus (HSV).

The mutant may be a type-1 HSV or a type-2 HSV. The defect may be in the glycoprotein gH gene.

The present invention provides a type-2 HSV whose genome is defective in respect of a gene essential for the production of infectious HSV-2 such that the virus can infect normal cells and undergo replication and expression of viral antigens in those cells but cannot produce normal infectious virus, for prophylactic or therapeutic use in generating an immune response in a subject infected with HSV eg HSV-2.

The mutant HSV-2 defect allows the production and release from the cells of non-infectious virus particles.

Also provided is a type-2 HSV whose genome is defective in respect of a gene essential for the production of Infectious HSV-2 such that the virus can infect normal cells and replicate therein to give rise to the production and release from the cells of non-infectious viral particles.

The mutant may be capable of protecting a patient immunised therewith against infection or the consequences of infection with HSV eg infection by the corresponding wild-type virus.

The mutant may be capable of treating a patient with an established HSV infection eg infection by the corresponding wild-type virus.

The defect may be in the glycoprotein gH gene.

The present invention also provides use of a mutant type-1 HSV whose genome is defective in respect of a gene essential for the production of HSV-1 such that the virus can infect normal cells and undergo replication and expression of viral antigen genes in those cells but cannot produce normal infectious virus, for preparation of a pharmaceutical for prophylactic or therapeutic use in generating an immune response in a subject against type-2 HSV infection.

The use may be in respect of pharmaceuticals for intra-epithelial (with or without scarification), Intra-vaginal, intra-nasal or per-oral administration.

The present invention also provides an assembly comprising a pharmaceutical (for prophylaxis ie a vaccine or for therapy ie a therapeutic) as described above in a container preferably a pre-filled syringe or glass vial/ampoule with printed instructions on or accompanying the container concerning the administration of the pharmaceutical to a patient to prevent or treat conditions caused by HSV infection. The printed instructions may concern the prevention or treatment of facial or genital lesions.

Vaccines containing the mutants as described can be prepared in accordance with methods well known in the art wherein the mutant is combined in admixture with a suitable vehicle. Suitable vehicles include, for example, saline solutions, or other additives recognised in the art for use in compositions applied to prevent viral infections. Such vaccines will contain an effective amount of the mutant as hereby provided and a suitable amount of vehicle in order to prepare a vaccine useful for effective administration to the host.

Dosage rates can be determined according to known methods. For example, dosage rate may be determined by measuring the optimum amount of antibodies directed against a mutant resulting from administration of varying amounts of the mutant in vaccine preparations. Attention is directed to New Trends and Developments in Vaccines, Editors: A. Voller and H. Friedman, University Park Press, Baltimore, 1978 for further background details on vaccine preparation.

Therapeutics comprising a mutant as herein provided can be formulated according to know methods to provide therapeutically useful compositions, whereby the mutant is combined in admixture with a pharmaceutically acceptable carrier vehicle. Suitable vehicles and their formulation are described in *Remington's Pharmaceutical Science* by E. W. Martin. Such compositions will contain an effective amount of the mutant hereof together with a suitable amount of carrier vehicle in order Lo prepare therapeutically acceptable Compositions suitable for effective administration to the host.

Typically vaccines are prepared as injectables, (traumatic or non-traumatic) either as liquid solutions or suspensions; solid forms suitable for solution in, or suspension in, liquid prior to injection may also be prepared. Preparations may also be encapsulated in liposomes. The active immunogenic ingredients are often mixed with excipients which are pharmaceutically acceptable and compatible with the active ingredient. Suitable excipients are, for example, water, saline, dextrose, glycerol, trehalose, or the like and combinations thereof. In addition, if desired, the vaccine may contain minor amounts of auxiliary substances such as other stabilisers and/or pH buffering agents, which enhance the stability and thus the effectiveness of the vaccine.

The vaccines may be administered parenterally, by injection, for example, subcutaneously, intraepithelially (with or without scarification). Additional formulations which are suitable for other modes of administration eg oral, vaginal and nasal formulations are also provided. Oral formulations include such normally employed excipients as, for example, pharmaceutical grades of trehalose mannitol, lactose, starch, magnesium stearate, sodium saccharine, cellulose, magnesium carbonate, and the like. The compositions may take the form of solutions, suspensions, tablets, pills, capsules sustained release formulations or powders.

The vaccines are administered in a manner compatible with the dosage formulation, and in such amount as will be prophylactically effective. The quantity to be administered will have been predetermined from preclinical and clinical (phase I) studies to provide the optimum immunological response.

The vaccine may be given in a single dose schedule, or preferably in a multiple dose schedule. A multiple dose schedule is one in which a primary course of vaccination may be with 1–3 separate doses, followed by other doses given at subsequent time intervals required to maintain and or re-enforce the immune response, for example, at 1–4 months for a second dose, and if needed, a subsequent dose(s) after several months. The dosage regimen will also, have been determined from preclinical and clinical studies as maintaining the optimum immunological response over time.

In order that the invention is more clearly understood, it will be further described by way of example only, and not by way of limitation, with reference to the following figures.

BRIEF DESCRIPTION OF THE FIGURES

FIG. 9a shows recurrent disease as the cumulative mean erythema index per animal. FIG. 9b shows recurrent disease as cumulative mean number of days with disease per animal.

FIG. 12 shows the mean log titre of w.t. HSV-2 (strain MS) per animal (guinea-pigs) with w.t. HSV-2 (strain MS) infection and which have been vaccinated via the vaginal, oral or nasal routes with a mock virus preparation, DISC HSV-1 or inactivated DISC RSV-1.

FIG. 18 shows the sequence (SEQ ID NO:1) of HSV-2 strain 25766 in the region of the gH gene including a translation of the gH gene in single letter amino acid code (SEQ ID NO:2).

FIG. 19 shows a comparison of the DNA sequence of HSV-1 (SEQ ID NO:3) and HSV-2 strain 25766 (SEQ ID NO:1) in the region of the gH gene.

FIG. 20 shows a comparison of the deduced amino acid sequences of the HSV-1 strain 17 (SEQ ID NO:4) and HSV-2 strain 25766 (SEQ ID NO:2) gH proteins.

EXAMPLES

Figure 1:
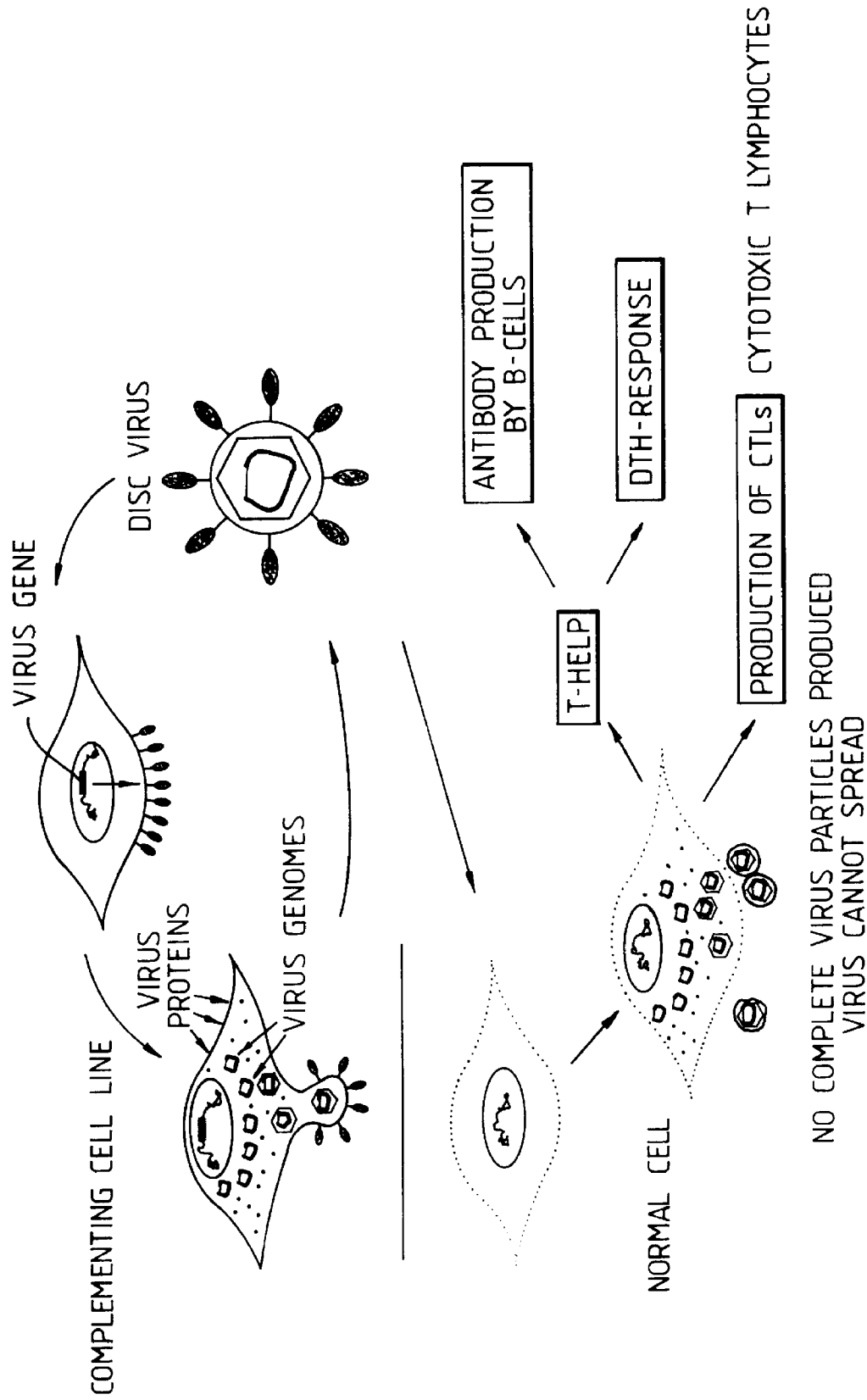
FIG. 1 illustrates the DISC virus concept.

Herpes Simplex Virus Deleted in Glycoprotein H (gH-HSV)

Herpes simplex virus (HSV) is a large DNA virus which causes a wide range of pathogenic symptoms in man, including recurrent facial and genital lesions, and a rare though often fatal encephalitis. In general, it seeing that type 1 HSV (HSV-1) seems to be particularly associated with facial lesions, whilst type 2 HSV (HSV-2) seems to be particularly associated with genital lesions. To some extent infection with HSV can be controlled by chemotherapy using the drug Acyclovir, but as yet there is no vaccine available to prevent primary infection or the consequences of this infection. Thus there is a need both for better therapeutics to treat established HSV infections and for prophylactics to prevent the establishment of HSV infection and/or its associated pathology.

A difficulty with vaccination against HSV is that the virus generally spreads within the body by direct transfer from cell to cell. Thus humoral immunity is unlikely to be effective, since circulating antibody can only neutralise extracellular virus. Of more importance for the control of virus infection, is cellular immunity, and so a vaccine which is capable of generating both humoral and cellular immunity, but which is also safe, would be a considerable advantage.

Figure 19C:
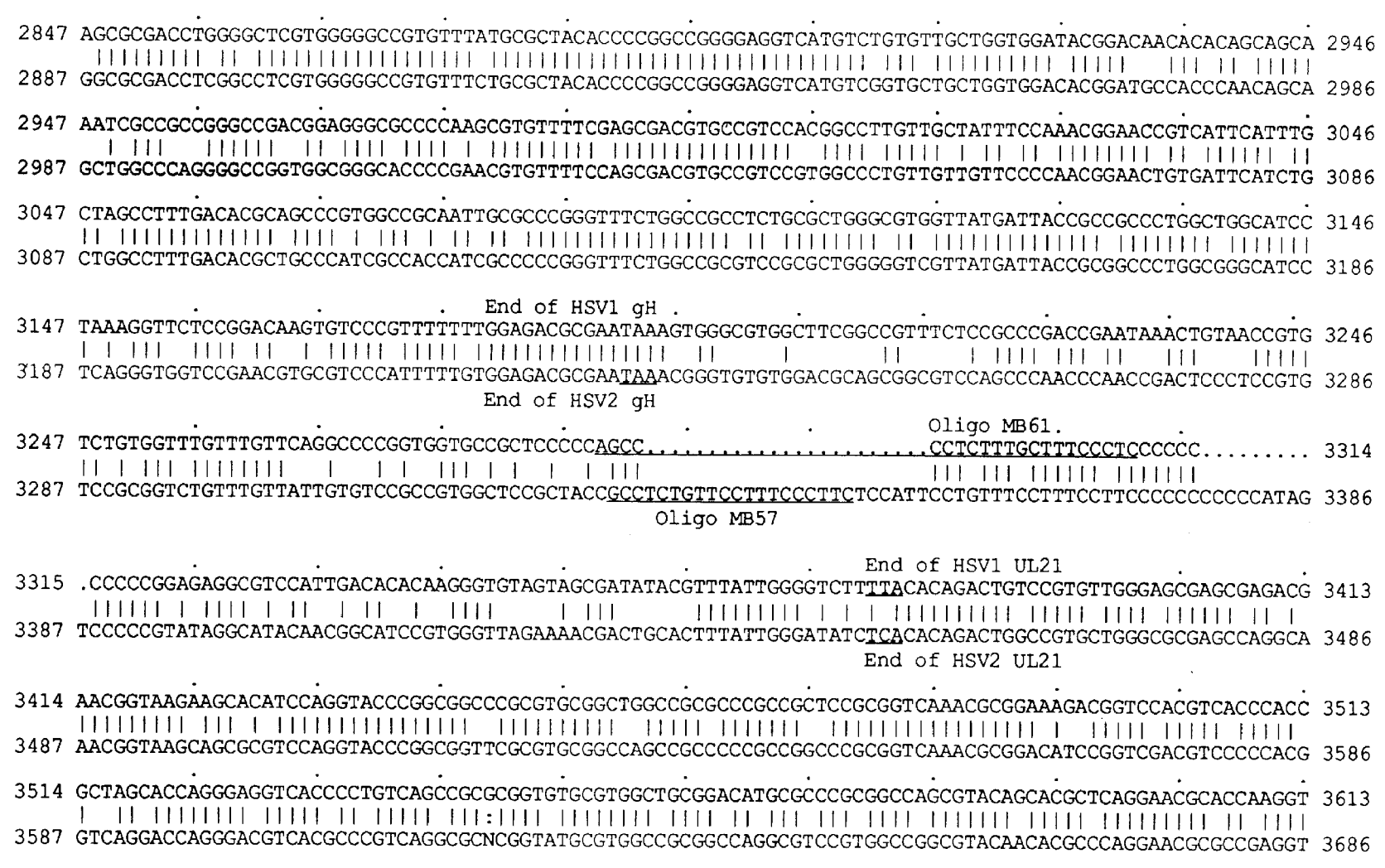

A suitable target gene for inactivation within the HSV genome is the glycoprotein H gene (gH). The gH protein is a glycoprotein which is present on the surface of the virus envelope. This protein is thought to be involved in the process of membrane fusion during entry of the virus into the infected cell. This -continued Inside left
           Hpa1
MB75 (SEQ ID NO:8) TCA<u>GTTAAC</u>CGTCGTCCCGGCTGCCAGTC Outside left
           Hind111
MB59 (SEQ ID NO:7) TCA<u>AAGCTT</u>CTGCAGCGCGGCGGGAGGTGG The position of these oligonucleotides is also shown on FIG. 19.

In accordance with the teachings made in PCT/GB91/01632 (WO 92/05263) and common general knowledge, such a plasmid allows the skilled person to produce a defective HSV-2 virus lacking precisely the sequences for the gH gene (see below). If these same sequences are cloned into a suitable cell carrying a copy of the gH gene deleted from the HSV- -continued Hpa1
MB109 (SEQ ID NO:12) TCAGTTAACTGCACTAGTTTTAATTAATACGTATGCCGTCCGTCCCGGCTGCCAGTC Construction of Recombinant Viruses a) First Stage.

Virus DNA was made from strain HG52-D, which is a plaque-purified isolate of the HSV-2 strain HG52. Virus DNA (2.5 µg) arid pIMMB47+ plasmid DNA (0.25 µg) was transfected into CR1 cells using the $CaPO_4$ precipitation method (Chen & Okayama, Molecular and Cellular Biology, 7, p. 2745). Recombination takes place within the cells, and a mixture of recombinant and wild type virus is produced. The mixture was plaque-purified three times on CR1 cells in the presence of acyclovir (10 µg/ml), to select for TK-minus virus. A single plaque was then grown up and analysed. The virus was titrated on normal Vero cells and on CR1 cells. If the virus is a gH-deleted virus, it should only grow on CR1 cells and not on Voro cells. Table 1 shows that this is the case. It can be seen that the virus does not grow at all on the non-complementing Vero cells even at the highest virus concentrations, but does grow well on the CR1 complementing cell line, which expresses the HSV-1 gH gene. The virus also grows well on CR2 cells which express the HSV-2 gH gene (data not shown).

TABLE 1 growth of first stage recombinant virus on complementing (CR1) and non-complementing (Vero) cells.

| | CR1 (gH+) | | | Vero | | | |
|---|---|---|---|---|---|---|---|
| Virus dilutions | $10^{-4}$ | $10^{-5}$ | $10^{-6}$ | $10^{-1}$ | $10^{-2}$ | $10^{-3}$ | $10^{-4}$ |
| Number of plaques | >350 >350 | 174 169 | 22 19 | 0 0 | 0 0 | 0 0 | 0 0 | b) Second stage.

Figure 27:
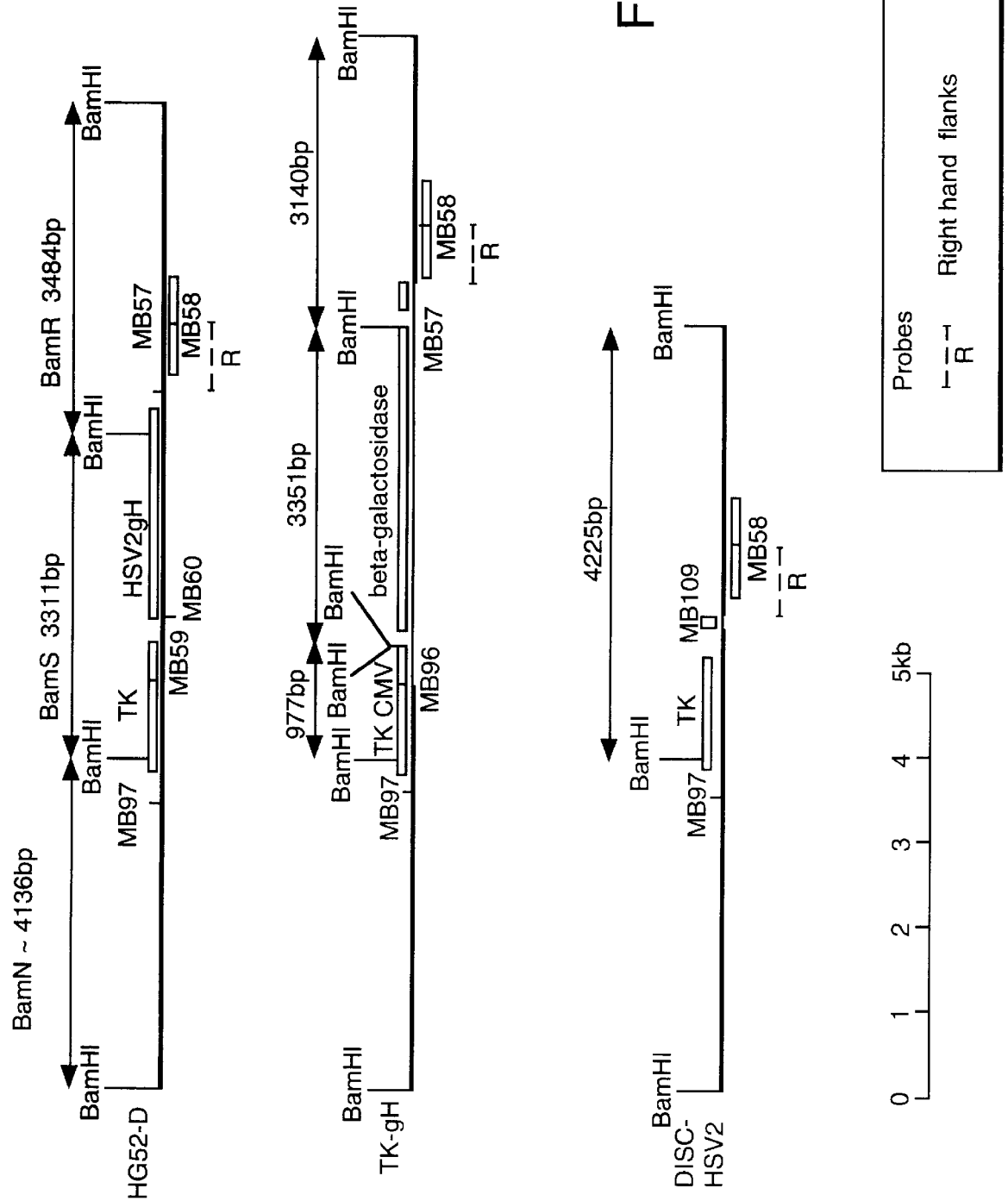
FIG. 27 shows a restriction map analysis for recombinants HG52-D, TK minus DISC virus, TK plus DISC virus.

DNA was made from this TK-minus DISC virus and a recombination was carried out as above with the plasmid pIMMB46. In this case TK-plus recombinants were selected, on a gH-expressing TK-minus BHK cell line, by growth in medium containing methotrexate, thymidine, glycine, adenosine and guanosine. Virus was harvested and grown again under selective conditions twice more before a final plaque purification was carried out on CR1. Virus was grown up and analysed by Southern blotting. Virus DNA from the original HG52-D, the TK-minus DISC virus, and the TK-plus DISC virus were digested with BamHI and separated on an agarose gel. The DNA bands were then transferred to nylon membrane by the Southern blotting method, and probed with radiolabelled fragments from the right hand flanking sequences. FIG. 27 shows the structures of these viruses, with the expected hand sizes after BamHI digestion The probe used is marked as 'R' beneath a dashed line. The probe should hybridise to a different size band in each of these viruses, as follows:

| Virus | Band size hybridising (base pairs) |
|---|---|
| HG52-D | 3481 |
| TK-minus "first stage" DISC virus | 3140 |
| TK-plus "second stage" DISC virus | 4225 |

Figure 28:
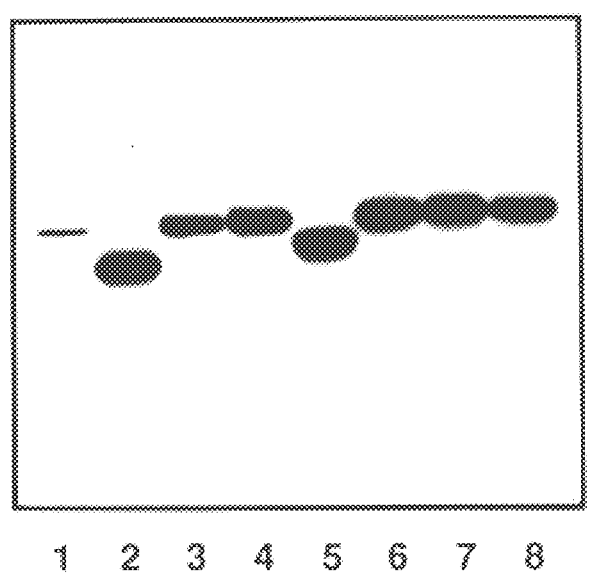
FIG. 28 shows Southern blots of BamHI digestions of various viruses, probed with the right-hand flanking sequence as shown in FIG. 27. Lane 5: HG52-D virus, lane 2: TK-minus "first stage" DISC virus and lanes 3, 4, 6, 7 and 8: TK-plus "second stage" DISC viruses.

FIG. 28 shows that this is the Case. Lane 5 shows the HG52-D virus, Lane 2 contains the TK-minus "first stage" DISC virus, and lanes 3, 4, 6, 7 and 8 contain TK-plus "second stage" DISC viruses. This confirms that the DNA structure in each of these viruses is as expected.

The present application refers to certain strains of HSV-1 and HSV-2. It is not necessary that the general teaching contained herein is put into effect with precisely the mentioned strains. Strains of HSV-1 and HSV-2 having high sequence homology to one another by which the invention may be put into effect are readily available. For example, one source of HSV is the American Type Culture Collection (ATCC), 12301 Parklawn Drive, Rockville, Md. 20852 USA. The following are available from ATCC under the indicated accession numbers.

| | |
|---|---|
| HSV-1 strain F: | ATCC accession no. VR-733 |
| HSV-1 strain MacIntyre: | ATCC accession no. VR-539 |
| RSV-1 strain MP: | ATCC accession no. VR-735 |
| HSV-2 strain G: | ATCC accession no. VR-734 |
| HSV-2 strain MS: | ATCC accession no. VR-540 |

IN VIVO MOUSE STUDIES
PROTECTION STUDIES

The in vivo mouse ear model was used to study prophylactic effects. Equivalent doses of inactivated wild-type HSV-1 (Strain SC16 see Hill et al. J. Gen. Virol. 28, p341–353 (1975)) and DISC HSV-1 were compared for their effect on the replication of w.t. HSV-1, their ability to provide protection against w.t. HSV-1 challenge and to induce HSV-specific neutralising antibodies.

4–5 week old BALB/c mice were vaccinated with varying doses of DISC HSV-1 or inactivated virus by scarification in the left ear pinna. Virus was inactivated using β-propiolactone (for further details see WO92/05263 published on 2 Apr. 1992 and corresponding to U.S. Pat. No. 5,665,362 issued Sep. 9, 1997, incorporated herein by reference). The mice were challenged with $2 \times 10^6$ pfu w.t. HSV-1 (strain SC16) in the opposite ear two weeks after vaccination. The amount of virus present in that ear 5 days post challenge was assayed by plaguing on BHK cells. (See FIG. 2.)

Figure 2:
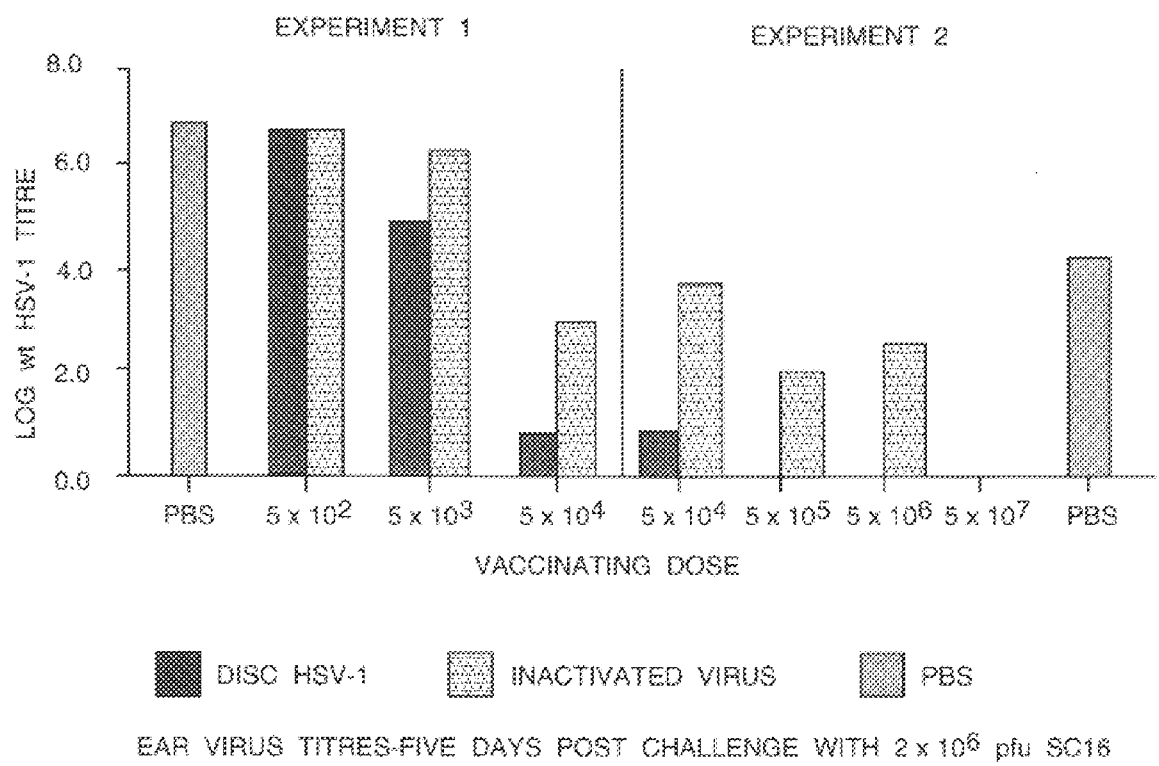
FIG. 2 shows clearance of wild-type HSV-1 (w.t. HSV-1) strain SC16 virus in the ears of mice vaccinated with either live DISC HSV-1 or inactivated (β-propriolactone treated) w.t. HSV-1 (strain SC16). Groups of 4 mice were vaccinated at the doses indicated by scarification of the left ear pinna. Mice were challenged 14 days post-vaccination with $2 \times 10^6$ pfu w.t. HSV-1 strain SC16 in the right ear pinna and virus titres were measured 5 days post challenge. Data are expressed as the geometric means and standard errors of the means.

It can be seen from FIG. 2 that vaccination with $5 \times 10^5$ and $5 \times 10^6$ pfu DISC HSV-1 (pfu measured on complementing cell line for DISC viruses) led to complete protection against replication of the challenge virus, whilst mice vaccinated with inactivated virus still had live challenge virus present.

A similar result was obtained when virus titres were assayed from the ganglia of vaccinated animals 5 days after challenge (data not shown).

SEROLOGICAL RESPONSE TO DISC HSV-1 VACCINATION

The role of antibody in protection conferred by the DISC HSV-1 vaccination was investigated. Both neutralising antibody titres and total antibody titres, as determined by ELISA, were measured.

Groups of 6 mice were vaccinated with $5 \times 10^6$ pfu of DISC HSV-1, killed DISC HSV-1, w.t. HSV-1 (strain SC16) or with PBS and serum samples taken at 2 and 14 weeks post vaccination. Neutralising antibodies were measured in the presence of complement and expressed as the inverse of the serum dilution which reduced the number of plaques by 50%. ELISA antibody titres were measured on plates coated with HSV-1 infected BHK cell lysates and titrated to endpoint. (See FIG. 3.)

Figure 3:
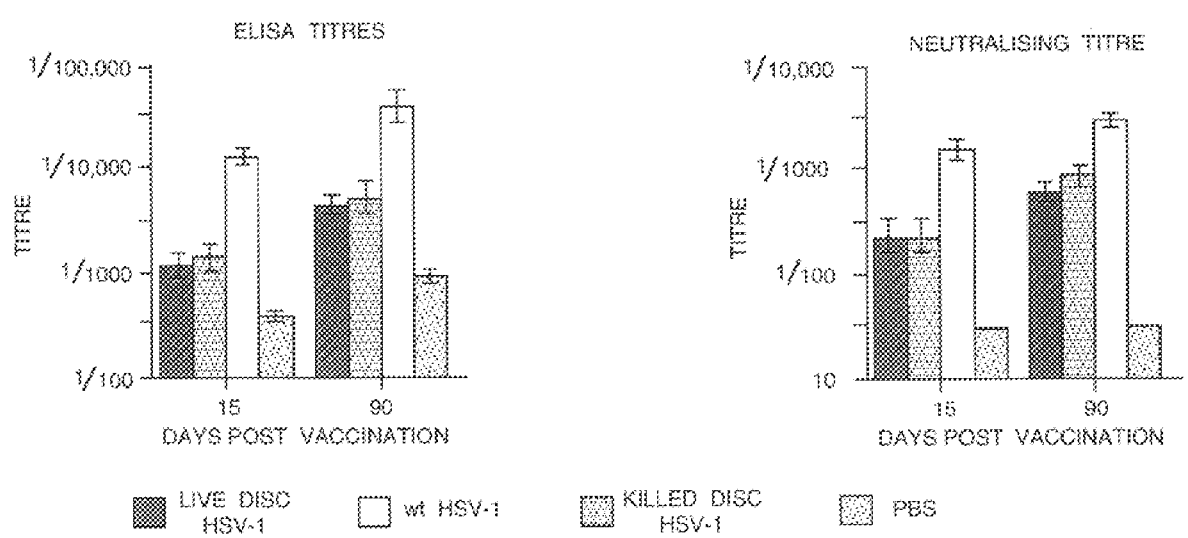
FIG. 3 shows measurement of titres of neutralising and ELISA antibody to w.t. HSV-1 in mice vaccinated with either w.t. HSV-1 (strain SC16), live DISC HSV-1, killed DISC HSV-1 or PBS. Sera from mice were assayed in the presence of complement for neutralising antibodies to w.t. HSV-1 in a plaque reduction assay. Individual titres are expressed as the reciprocal dilution of sera required to neutralise 50% of the infectivity obtained in the absence of antibody.

It can be seen from FIG. 3 that no significant differences in antibody titres were observed between animals vaccinated with DISC HSV-1 and an equivalent amount of killed DISC HSV-1.

DELAYED-TYPE HYPERSENSITIVITY (DTH) RESPONSE to DISC HSV-1 VACCINATION

The importance of a DTH response in protection against herpes virus infection has been well documented. The ability of the DISC HSV-1 to raise a DTH response was investigated by vaccinating groups of mice with DISC HSV-1, killed DISC HSV-1, and live w.t HSV-1, by scarification of the left ear pinna.

Four doses ($5 \times 10^3$, $5 \times 10^4$, $5 \times 10^5$ and $5 \times 10^6$ pfu) of vaccine were used, and two weeks later the vaccinated animals were challenged in the opposite ear with $10^6$ pfu w.t. HSV-1 (strain SC16). The DTH response at the site of challenge was assessed by measurement of ear thickness at 24 and 48 hours post challenge and expressed as the difference between the challenged and unchallenged ears. (See FIG. 4.)

Figure 4:
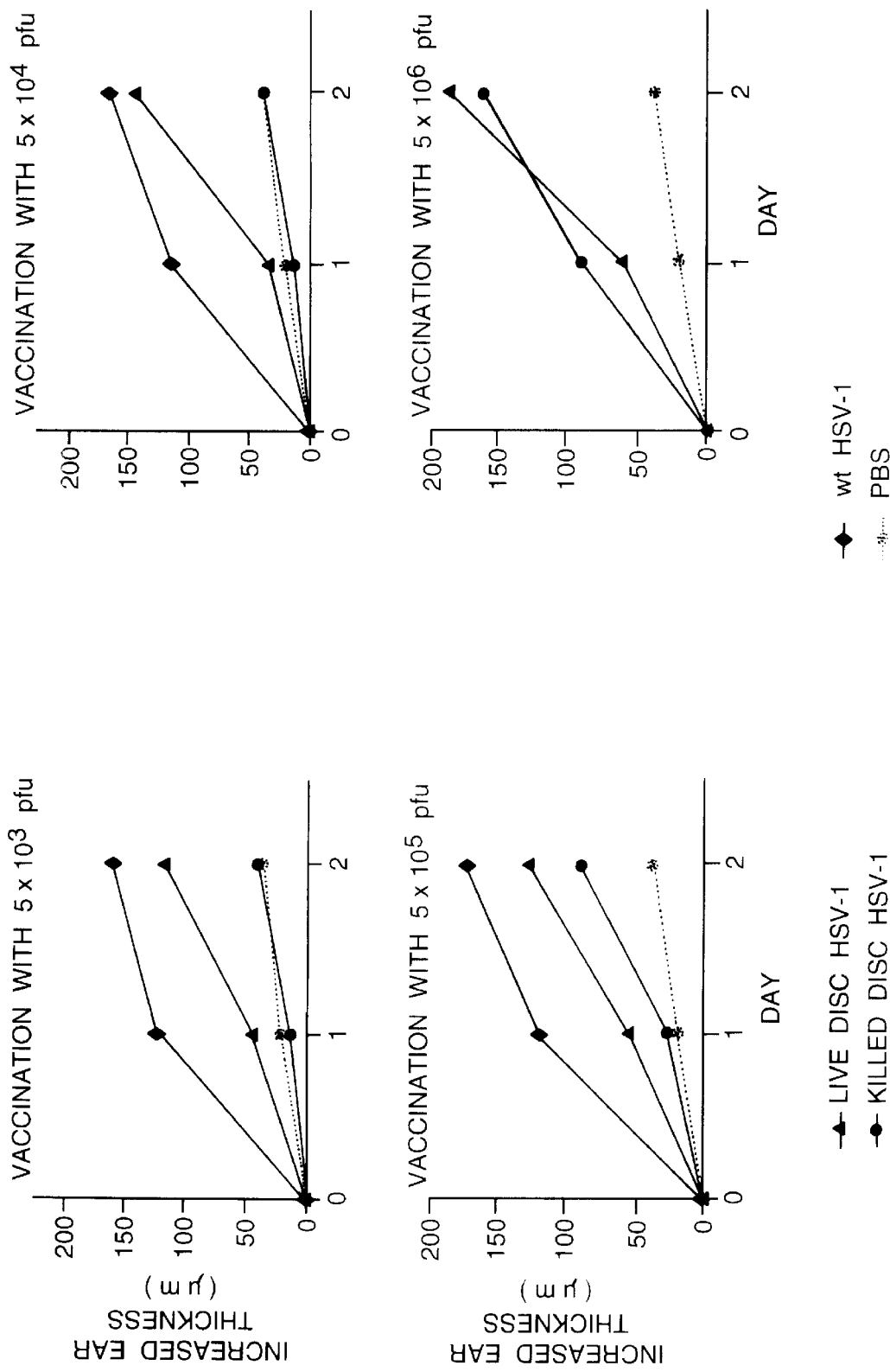
FIG. 4 shows delayed-type hypersensitivity (DTH) responses in mice vaccinated with either w.t. HSV-1 (strain SC16), live DISC HSV-1, killed DISC HSV-1 or PBS. Mice were vaccinated in the left ear pinna at the doses indicated 14 days prior to challenge with $10^6$ pfu w.t. HSV-1 (strain SC16) in the opposite ear. Ear thickness was measured 24 and 48 hours post-challenge and is expressed as the difference between the challenged and vaccinated ear. Data are presented as the means of differences in ear thickness (in $\mu$m).

It can be seen from FIG. 4 that at low vaccine doses ($5 \times 10^3$, $5 \times 10^4$ pfu), no DTH response was observed with killed DISC HSV-1, whilst a clear DTH response was demonstrated after DISC HSV-1 vaccination. At high doses, (eg $5 \times 10^6$ pfu), both the DISC HSV-1 vaccine and killed DISC HSV-1 preparations induced similar DTH responses.

The DTH responses induced by different doses of the various vaccine preparations thus correlate with their protective effect against challenge virus replication. The efficacy of vaccination with low doses of the DISC HSV-1 vaccine may therefore be due to the induction of T cell-mediated immunity.

DEMONSTRATION THAT DISC HSV TYPE 1 VIRUS IS CAPABLE OF GENERATING CYTOTOXIC T CELLS

Cytotoxic T cells have been shown to be involved in the protection against, and recovery from, primary HSV infection. DISC HSV-1 vaccinated mice were therefore studied for the presence of HSV-1 specific cytotoxic T cell activity.

Cytotoxic T cell activity following immunisation was generated and assayed according to standard procedures eg as exemplified in Martin, S. et al, 1988, J. Virol. 62: 2265–2273 and Gallichan, W. S. et al, J. Infect. Dis. 168: 633–629. More specifically, groups of female BALB/c mice were immunised intra-peritoneally with $2 \times 10^7$ pfu of virus (DISC HSV-1; killed DISC HSV-1; MDK a thymidine kinase negative HSV-1 strain) on day 0 and the immunisations repeated (same dose and route) after 3 weeks. A group of control mice received 0.1 ml of PBS intraperitoneally at the same time points. Ten days after the second immunisation the spleens of the mice were removed and pooled for each group.

Spleens were also removed from unimmunised BALB/c mice for the preparation of feeder cells (16 feeder spleens being sufficient for 4 groups of six effector spleens). All subsequent Steps were performed in a laminar flow hood using aseptic technique. The spleens were passed through a sterile tea-strainer to produce a single cell suspension in RPMI 1640 medium supplemented with 10% heat inactivated foetal calf serum (effector medium). Debris was allowed to settle and the single cell suspension was transferred to a fresh container. The cell suspensions were washed twice in effector medium (1100 rpm, 10 minutes) and then passed through sterile gauze to remove all clumps. The effector spleen cell suspensions were then stored on ice until required.

Feeder spleen cells were resuspended to $1 \times 10^7$ cells/ml in effector medium and mitomycin C was added to a final concentration of 20 µg/ml. The feeder cells were incubated at 370° C. for 1 hour. Feeder cells were washed four-times in PBS supplemented with 1% FCS and once in PBS with no protein. Live virus (MDK) was added to the mitomycin C treated feeder cell pellet at a concentration of 3 pfu of virus per spleen cell. Following a one hour incubation at 37° C. the feeder cells were washed once with effector cell medium.

Effector cells were resuspended to $5 \times 10^6$ cells/ml, whilst feeder cells were resuspended to $2.5 \times 10^6$ cells/ml. 500 µl of effector cell suspension and 500 µl feeder cell suspension were added to the wells of a 24 well plate. The plates were incubated in a humid atmosphere at 37° C. (5% $CO_2$) for 4 days.

The effector and feeder cells were harvested from the 24 well plate. The cells were spun down once and the pellet resuspended in effector medium (5 ml of medium per 2 plates). The cell suspension was layered onto lymphocyte separation medium and spun at 2500 rpm for 20 minutes. The live effector cells were harvested from the interface and washed twice, once at 1500 rpm for 15 minutes and once at 1100 rpm for 10 minutes. The effector cells were finally resuspended at the required concentration in effector medium and stored on ice until required.

Labelled target cells were prepared for the cytotoxicity assay. Uninfected syngeneic A202J target cells A20/2J cells were harvested from tissue culture flasks; $2 \times 10^7$ cells were added to each of 2 containers (to become infected and uninfected targets). The cells were washed with DMEM (with no additions). To the infected cells live MDK virus was added at 10 pfu per cell and an equivalent volume of EMEM was added to the uninfected cells. One mCi of 51Cr was added to each of the universals and the cells were incubated at 37° C. (in a waterbath) for 1 hour. The target cells were then washed three times (10 minutes, 1100 rpm) in target medium (DMEM supplemented with 10% FCS) and finally resuspended to the required cell concentration in target cell medium.

Both uninfected and infected target cells were resuspended to $1 \times 10^6$ cells/ml and $1 \times 10^5$ cells/ml and 100 µl (ie to give $1 \times 10^5$ targets/well and $1 \times 10^4$ targets/well respectively) was plated out into the appropriate wells of a round bottomed 96 well plate. All experimental points were set up in quadruplicate. Each effector cell type was resuspended to $8 \times 10^6$ cells/ml in effector medium and two-fold dilutions were prepared. 100µl of the effector cell suspensions were added to the wells containing the labelled target cells to give $8 \times 10^5$ effector cells/well, $4 \times 10^5$ effector cells/well, $2 \times 10^5$ effector cells/well and $1 \times 10^5$ effector cells/well. Thus with $10^5$ target cells per well, effector to target ratios were: 8:1, 4:1, 2:1 and 1:1. With $10^4$ target cells per well the effector to target ratios were 80:1, 40:1, 20:1 and 10:1. Maximum chromium release for each target cell type was obtained by adding 100 µl of 20% Triton X-100 to wells containing target cells only (ie no effectors). The spontaneous release for each target cell type was obtained by the addition of 100µl effector cell medium to wells containing target cells only.

The plates were incubated at 37° C. for four hours in a is humid atmosphere. After this time the plates were spun for four minutes at 1500 rpm arid 100 µl of supernatant was removed from each of the wells. The supernatant was transferred to LP2 tubes and radioactivity contained in the tubes was then counted for 1 minute on a gamma counter. The % specific chromium release was determined using the formula $$\% \text{ specific release} = \frac{\text{Exp. mean } cpm - \text{spon. mean } cpm}{\text{Max. mean } cpm - \text{spon. mean } cpm} \times 100$$

Exp. = Experimental
Spon. = Spontaneous
Max. = Maximum

Figure 5:
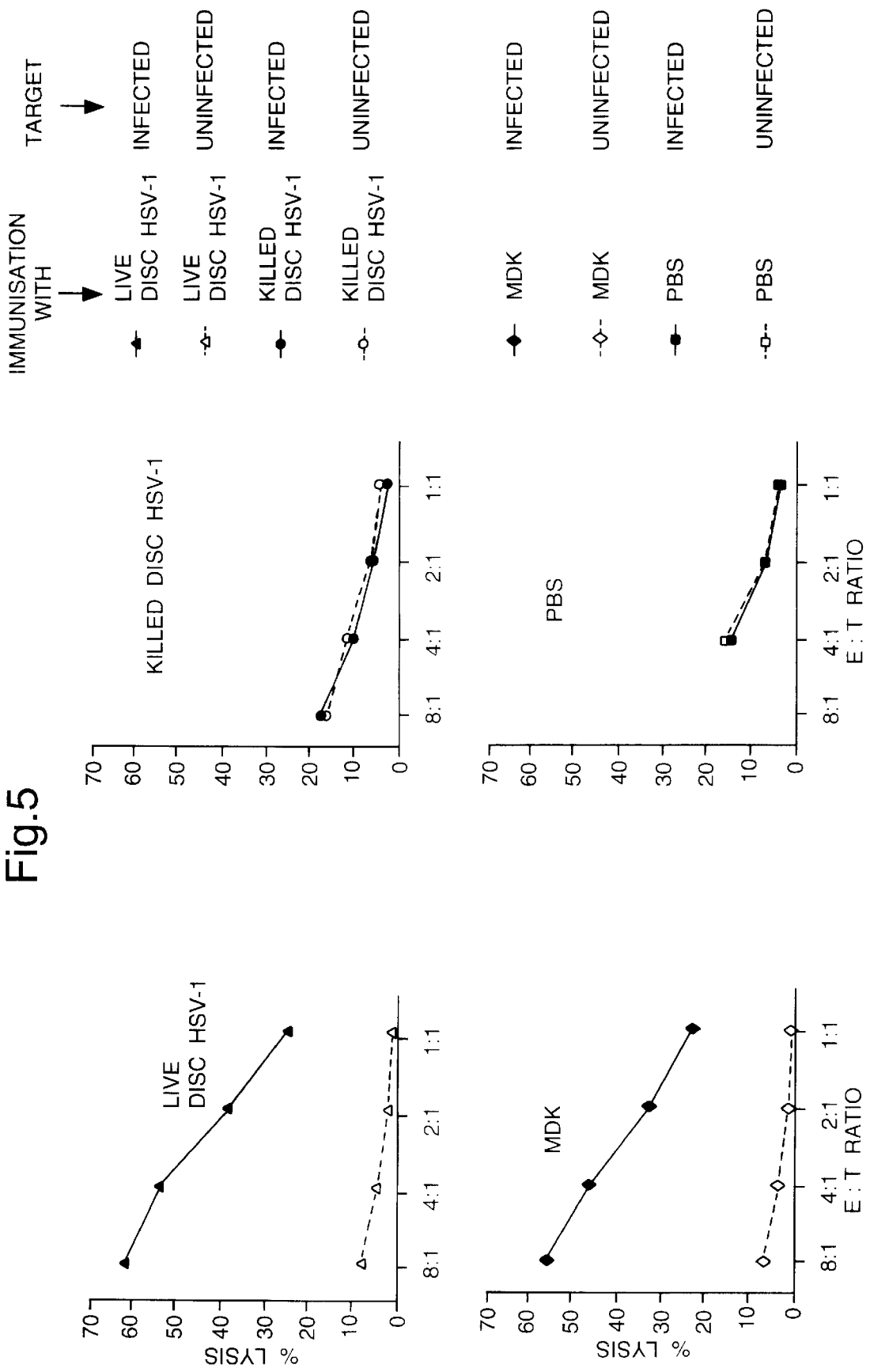
FIG. 5 shows cytotoxic T cell (CTL) responses in mice vaccinated with either live DISC HSV-1, killed DISC HSV-1, MDK (a thymidine kinase negative HSV-1 strain) or PBS. Mice were immunised twice intraperitoneally three weeks apart and cell suspensions made from spleens 10 days after the second injection. Cells were stimulated in vitro for 4 days before being tested in a CTL assay using $^{51}$Cr-labelled A20/2J as target cells. Data are presented as mean % $^{51}$Cr-release from quadruplicate samples at each point. Standard errors of the means are all <10%.

The results are shown in FIG. 5 and Table 1

TABLE 1

| E:T ratio | DISC HSV-1 | Inactivated Virus | MDK | Unvaccinated |
|---|---|---|---|---|
| 8:1 | 53.9 | 1.5 | 48.3 | ND |
| 4:1 | 49.6 | 0.0 | 42.2 | 0.0 |
| 2:1 | 36.9 | 0.0 | 31.0 | 0.0 |
| 1:1 | 23.9 | 0.0 | 21.9 | 0.0 |

% HSV-1 Specific Lysis
(% lysis of HSV-infected cells minus % lysis of uninfected cells).

DISC HSV-1 vaccination induced HSV-1 specific CTL activity comparable to that produced by infection with the fully replicative MDK virus. In contrast no HSV-1 specific CTL activity was observed in mice immunised with killed DISC HSV-1 or in PBS treated animals, although some non-specific killing was observed in these animals. The reason for this is not clear, but it could represent a high level of NK cell activity.

Vaccination of mice with the DISC HSV-1 has thus been shown to induce antibody, CTL and DTH activity against HSV-1 virus antigens. The ability to activate both humoral and cell-mediated immune responses against a broad spectrum of virus proteins may explain the effectiveness of the DISC virus vaccination.

LONG-TERM PROTECTION

The in vivo mouse ear model was used to study long term prophylactic effect of DISC HSV-1

4–5 week old BALB/c mice were divided into groups containing 6 animals each. The groups were vaccinated as follows:

| Group | Vaccination |
|---|---|
| PBS | Mock immunisation with PBS |
| 1K | 1 immunisation with inactivated DISC HSV-1 |
| 2K | 2 immunisations with inactivated DISC HSV-1 |
| 1L | 1 immunisation with (live) DISC HSV-1 |
| 2L | 2 immunisations with (live) DISC HSV-1 |
| 1S | 1 immunisation with w.t. HSV-1 (strain SC16) |
| 2S | 2 immunisations with w.t. HSV-1 (strain SC16) |

Figure 14:
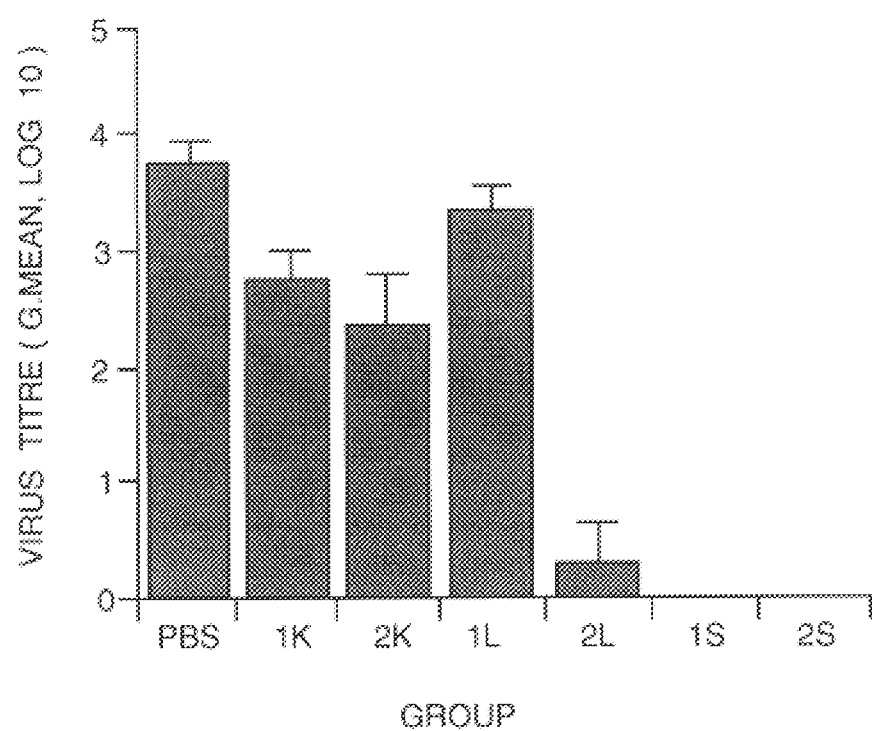
FIG. 14 relates to the long-term protective effect in mice of vaccination with DISC HSV-1 against challenge with w.t. HSV-1 (strain SC16). The graph shows the mean log titre of w.t. HSV-1 in the ears 5 days post challenge and 223 days post vaccination.
Figure 15:
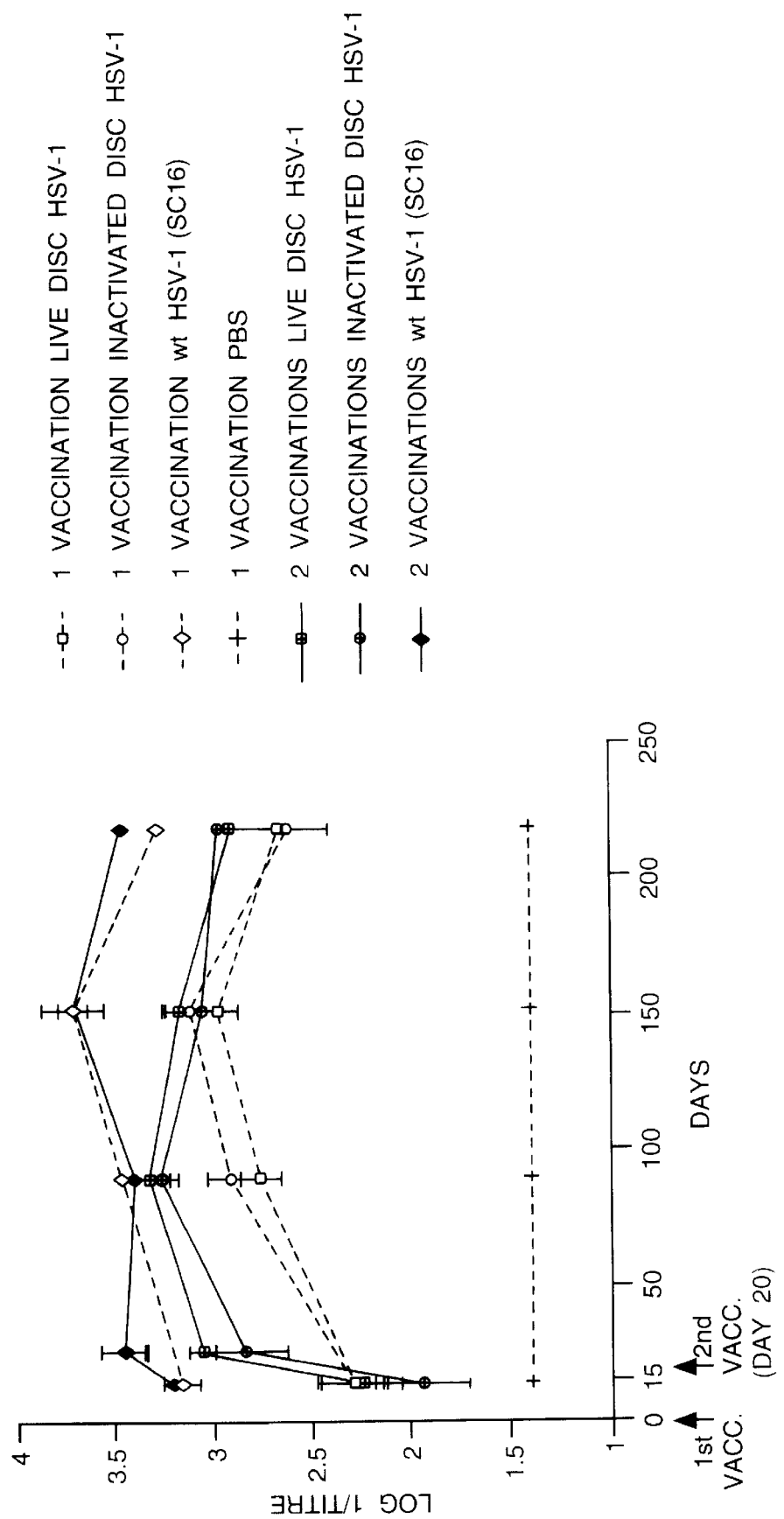
FIG. 15 relates to the long-term protective effect in mice of vaccination with DISC HSV-1 against challenge with w.t. HSV-1 (strain SC16). The graph shows neutralising antibody titres days 15, 27, 90, 152 and 218 post vaccination as stated.

All groups were immunised by scarification of the left ear pinna with $5 \times 10^6$ pfu on day 0 and blood samples taken on days 15, 27, 90, 152 and 218. Groups PBS, 2K, 2L and 2S received additional immunisations of PBS or $5 \times 10^5$ pfu on day 20. All groups were challenged with $5 \times 10^5$ w.t. HSV-1 (strain SC16) on day 223. The amount of virus present in the challenged ear (right) 5 days post challenge was assayed by plaquing on BHK cells. The results as depicted by FIG. 14 show that two vaccinations with DISC HSV-1 (group 2L) provides goods protection compared to inactivated DISC HSV-1 (group 2K), but that better protection was obtained with w.t. HSV-1 (strain SC16). The efficacy of vaccination with w.t. HSV-1 is of course, to be expected. However the use of normal live viruses as vaccines is generally undesirable. FIG. 15 shows the neutralising antibody titres induced by the various vaccinations. This shows that since 2 doses of DISC HSV-1 produce the same titre as two doses of the inactivated DISC HSV-1, the protective effect of DISC HSV-1 cannot be simply explained by antibody induction.

PROPHYLACTIC EFFECT OF DISC HSV-2

The in vivo mouse ear model was used to study the prophylactic effect of DISC HSV-2.

Six week old BALB/c mice were divided into groups. They were immunised by scarification of the left ear pinna as follows.

| Group | Vaccination Material and Dose |
|---|---|
| 1 | $5 \times 10^2$ pfu live DISC HSV-2 |
| 2 | $5 \times 10^3$ pfu live DISC HSV-2 |
| 3 | $5 \times 10^4$ pfu live DISC HSV-2 |
| 4 | $5 \times 10^5$ pfu live DISC HSV-2 |
| 5 | $5 \times 10^2$ pfu killed DISC HSV-2 |
| 6 | $5 \times 10^3$ pfu killed DISC HSV-2 |
| 7 | $5 \times 10^4$ pfu killed DISC HSV-2 |
| 8 | $5 \times 10^5$ pfu killed DISC HSV-2 |
| 9 | $5 \times 10^4$ pfu w.t. HSV-2 (strain HG52) |
| 10 | $5 \times 10^5$ pfu w.t. HSV-2 (strain HG52) |
| 11 | PBS |

The DISC HSV-2 was a gH deletion mutant of strain HG52

Three weeks later, all groups were challenged by scarification of the right ear pinna with $5 \times 10^4$ of w.t. HSV-2 (strain HG52).

Figure 16:
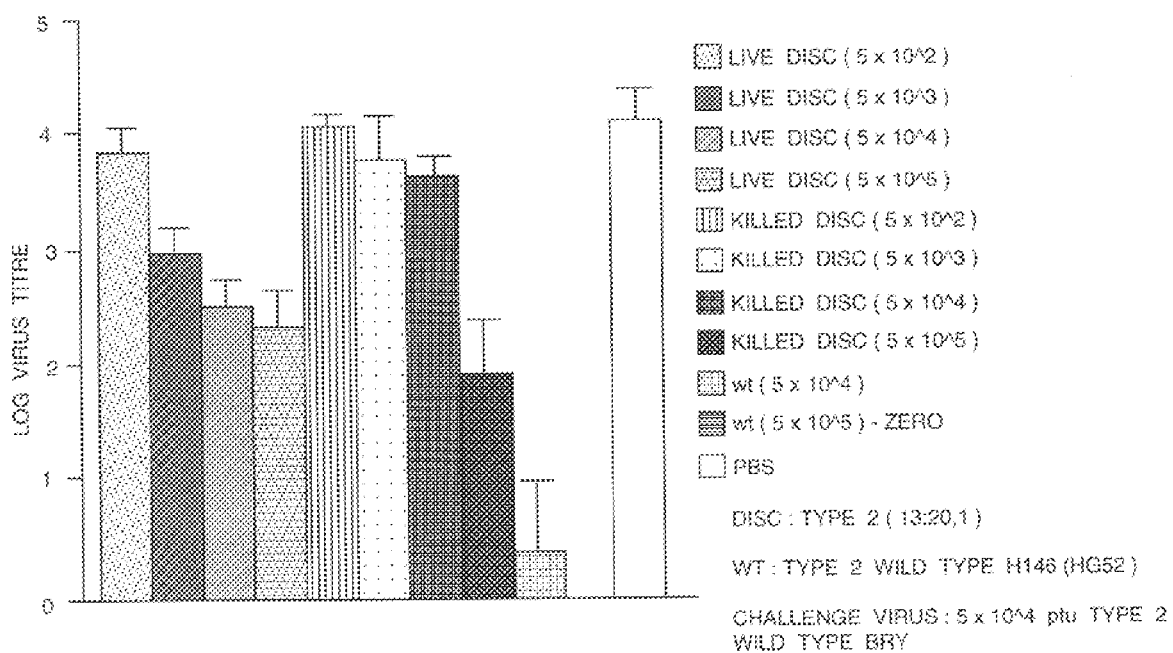
FIG. 16 relates to the protective effect in mice of vaccination with DISC HSV-2 against challenge with w.t. HSV-2 (strain HG52) for vaccinations with live DISC HSV-2, killed DISC HSV-2 and w.t. HSV-2 (strain HG52) at varying doses, the graph shows mean log titre of w.t. HSV-2 in the ear post challenge.
Figure 17:
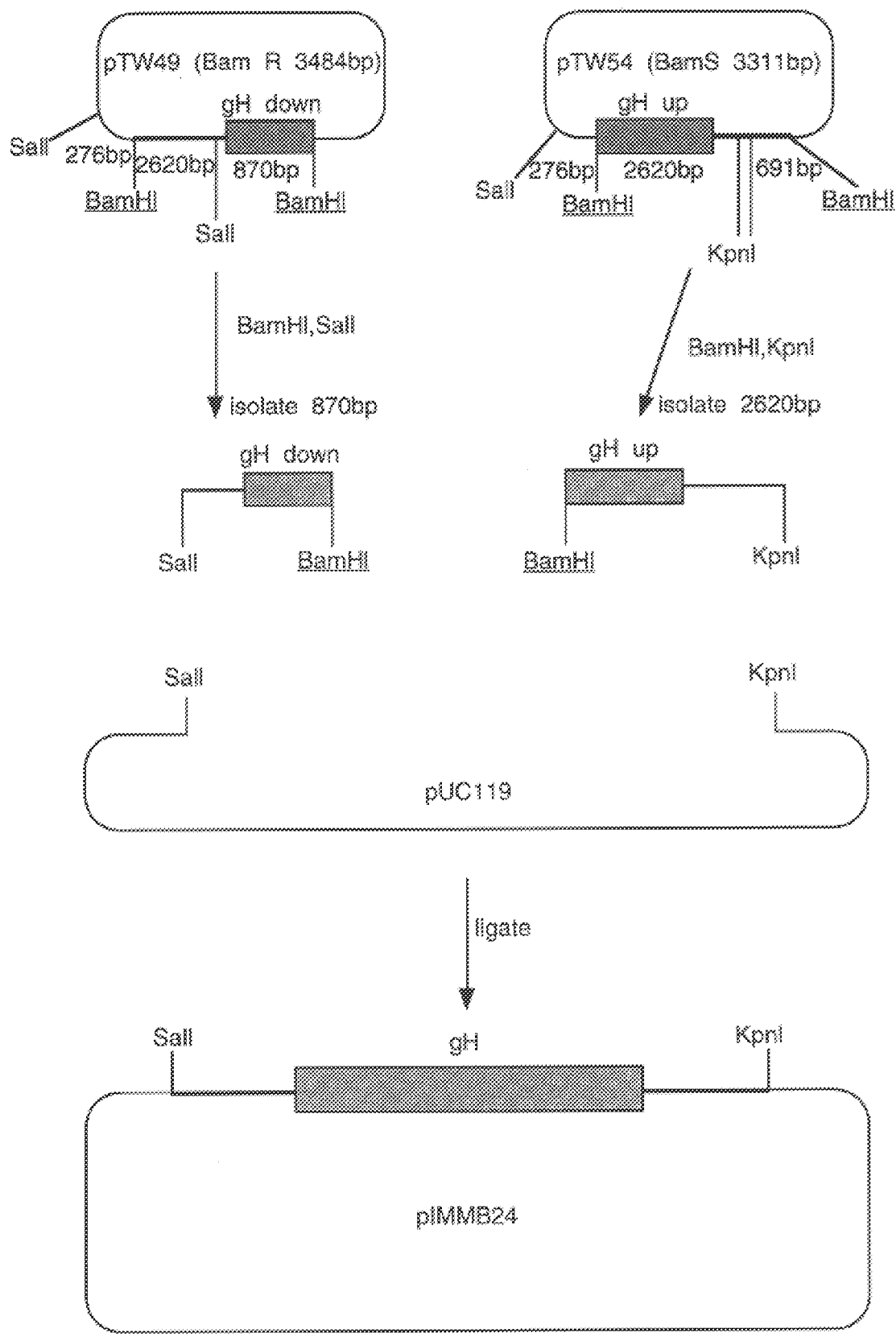
FIG. 17 illustrates the construction of a single plasmid containing the complete HSV-2 gH gene.
Figure 21:
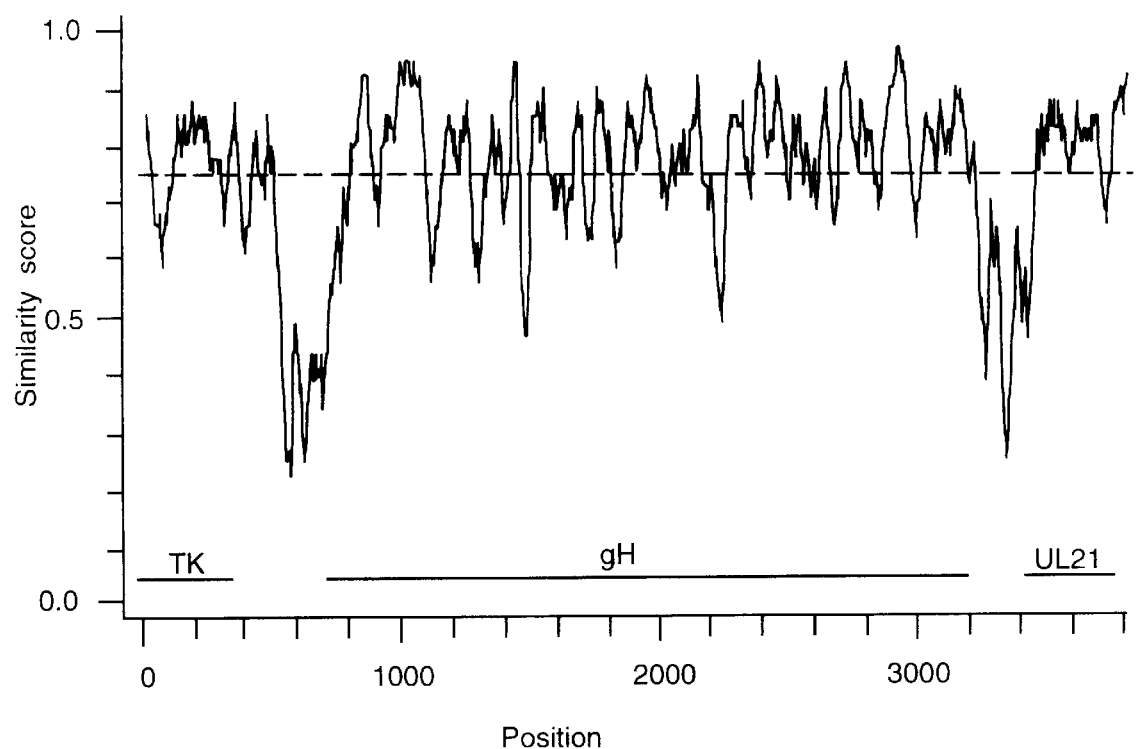
FIG. 21 shows graphically the level of similarity between the DNA sequences of HSV-1 (SEQ ID NO:3) and HSV-2 (SEQ ID NO:1) in the region of the gH gene (from UWGCG program Plotsimilarity).
Figure 22:
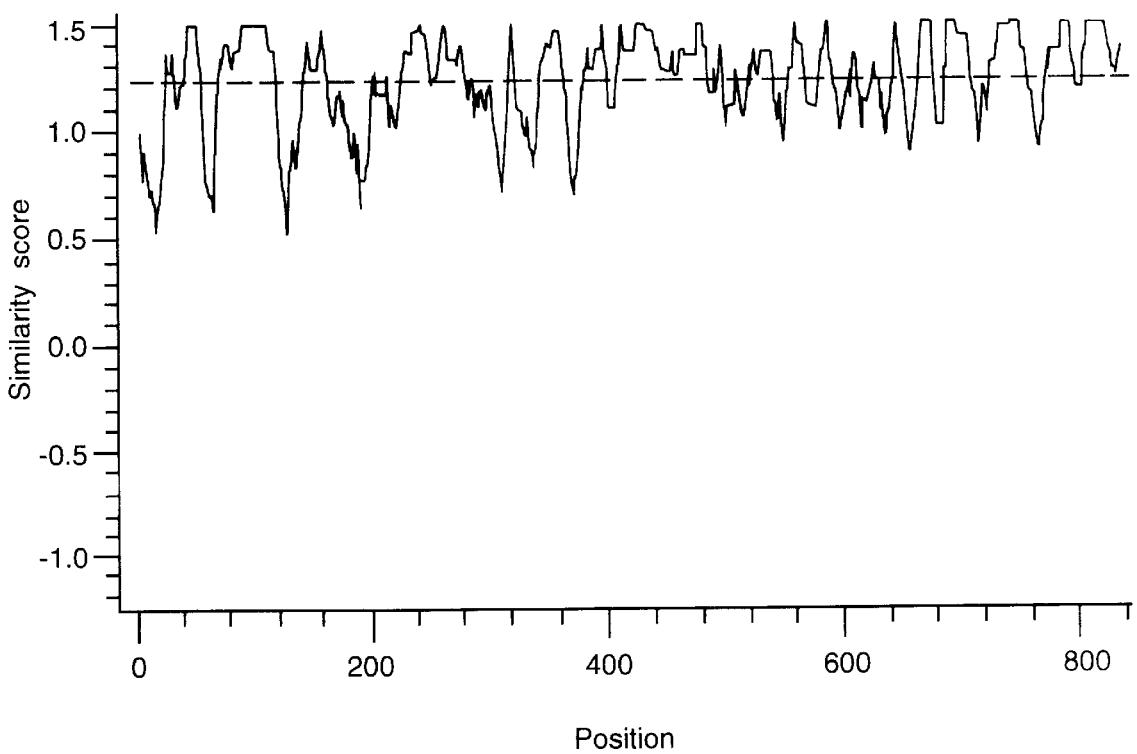
FIG. 22 shows graphically the level of similarity between the amino acid sequences of the HSV-1 (SEQ ID NO:4) and HSV-2 (SEQ ID NO:2) gH proteins (from UWGCG program Plotsimilarity).
Figure 23:
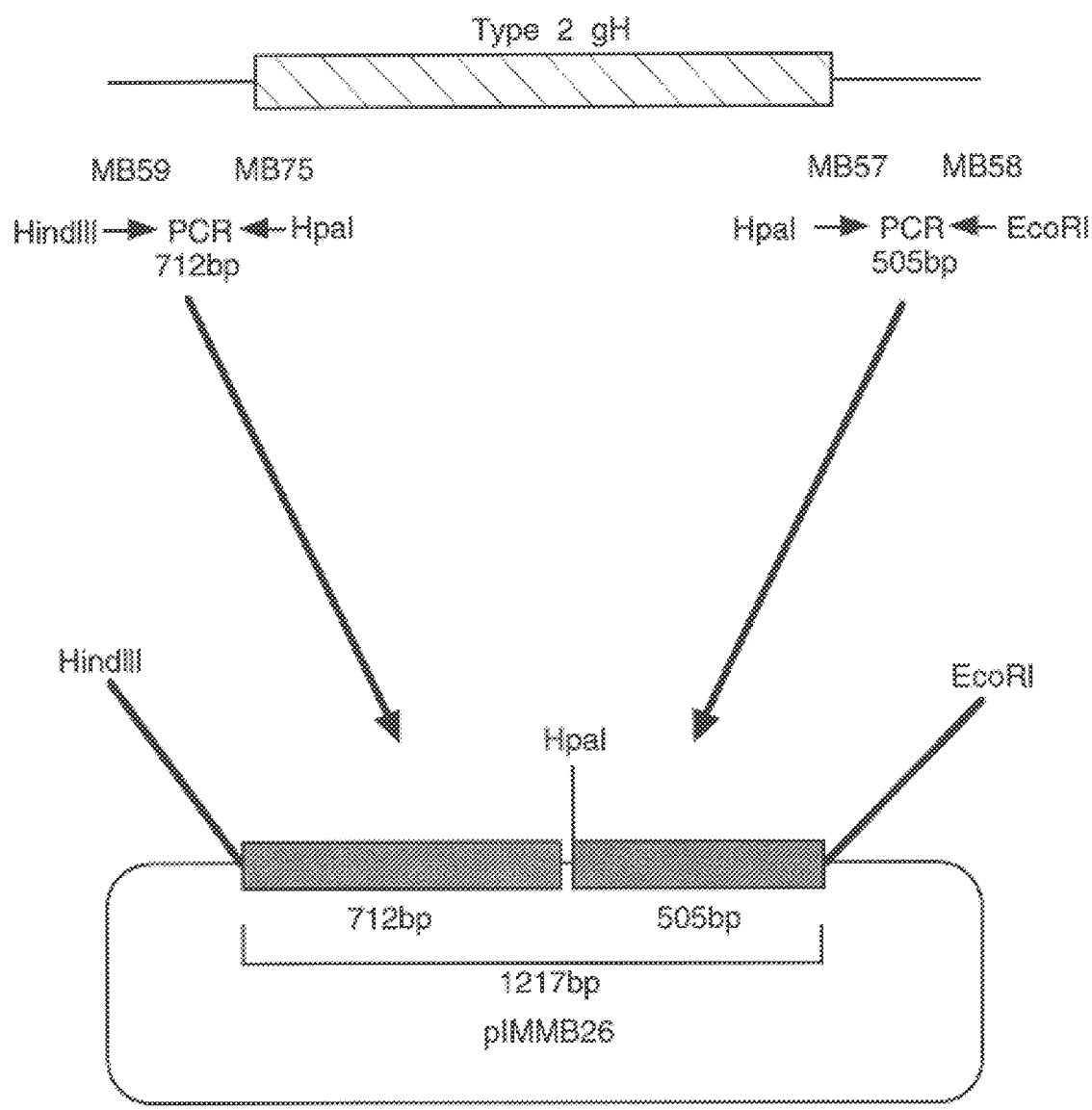
FIG. 23 shows the construction of pIMMB26; two fragments from the left and right sides of the HSV2 gH gene were amplified by PCR and cloned into pUCll9. The four oligonucleotides MB57 (SEQ ID NO:5), MB58 (SEQ ID NO:6), MB59 (SEQ ID NO:7) and MB60 are shown.
Figure 24:
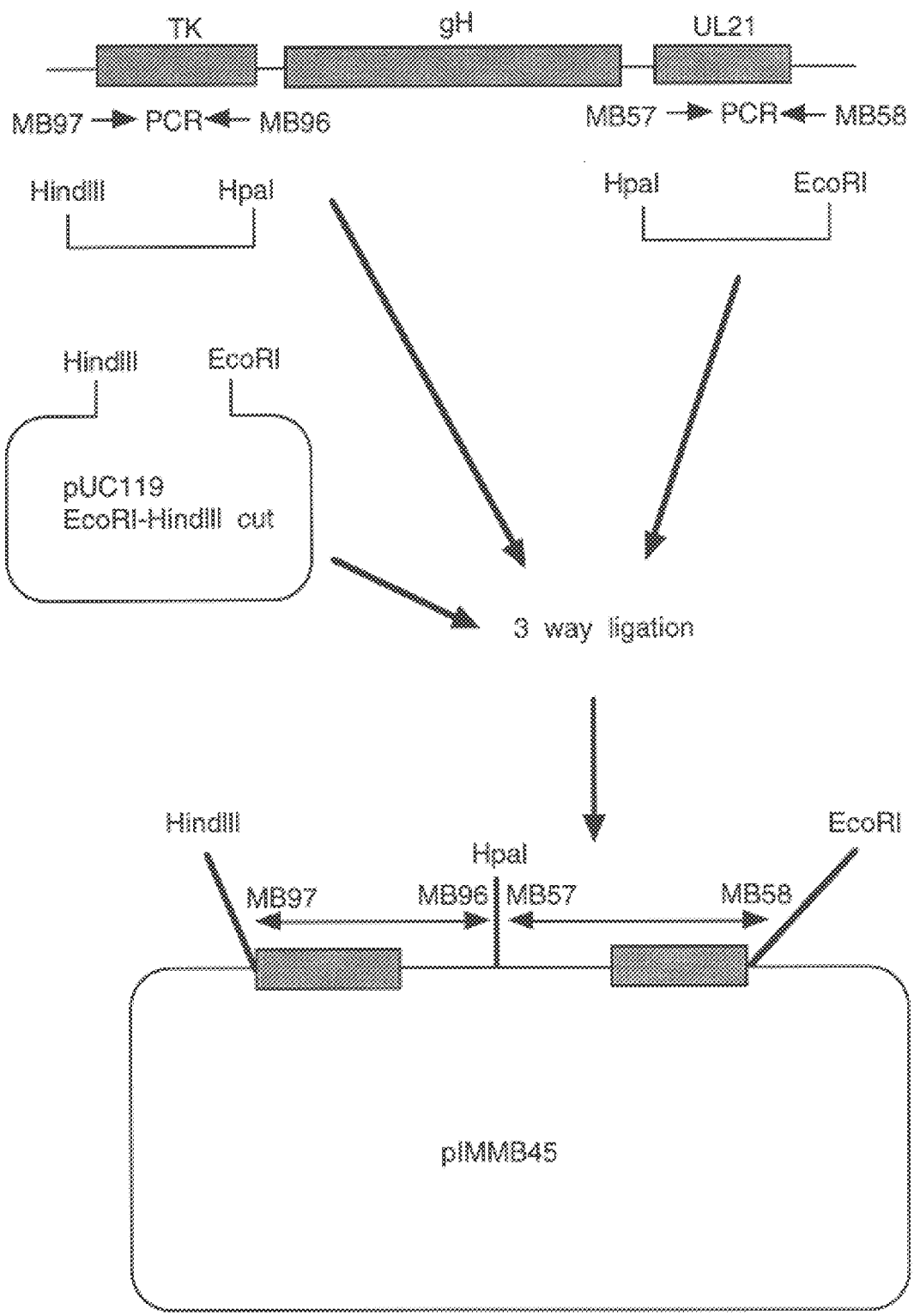
FIG. 24 shows the construction of pIMMB45.
Figure 25:
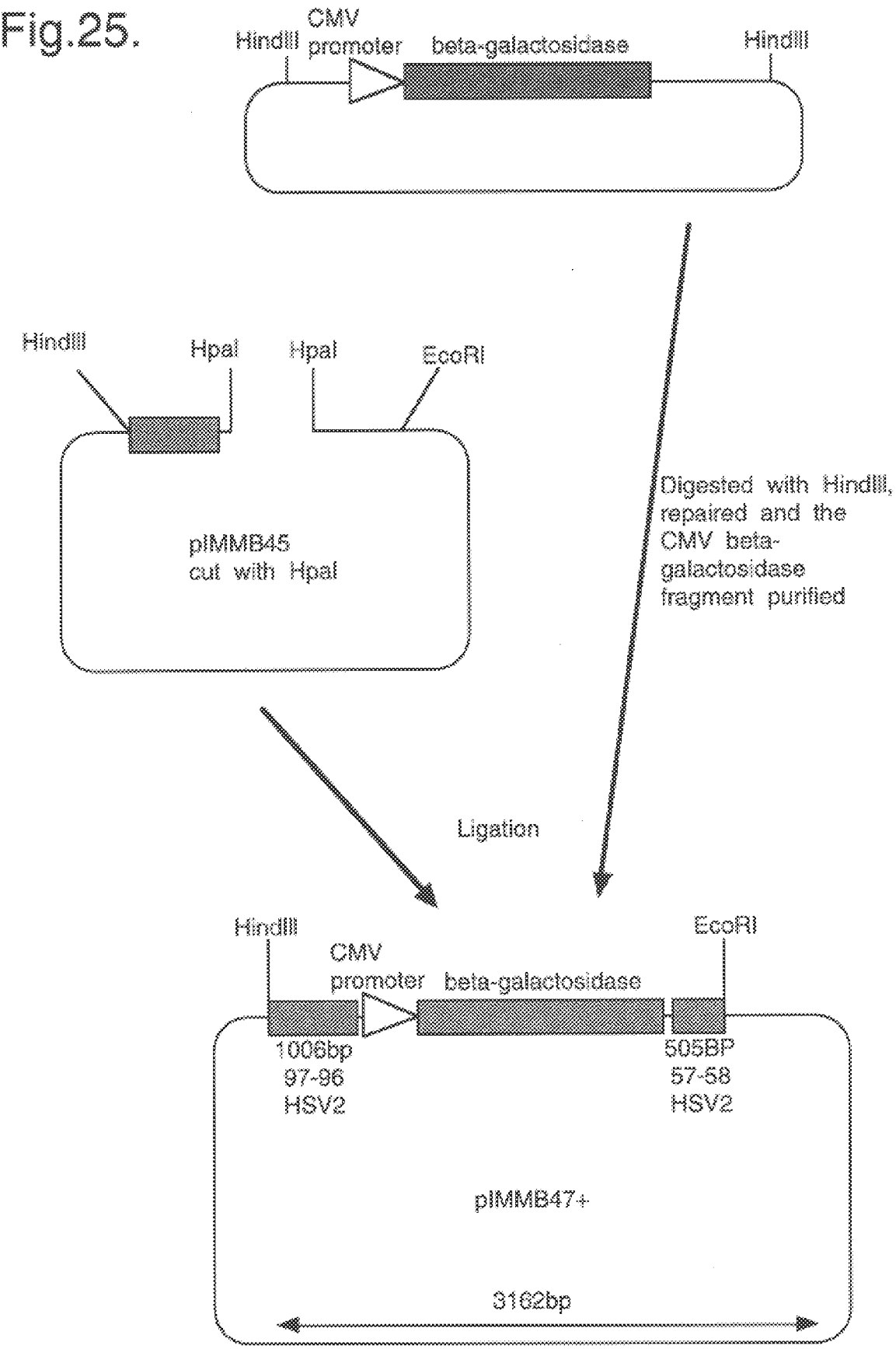
FIG. 25 shows construction of the first stage recombination vector pIMMB47+.
Figure 26:
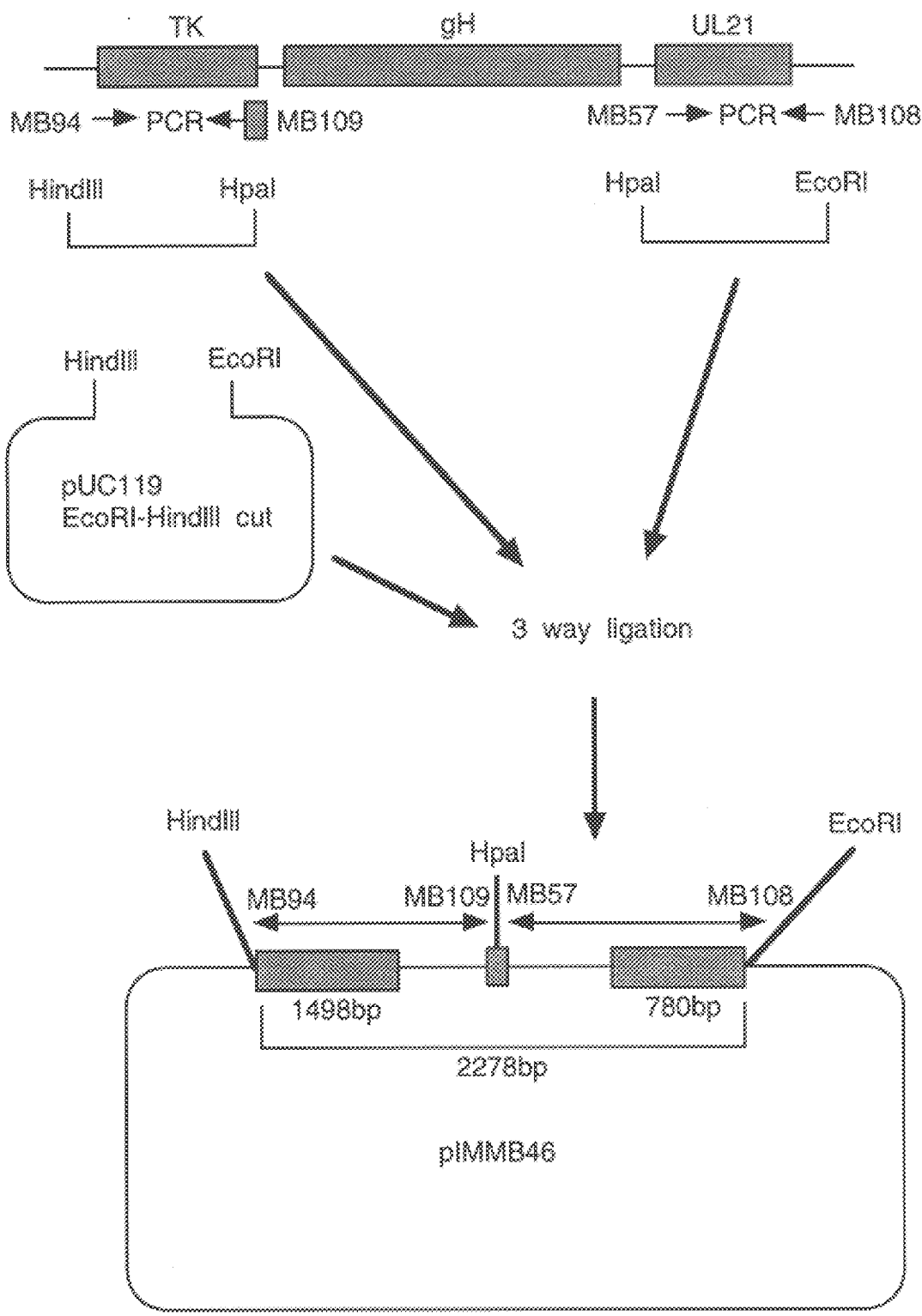
FIG. 26 shows construction of the second stage recombination vector pIMMB46.

The amount of virus present in the challenged ear (right) 5 days post challenge was assayed by plaquing on BKK cells (see FIG. 16). The results as depicted by the figure show that vaccination with DISC HSV-2 at doses of $5 \times 10^3$, $5 \times 10^4$ and $5 \times 10^5$ pfu provides good protection against challenge with w.t. HSV-2 (strain HG52) compared to killed DISC HSV-2. However and as is to be expected, better protection was obtained with w.t. HSV-2 at doses of $5 \times 10^4$ and $5 \times 10^5$ pfu, but the use of normal live wild type viruses as vaccines is undesirable.

IN VIVO GUINEA PIG STUDIES

As mentioned earlier, HSV-2 appears to be closely associated with genital lesions. The guinea pig currently provides the best animal model for primary and recurrent genital disease in humans (Stanberry, L. R. et al. J. Inf. Dis. 1982, 146, 397–404).

Therefore the applicants have extended the earlier described mouse studies to the guinea pig vaginal model of HSV-2 infection which provides a useful system to assess the immunogenicity of candidate vaccines against genital HSV-2 infection in humans. It permits a comprehensive assessment of primary clinical symptoms following intravaginal challenge with HSV-2, and also analysis of the frequency of subsequent recurrences.

(1) Groups of 14 animals were immunised with two doses of the DISC HSV-1 vaccine ($2 \times 10^7$ pfu, 3 weeks apart) either by non-traumatic introduction into the vagina (intravaginal route), or by scarification of the ear pinna (intra-epithelial route). A control group of 21 animals was vaccinated intra-vaginally with a mock virus preparation and a further group of 14 animals was vaccinated intra-epithelially with two equivalent doses of β-propiolactone-inactivated w.t. HSV-1.

Vaccinated animals were challenged 3 weeks later with $10^{5.2}$ pfu w.t. HSV-2 virus (strain MS) and monitored for the symptoms of primary and recurrent disease.

Figure 6:
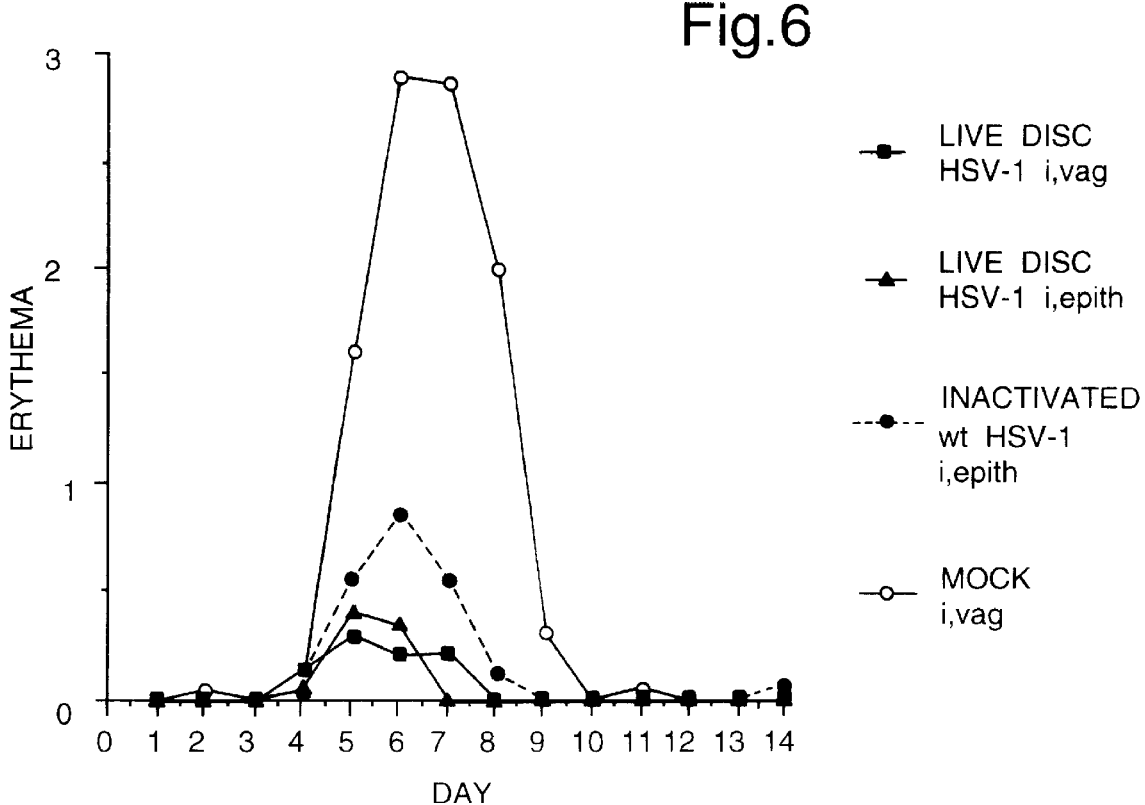
FIG. 6 shows clinical symptoms as assessed by erythema score in guinea-pigs post challenge with $10^{5.2}$ pfu w.t. HSV-2 (strain MS) subsequent to vaccination with doses of $2 \times 10^7$ pfu DISC HSV-1 at a 3 week interval either by the intra-epithelial or the intra-vaginal route.
Figure 7:
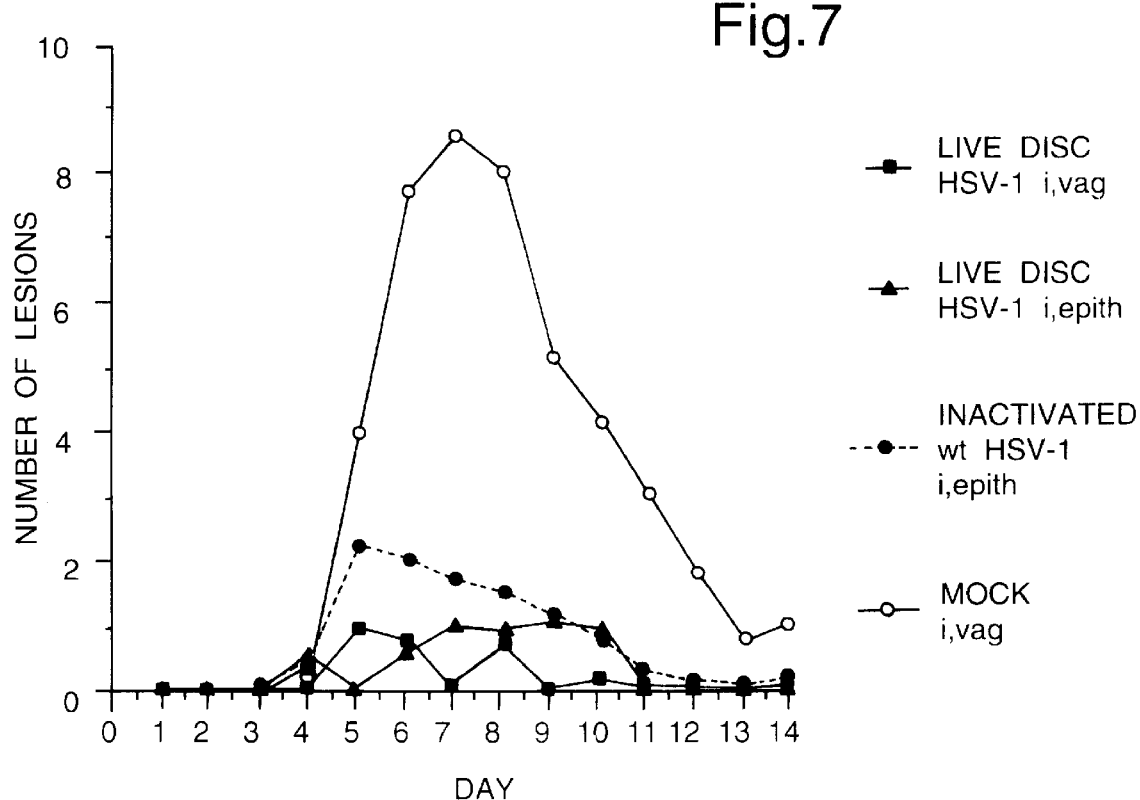
FIG. 7 shows clinical symptoms as assessed by total lesion score in guinea-pigs post challenge with $10^{5.2}$ pfu w.t. HSV-2 (strain MS) subsequent to vaccination with doses of $2 \times 10^7$ pfu DISC HSV-1 at a 3 week interval either by the intra-epithelial or the intra-vaginal route.

(a) Following w.t. HSV-2 challenge, animals were assessed daily over a two week period for symptoms of primary infection. Clinical lesions were scored as a direct numerical value, and erythema was scored on a scale of 1–5. The vaginal area was also measured as an index of oedema (data not shown). The results are shown in FIGS. 6 and 7. Points on the graphs represent mean erythema score per animal per day (FIG. 6) and mean total lesion score per day per animal (FIG. 7).

The results show that intra-epithelial and intra-vaginal vaccination with the DISC HSV-1 both provided a high degree of protection against the primary symptoms of HSV-2 infection. Surprisingly, inactivated HSV-1 administered by the intra-epithelial route also provided substantial protection, though apparently less than that afforded by the DISC virus vaccine.

Figure 8:
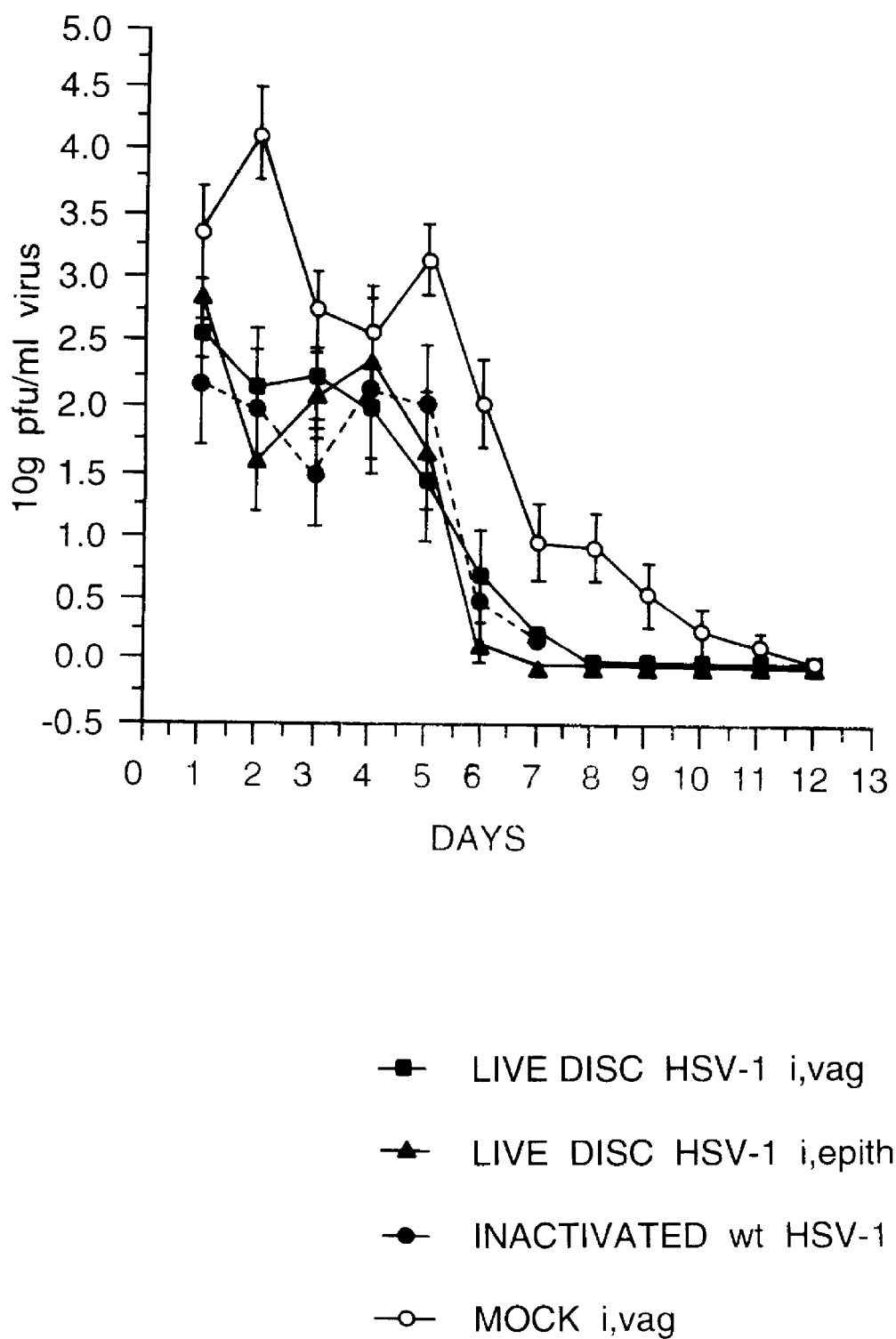
FIG. 8 shows post challenge virus w.t. HSV-2 (strain MS) replication in guinea-pigs post challenge with $10^{5.2}$ pfu w.t. HSV-2 (strain MS) subsequent to vaccination with doses of $2 \times 10^7$ pfu DISC HSV-1 at a 3 week interval either by the intra-epithelial or the intra-vaginal route.

(b) Daily vaginal swabs were taken from all animals over a 12 day period post-challenge and virus titres determined by plaquing on Vero cells in order to monitor growth of the challenge virus in the vagina. The results as depicted in FIG. 8 shows that infection virus titres in mock-vaccinated animals rose to a maximum of $3 \times 10^4$ at day 2 post challenge, and could be detected until day 10. By contrast, virus titres in the vaccinated animals declined steadily from day 1, and were undetectable by day 7. No significant different was observed between the groups immunised with the DISC HSV-1 or the inactivated virus preparation.

Figure 9A:
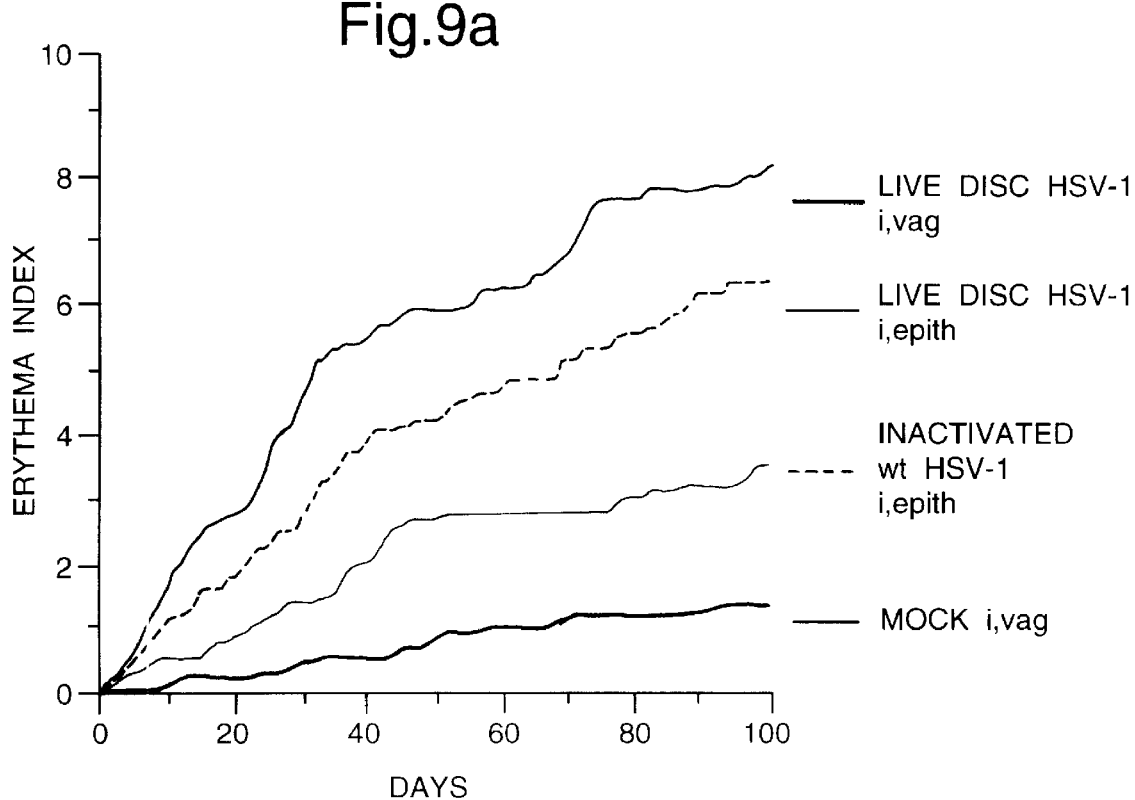
FIGS. 9a and 9b show recurrent disease in guinea-pigs post challenge with $10^{5.2}$ pfu w.t. HSV-2 (strain MS) subsequent to vaccination with doses of $2 \times 10^7$ pfu DISC HSV-1 at a 3 week interval by the intra-epithelial or the intra-vaginal route.
Figure 9B:
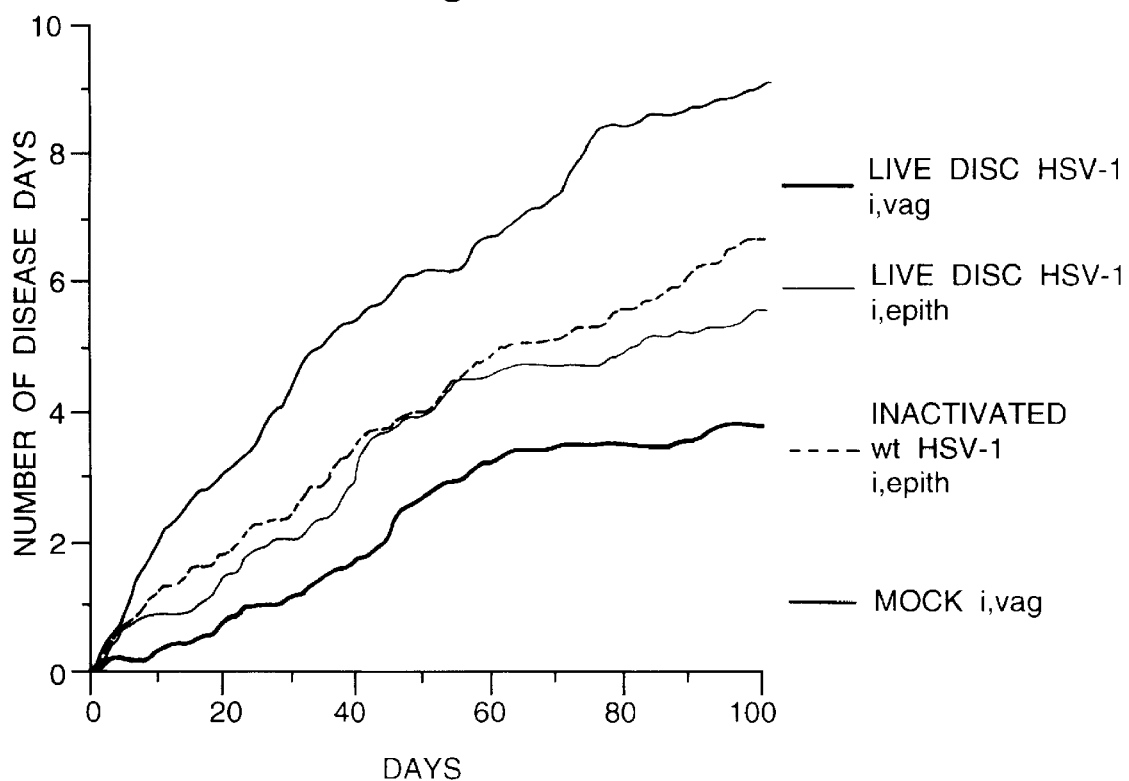

(c) Following HSV-2 challenge, animals which had fully recovered from the acute phase of disease by 28 days were monitored daily for a further 100 days for the recurrence of disease. Numbers of animals in each group were: DISC/Intra-vaginal -14; DISC/Intra-epithelial -12; Inactivated/Intra-epithelial -14; Mock/Intra-vaginal -12. Clinical lesions were scored as a direct numerical value, and erythema was scored on a scale of 1–5. The results are shown in FIGS. 9a and 9b. Points on the graphs represent the cumulative totals of mean values per day per animal.

The results show that animals vaccinated with the DISC HSV-1 by the Intra-vaginal route showed approximately a 50% reduction in the number of recurrent HSV-2 lesions occurring over the 100 day follow-up period. Intra-epithelial vaccination with DISC HSV-1 and inactivated virus also resulted in a reduction of recurrent lesions, but to a lesser extent.

(2) The following experiment was also designed to assess the immunogenicity of candidate DISC vaccines based on HSV-1 against genital HSV-2 infection. The experiment was designed to compare different vaccination routes (per vaginum, oral and nasal ie different mucosal surfaces) and different doses of either DISC HSV-1 or inactivated HSV-1 in the guinea pig.

MATERIALS AND METHODS

Virus.

(i) DISC HSV-1 was propagated on Vero cells (F6) which had been transfected with the HSV-1 gH gene as described previously in w092/05263 published on 2 Apr. 1992. Briefly, confluent monolayers of F6 cells were infected with DISC HSV-1 at a multiplicity of 0.1 pfu per cell and harvested when 90–100% cpe was observed. Cells were harvested with a cell scraper, pelleted by centrifugation and the pellet resuspended in a small volume of Eagles Minimum Essential. Medium (EMEM). The suspension was sonicated for 1 minute and stored in aliquots at −70° C. Virus titres were determined on F6 cells.

(ii) DISC HSV-1 was inactivated by the addition of β-propiolactone at a concentration of 0.05% for one hour at room temperature. Inactivation was checked by adding the virus to F6 cells.

(iii) HSV-2 strain MS was propagated and titred on Vero cells in the same manner as DISC HSV-1 as described above. Animals Female Dunkin-Hartley guinea-pigs (300–350 g) were obtained from Davis Hall, Darley Oaks Farms, Newchurch, Nr. Burton-on-Trent.

EXPERIMENTAL DESIGN

Groups of 12 animals were immunised with two doses of $8 \times 10^6$ pfu DISC HSV-1 or with equivalent doses of inactivated DISC HSV-1, on days 1 and 17 of the experiment. Immunisation was performed with either 0.05 ml of virus intravaginally, with 0.2 ml of virus intranasally or with 0.2 ml virus orally. A control group of 12 animals was vaccinated intravaginally with a mock preparation of virus consisting of sonicated Vero cells. All groups were challenged intravaginally on day 34 with $10^{5.2}$ pfu HSV-2 (strain MS) and the experiment blinded by randomisation of the cages by an independent worker. For a period of 11 days following challenge, animals were monitored for the symptoms of primary disease. Clinical observations were scored as the number of lesions present in the vaginal area and the presence of erythema (scored on a scale of 1–5). In addition, daily vaginal swabs were taken from all animals over a 12 day period post challenge and virus titres were determined by plaquing on Vero cells in order to monitor growth of the challenge virus in the vagina. Statistical methods Differences in group clinical scores were tested for significance using the Mann-Whitney U test. Values of $p < 0.1$ were considered significant.

RESULTS

Clinical disease profile.

Figure 10A:
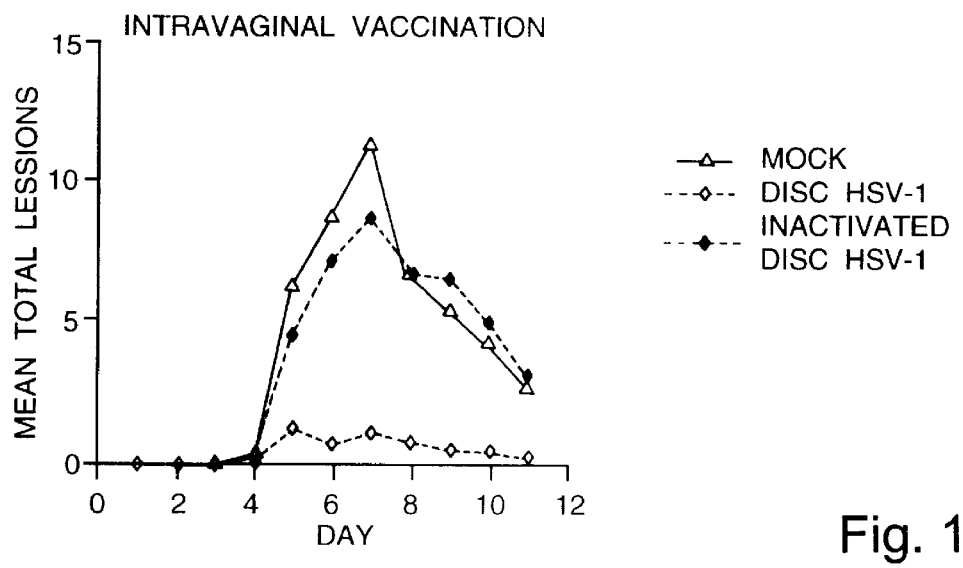
FIG. 10 shows mean lesion score per animal (guinea-pigs) with w.t. HSV-2 (strain MS) infection and which have been vaccinated via the vaginal, oral or nasal routes with a mock virus preparation, DISC RSV-1 or inactivated DISC HSV-1.
Figure 10B:
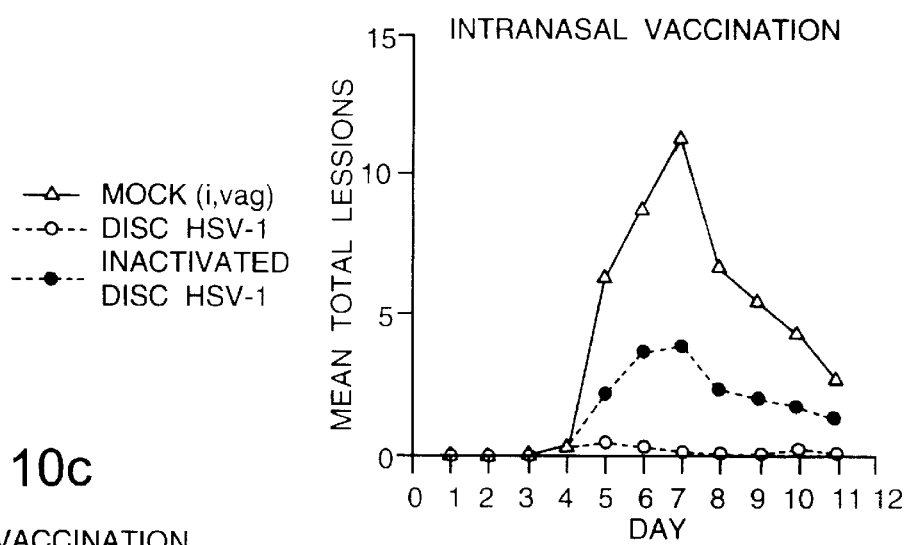
Figure 10C:
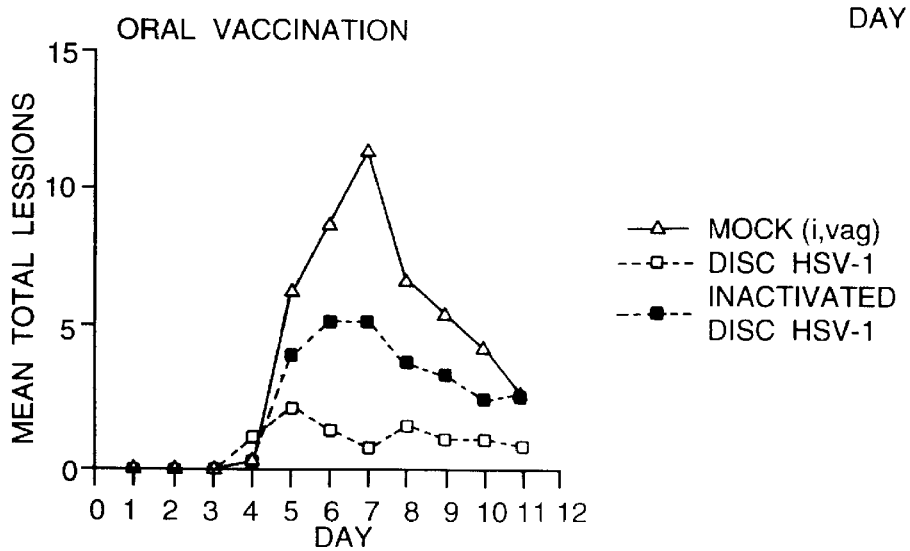
Figure 11A:
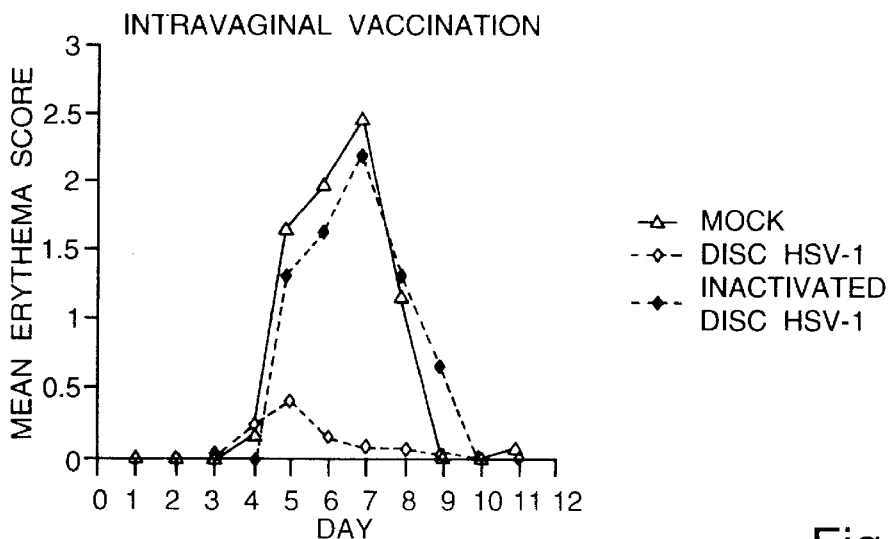
FIG. 11 shows mean erythema score per animal (guinea-pigs) with w.t. HSV-2 (strain MS) infection and which have been vaccinated via tho vaginal, oral or nasal routes with a mock virus preparation, DISC HSV-1 or inactivated DISC HSV-1.
Figure 11B:
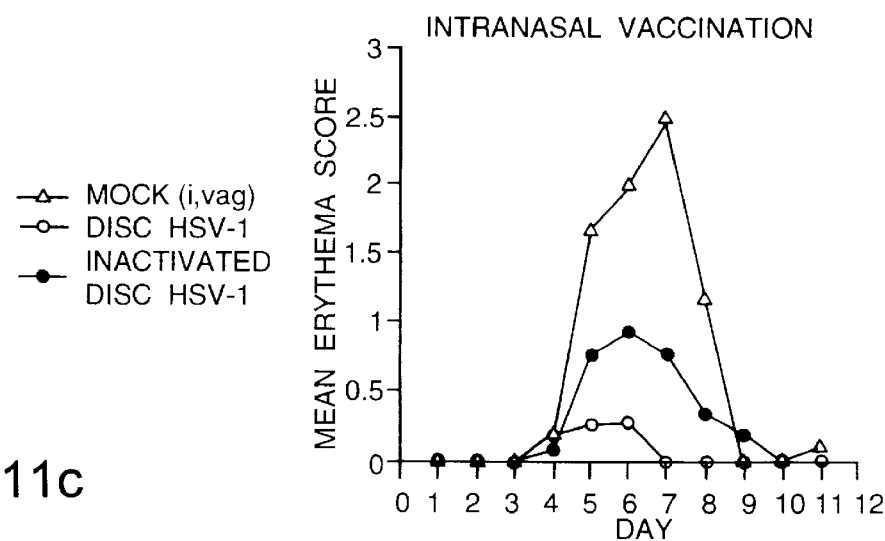
Figure 11C:
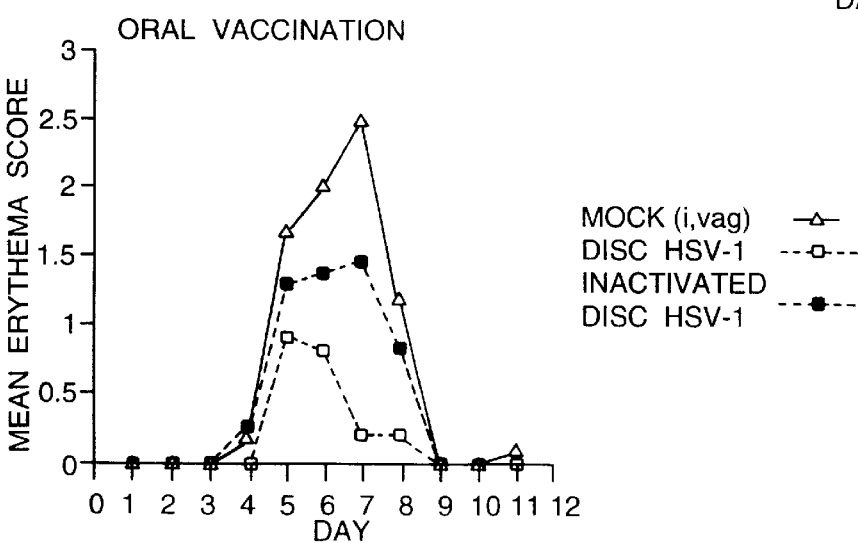

The mean lesion score per animal, the mean erythema score and the effect of vaccination on post challenge virus replication for each of the immunisation groups are shown in FIGS. 10, 11 and 12 respectively. As compared to mock vaccinated animals, vaccination with DISC HSV-1 by the intravaginal route provided a high degree of protection from primary symptoms of infection. In contrast, vaccination with inactivated DISC HSV-1 at an equivalent dose did not lead to any significant protection.

Intranasal immunisation with DISC HSV-1 resulted in an even higher degree of protection than intravaginal vaccination. This was particularly apparent when looking at the number of days with severe disease, as defined by a lesion score of 6 or more (see table 2). Inactivated DISC HSV-1 gave some protection via the intranasal route, but It was not as effective as vaccination with DISC HSV-1.

Vaccination via the oral route also led to protection, but to a lesser degree than intranasal or intravaginal vaccination. Again vaccination with DISC HSV-1 virus protected more efficiently than vaccination with inactivated DISC HSV-1.

TABLE 2

INCIDENCE OF PRIMARY DISEASE SYMPTOMS

| Immunisation with | Any disease symptoms (% of animals) | Lesion score >5 (% of animals) | Duration of disease (mean no. days) | Disease ongoing on day 11 (% of animals) |
|---|---|---|---|---|
| mock | 92 | 75 | 6.8 | 75 |
| DISC HSV-1 i.vag | 33 | 17 | 4.5 | 8 |
| HSV-1 inactivated i.vag | 92 | 67 | 6.2 | 83 |
| DISC HSV-1 i.nas | 33 | 0 | 2.3 | 0 |
| HSV-1 inactivated i.nas | 67 | 17 | 6.3 | 42 |
| DISC HSV-1 oral | 90 | 20 | 4.1 | 20 |
| HSV-1 inactivated oral | 91 | 36 | 5.8 | 64 |

Thus the following conclusions can be drawn from this experiment with the in vivo guinea pig model.

A. Vaccination with DISC HSV-1 via the intravaginal and intranasal routes led to a high degree of protection from acute disease symptoms following a challenge with HSV-2.

B. Intranasal administration of DISC HSV-1 gave the highest degree of protection when considering the number of days of severe disease (as defined by the presence of 6 or more lesions).

C. Intravaginal vaccination with inactivated virus resulted in clinical disease symptoms similar to those observed in mock-infected guinea-pigs. Intranasal vaccination with inactivated DISC HSV-1 gave a significant degree of protection, but not as high as DISC HSV-1 vaccination via this route.

D. A significant difference was observed between disease symptoms in animals vaccinated orally with DISC HSV-1 and mock-infected animals. However, this degree of protection was less than that observed in animals vaccinated with DISC HSV-1 via the intranasal or intravaginal route.

E. Symptoms in animals vaccinated orally with inactivated DISC HSV-1 were not significantly different from those in the mock-infected group.

F. The data on shed virus is interesting. Surprisingly the per vaginum vaccination route resulted in significantly lower levels of recovered virus following the challenge dose. This may be due to local antibody production.

(3) The following experiment was designed to investigate HSV-2 induced recurrent disease following therapeutic vaccination.

This was of interest as it has previously been shown that therapeutic administration of certain recombinant HSV-2 antigens, together with adjuvant, can decrease the frequency of subsequent recurrences. (Stanberry, L. R. et al. J. Inf. Dis. 1988; 157, p156–163; Stanberry, L. R. et al. J. Gen. Virol. 1989a; 70 p3177–3185; Ho, R. J. Y. et al, J. Virol. 1989; 63p 2951–2958).

Figure 13:
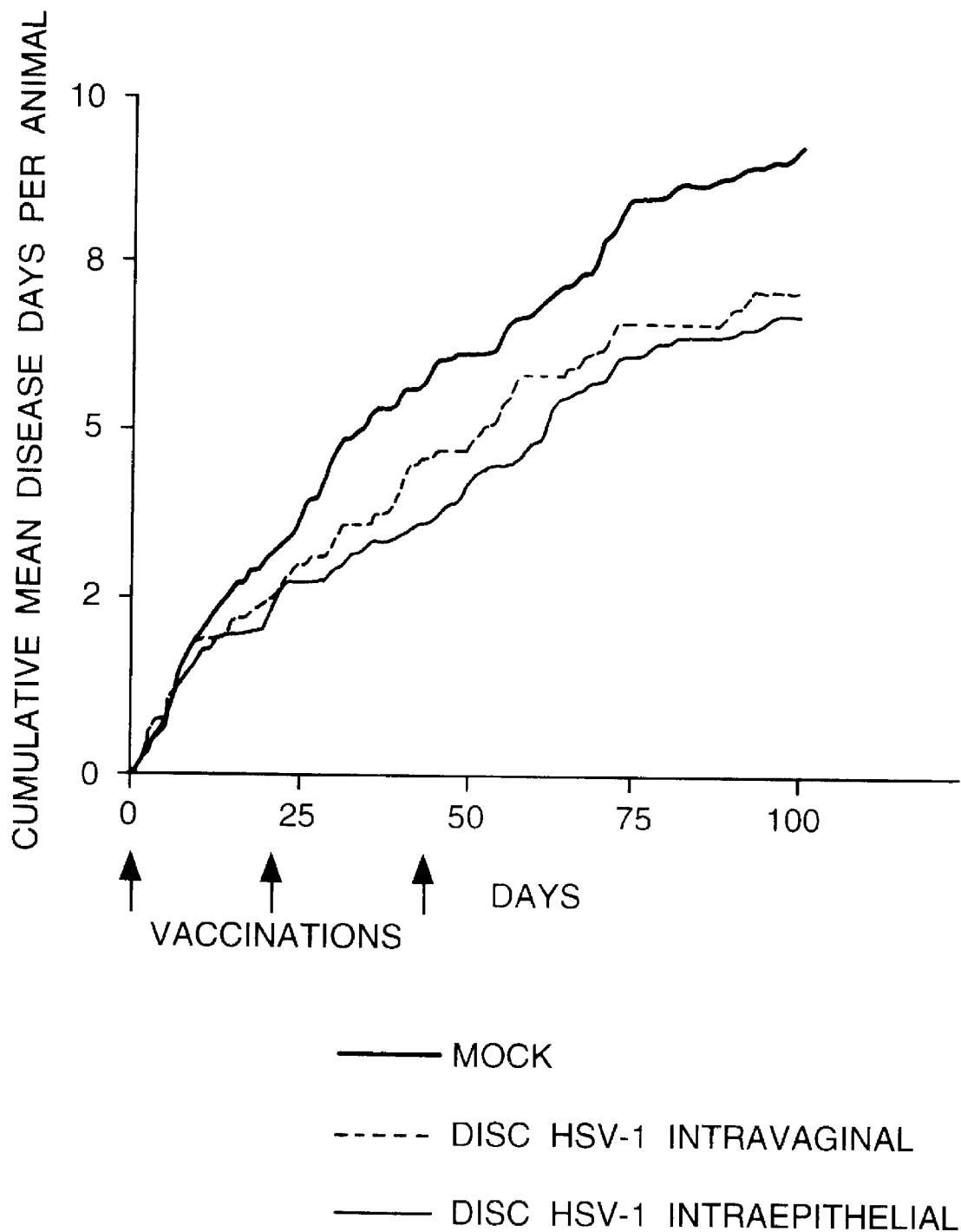
FIG. 13 shows recurrent disease following therapeutic vaccination. This is shown as cumulative number of days on which disease was observed (disease/days) in groups of guinea-pigs vaccinated with DISC HSV-1 either intra-epithelially or intra-vaginally or with a mock virus preparation intra-vaginally after challenge with w.t. HSV-2 (strain MS). Disease was classified as either presence of one or more lesions or an erythema score of 1 or more. Animals were monitored from 4 weeks after initial challenge with w.t. HSV-2 (strain MS) (day 0) for 100 days. Animals were vaccinated at Day 0, Day 24 and Day 44 with $2 \times 10^7$ pfu or equivalent dose as indicated.

Accordingly 21 animals which had recovered fully from primary HSV-2 disease four weeks after challenge were randomised into three groups, and treated with live DISC HSV-1 intravaginally (10 animals), or intra-epithelially (11 animals). A group of 12 animals, which had previously acted as controls for prophylactic vaccination (see (2) above) and which had also recovered fully from primary disease were treated with an equivalent mock preparation (12 animals). The animals were given further identical treatments 24 and 48 days later. The frequency of recurrent disease was monitored from the day of first treatment for a further 100 days, and the cumulative results are shown in FIG. 13 and summarised in Table 3 below.

TABLE 3

Effect of therapeutic vaccination on recurrent disease

| | Mock | | DISC HSV-1 Intra-epithelial | | DISC HSV-1 Intra-vaginal | |
|---|---|---|---|---|---|---|
| | Total | % of Mock | Total | % of Mock | Total | % of Mock |
| 1 Mean total disease/days per animal | 9.41 | 100 | 6.90 | 73 | 7.32 | 78 |
| 2 Mean total episodes per animal | 6.27 | 100 | 4.67 | 74 | 5.10 | 81 |
| 3 Disease incidence | 12/12 | 100 | 9/11 | 82 | 10/10 | 100 |
| 4 Severity per episode | 3.21 | 100 | 3.00 | 93 | 2.86 | 89 |
| Mean duration of episode (days) | 1.49 | | 1.27 | | 1.38 | |

1 Total number of days where disease was observed (either lesions or erythema) over the whole observation period (100 days from 1 month after challenge with HSV-2)
2 Total of days disease episodes over the whole observation period (episode length defined as period between two consecutive disease-free days
3 Proportion of animals showing any lesion or erythema score during whole observation period
4 Total sum of erythema scores and lesion numbers over the whole observation period divided by number of episodes observed It can be seen that each of the groups treated with DISC HSV-1 appeared to experience a modest reduction (about 25%) in the overall number of disease/days and episodes especially over the 50 day period following second vaccination.

Sera were collected from these animals at the end of the 100 day observation period. The ELISA and NT antibody titres in the sera were riot significantly higher than those recorded post-challenge but before therapeutic treatment and there were no significant differences in titres between the mock-treatment group and the DISC HSV-1 treated groups.

Thus therapeutic administration of DISC HSV-1 virus either intra-vaginally or intra-epithelially resulted in an apparent reduction (20–25%) in the frequency of recurrence compared with mock-treated animals.

(4) The following experiment was designed to investigate the therapeutic value of a DISC virus based on HSV-2. A DISC HSV-2 (strain HG 52) having a deletion of the gH gene was made as described earlier and in accordance with the general teaching of WO92/05263 published on 2 Apr. 1992 and corresponding to U.S. Pat. No. 5,665,362 issued Sep. 9, 1997, incorporated herein by reference and also using standard procedures in the art. The DISC version of the strain was grown in Vero cells transfected with the HSV-2 gH gene also in accordance with the teaching of WO92/05263.

The experiment was a head to head comparison of DISC HSV-1 with DISC HSV-2 in female 350–400 gms guinea-pigs. Guinea-pigs were divided into three groups. All guinea-pigs were infected with $10^{5.8}$ pfu HSV-2 strain MS. Four weeks were then allowed for the primary disease to have both developed and resolved and for recurrences to have started. The animals were then treated. A first group of 15 animals was treated intravaginally with a mock preparation of virus consisting of sonicated Vero cells. A second group of 13 animals was treated Intravaginally with $10^7$ pfu DISC HSV-1. A third group of 14 animals was treated intravaginally with $10^7$ pfu DISC HSV-2. Treatment was repeated in 14 days.

The results are shown in Table 4. Days 1–13 covers the period between the two treatments. Days 14–27 covers the two week period subsequent to the second treatment. Days 1–27 covers the complete period.

As shown by the results, it appears that treatment with DISC HSV-2 was effective in alleviating symptoms caused by infection with HSV-2 strain MS. Treatment with DISC HSV-2 was more effective than treatment with DISC HSV-1.

TABLE 4

| Group | Erythema scores | | | Lesions scores | | | Disease Days | | |
|---|---|---|---|---|---|---|---|---|---|
| | Total | Per animal | % of Mock | Total | Per animal | % of Mock | Total | Per animal | % of Mock |
| Days 1–13 | | | | | | | | | |
| Mock | 38 | 2.53 | 100 | 66 | 4.40 | 100 | 42 | 2.80 | 100 |
| DISC HSV-1 | 34 | 2.62 | 103 | 48 | 3.69 | 84 | 34 | 2.62 | 93 |
| DISC HSV-2 | 22 | 1.57 | 62 | 40 | 2.86 | 65 | 26 | 1.86 | 66 |
| Days 14–27 | | | | | | | | | |
| Mock | 13 | 0.87 | 100 | 23 | 1.53 | 100 | 17 | 1.13 | 100 |
| DISC HSV-1 | 9 | 0.69 | 80 | 14 | 1.08 | 70 | 11 | 0.85 | 75 |
| DISC HSV-2 | 2 | 0.14 | 16 | 3 | 0.21 | 14 | 3 | 0.21 | 19 |
| Days 1–27 | | | | | | | | | |
| Mock | 51 | 3.40 | 100 | 89 | 5.93 | 100 | 59 | 3.93 | 100 |
| DISC HSV-1 | 43 | 3.31 | 97 | 62 | 4.77 | 80 | 45 | 3.46 | 88 |
| DISC HSV-2 | 24 | 1.71 | 50 | 43 | 3.07 | 52 | 29 | 2.07 | 53 |

We claim:

1. A pharmaceutical which comprises an infectious virus, said infectious virus in said pharmaceutical consisting essentially of an effective immunizing amount of a mutant herpesvirus which has an inactivating mutation in a viral gene, said viral gene being essential for the production of infectious new virus particles, wherein said mutant herpesvirus is able to cause production of infectious new virus particles in a recombinant complementing host cell expressing a gene which complements said essential viral gene, but is unable to cause production of infectious new virus particles when said mutant virus infects a host cell other than said recombinant complementing host cell, for prophylactic or therapeutic use in generating an immune response in a subject infected therewith.

2. A pharmaceutical according to claim 1, wherein said essential gene encodes a protein involved in a post-replicative event.

3. A pharmaceutical according to claim 2, wherein said essential gene encodes a protein that is not required for virus assembly, but is necessary for the assembled virus to be able to infect new cells.

4. A pharmaceutical according to claim 1, wherein said mutant herpesvirus is defective in more than one gene essential for production of infectious virus.

5. A pharmaceutical according to claim 1, wherein the inactivating mutation allows the production and release from the cells of non-infectious viral particles.

6. A pharmaceutical according to claim 1 which consists essentially of said infectious mutant herpes virus and a pharmaceutically acceptable carrier, said pharmaceutical capable of protecting a subject immunized therewith against infection or the consequences of infection with a herpes virus.

7. A pharmaceutical according to claim 1 which is a therapeutic consisting essentially of said infectious mutant herpesvirus and a pharmaceutically acceptable carrier, said therapeutic capable of treating a patient with an established herpesvirus infection.

8. A pharmaceutical according to claim 1 adapted for administration epithelially, nasally, vaginally, or orally.

9. A pharmaceutical according to claim 1 wherein said essential gene encodes a glycoprotein.

10. A pharmaceutical according to claim 1, comprising a dose containing from about $5 \times 10^4$ pfu up to about $5 \times 10^7$ pfu of said mutant virus.

11. A pharmaceutical according to claim 1, comprising a dose containing from about $5 \times 10^4$ pfu up to about $5 \times 10^6$ pfu of said mutant virus.

12. A pharmaceutical according to claim 1, comprising a dose containing from about $5 \times 10^4$ pfu up to about $5 \times 10^5$ pfu of said mutant virus.

13. A pharmaceutical according to claim 1 wherein said herpes virus is herpes simplex virus (HSV).

14. A pharmaceutical according to claim 13 wherein said herpes simplex virus is a type-1 herpes simplex virus (HSV-1).

15. A pharmaceutical according to claim 1 wherein the defect is in the glycoprotein gH gene.

16. An assembly comprising a pharmaceutical according to claim 1 in a container with printed instructions on or accompanying the container concerning the administration of the pharmaceutical to a patient to protect against or treat conditions caused by infection with a non-retroviral virus.

17. An assembly according to claim 16 wherein the herpes virus is a herpes simplex virus (HSV).

18. An assembly according to claim 17 wherein the HSV is type 1.

19. An assembly according to claim 18 wherein the printed instructions concern protection against or treatment of facial lesions.

20. A method of preparing a pharmaceutical for prophylactic or therapeutic use in generating an immune response in a subject against a herpesvirus infection, said method comprising incorporating with a pharmaceutical vehicle an infectious virus, said infectious virus consisting essentially of a mutant herpesvirus which has an inactivating mutation in a viral gene, said viral gene being essential for the production of infectious new virus particles, wherein said mutant virus is able to cause production of infectious new virus particles in a recombinant complementing host cell line expressing a gene which complements said essential viral gene, but is unable to cause production of infectious new virus particles when said mutant virus infects a host cell other than said recombinant complementing host cell.

21. The method according to claim 20 wherein said essential gene encodes a glycoprotein.

22. The method according to claim 20 wherein said mutant virus is a herpes simplex virus.

23. The method according to claim 22 wherein said mutant virus is herpes simplex virus type 1.

24. A method comprising administering to a subject a vaccine comprising a pharmaceutically acceptable excipient and an effective immunizing amount of a mutant herpesvirus, said mutant herpesvirus containing a genome in which a viral gene encoding a protein which is essential for production of infectious virus has been deleted or inactivated, wherein said mutant virus is able to cause production of infectious new virus particles in a recombinant complementing host cell expressing a gene which complements said essential viral gene, but is unable to cause production of infectious new virus particles when said mutant virus infects a host cell other than said recombinant complementing host cell, for prophylactic or therapeutic use in generating an immune response in a subject infected therewith.

25. The method of claim 24, wherein said essential protein is involved in a post-replicative event.

26. The method of claim 24, wherein said essential protein is not required for virus assembly, but is necessary for the assembled virus to be able to infect new cells.

27. The method of claim 24 which consists essentially of said pharmaceutically acceptable excipient and an effective immunizing amount of said mutant herpesvirus.

28. The method of claim 24, wherein the mutant herpesvirus is capable of establishing a latent infection with periodic reactivation.

29. The method of claim 24, wherein said gene which has been deleted or inactivated is a glycoprotein gene.

30. The method of claim 24, 25, 26, 27, 28, or 29, wherein the herpesvirus is herpes simplex virus.

31. The method of claim 30, wherein said herpesvirus is herpes simplex virus and wherein the gene which has been deleted or inactivated is the gH gene.

32. The method of claim 31, comprising a dose containing from about $5 \times 10^4$ to about $5 \times 10^7$ pfu of said mutant virus.

33. The method of claim 31, comprising a dose containing from about $5 \times 10^4$ to about $5 \times 10^6$ pfu of said mutant virus.

34. The method of claim 31, comprising a dose containing from about $5 \times 10^4$ to about $5 \times 10^5$ pfu of said mutant virus.

35. The method of claim 24, wherein the mutant herpesvirus is defective in more than one gene essential for production of infectious virus.

36. The method according to claim 24, wherein said administration is epithelially.

37. The method according to claim 24, wherein said administration is nasally.

38. The method according to claim 24, wherein said administration is vaginally.

39. The method according to claim 24, wherein said administration is orally.

40. The method according to claim 24, wherein said administration is for protection against or treatment of facial lesions.

41. A method comprising administering to a subject a vaccine comprising a pharmaceutically acceptable excipient and an effective immunizing amount of an infectious virus, wherein the infectious virus in said vaccine consists essentially of a mutant herpesvirus containing a genome in which a viral gene encoding a protein which is essential for production of infectious virus has been deleted or inactivated, wherein said mutant virus is able to cause production of infectious new virus particles in a recombinant complementing host cell expressing a gene which complements said essential viral gene, but is unable to cause production of infectious new virus particles when said mutant virus infects a host cell other than said recombinant complementing host cell, for prophylactic or therapeutic use in generating an immune response in a subject infected therewith.

* * * * *

UNITED STATES PATENT AND TRADEMARK OFFICE
CERTIFICATE OF CORRECTION

PATENT NO. : 5,837,261

DATED : November 17, 1998

INVENTOR(S) : Inglis, et al

It is certified that error appears in the above-identified patent and that said Letters Patent is hereby corrected as shown below:

<u>On the Cover Page at Column 1, add the following to the end of Field [63] under "Related U.S. Application Data"</u>:

--Ser. No. 30,073 is the 35 USC 371 national stage of international application PCT/GB91/01632, with PCT filing date: Sept. 23, 1991; 35 USC 371 date: May 20, 1993; 35 USC 102(e) date: May 20, 1993; PCT Pub. No.: WO 92/05263; and PCT Pub. Date: Apr 2, 1992.--

Signed and Sealed this

Third Day of April, 2001

*Attest:*

NICHOLAS P. GODICI

*Attesting Officer*   *Acting Director of the United States Patent and Trademark Office*

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
        ( A ) LENGTH: 3836 base pairs
        ( B ) TYPE: nucleic acid
        ( C ) STRANDEDNESS: both
        ( D ) TOPOLOGY: linear ( x i ) SEQUENCE DESCRIPTION: SEQ ID NO:1:

```
CTGCAGCGCG  GCGGGAGGTG  GCGGGAGGAC  TGGGGCCGGC  TGACGGGGGT  CGCCGCGGCG      60

ACCCCGCGCC  CCGACCCCGA  GGACGGCGCG  GGGTCTCTGC  CCCGCATCGA  GGACACGCTG     120

TTTGCCCTGT  TCCGCGTTCC  CGAGCTGCTG  GCCCCCAACG  GGGACTTGTA  CCACATTTTT     180

GCCTGGGTCT  TGGACGTCTT  GGCCGACCGC  CTCCTTCCGA  TGCATCTATT  TGTCCTGGAT     240

TACGATCAGT  CGCCCGTCGG  GTGTCGAGAC  GCCCTGTTGC  GCCTCACCGC  CGGGATGATC     300

CCAACCCGCG  TCACAACCGC  CGGGTCCATC  GCCGAGATAC  GCGACCTGGC  GCGCACGTTT     360

GCCCGCGAGG  TGGGGGGAGT  TTAGTTCAAA  CACGGAAGCC  CGAACGGAAG  GCCTCCCGGC     420

GATGACGGCA  ATAAAAGAAC  AGAATAAAAG  GCATTGTTGT  CGTGTGGTGT  GTCCATAAGC     480
```

```
GCGGGGGTTC  GGGGCCAGGG  CTGGCACCGT  ATCAGCACCC  CACCGAAAAA  CGGAGCGGGC      540

CGATCCGTCC  TTGTTTTCGG  TCTGGTACTC  CCTTTGTGCT  TTTACCCTCA  CCCCACCCCA      600

TCCTTTGGCC  CGCGCTTACG  GCAACAAAGG  GCCTCCGATA  GCCTCCGAGG  TGCGGACGCT      660

CTTTGGGCCG  TGGGTACGGA  CACCCCCCCA  TCTGCGGACT  GGCAGCCGGG  ACGACGACC      719
```

| | | | | | | | | | | | | | | | | |
|---|---|---|---|---|---|---|---|---|---|---|---|---|---|---|---|---|
| ATG | GGC | CCC | GGT | CTG | TGG | GTG | GTG | ATG | GGG | GTC | CTG | GTG | GNC | GTT | GCC | 767 |
| Met | Gly | Pro | Gly | Leu | Trp | Val | Val | Met | Gly | Val | Leu | Val | Xaa | Val | Ala | |
| 1 | | | | 5 | | | | | 10 | | | | | 15 | | |
| GGG | GGC | CAT | GAC | ACG | TAC | TGG | ACG | GAG | CAA | ATC | GAC | CCG | TGG | TTT | TTG | 815 |
| Gly | Gly | His | Asp | Thr | Tyr | Trp | Thr | Glu | Gln | Ile | Asp | Pro | Trp | Phe | Leu | |
| | | | 20 | | | | 25 | | | | | 30 | | | | |
| CAC | GGT | CTG | GGG | TTG | GCC | CGC | ACG | TAC | TGG | CGC | GAC | ACA | AAC | ACC | GGG | 863 |
| His | Gly | Leu | Gly | Leu | Ala | Arg | Thr | Tyr | Trp | Arg | Asp | Thr | Asn | Thr | Gly | |
| | | 35 | | | | | 40 | | | | | 45 | | | | |
| CGT | CTG | TGG | TTG | CCC | AAC | ACC | CCC | GAC | GAC | CAG | CGA | CCC | CCA | GCG | CGG | 911 |
| Arg | Leu | Trp | Leu | Pro | Asn | Thr | Pro | Asp | Asp | Gln | Arg | Pro | Pro | Ala | Arg | |
| | 50 | | | | | 55 | | | | | 60 | | | | | |
| ACG | CTT | GGC | GCC | CCC | GGG | CAA | CTC | AAC | CTG | ACT | ACG | GCA | TCC | GTG | CCC | 959 |
| Thr | Leu | Gly | Ala | Pro | Gly | Gln | Leu | Asn | Leu | Thr | Thr | Ala | Ser | Val | Pro | |
| 65 | | | | 70 | | | | | 75 | | | | | 80 | | |
| ATG | CTT | CGG | TGG | TAC | GCC | GAG | CGC | TTT | TGT | TTC | GTG | TTG | GTC | ACC | ACG | 1007 |
| Met | Leu | Arg | Trp | Tyr | Ala | Glu | Arg | Phe | Cys | Phe | Val | Leu | Val | Thr | Thr | |
| | | | | 85 | | | | 90 | | | | | 95 | | | |
| GCC | GAG | TTT | CCT | CGG | GAC | CCC | GGG | CAG | CTG | CTT | TAC | ATC | CCA | AAG | ACC | 1055 |
| Ala | Glu | Phe | Pro | Arg | Asp | Pro | Gly | Gln | Leu | Leu | Tyr | Ile | Pro | Lys | Thr | |
| | | | 100 | | | | | 105 | | | | | 110 | | | |
| TAT | CTG | CTC | GGC | CGG | CCT | CGG | AAC | GCG | AGC | CTG | CCC | GAG | CTC | CCC | GAG | 1103 |
| Tyr | Leu | Leu | Gly | Arg | Pro | Arg | Asn | Ala | Ser | Leu | Pro | Glu | Leu | Pro | Glu | |
| | | 115 | | | | | 120 | | | | | 125 | | | | |
| GCG | GGG | CCC | ACG | TCC | CGT | CCC | CCC | GCC | GAG | GTG | ACC | CAG | CTC | AAG | GGA | 1151 |
| Ala | Gly | Pro | Thr | Ser | Arg | Pro | Pro | Ala | Glu | Val | Thr | Gln | Leu | Lys | Gly | |
| | 130 | | | | | 135 | | | | | 140 | | | | | |
| CTG | CTG | CAC | AAC | CCC | GGC | GCC | TCC | GCG | ATG | TTG | CGG | TCC | CGG | GCC | TGG | 1199 |
| Leu | Leu | His | Asn | Pro | Gly | Ala | Ser | Ala | Met | Leu | Arg | Ser | Arg | Ala | Trp | |
| 145 | | | | | 150 | | | | | 155 | | | | | 160 | |
| GTA | ACA | TTC | GCG | GCC | GCG | CCG | GAC | CGC | GAG | GGG | CTT | ACG | TTN | CCG | CGG | 1247 |
| Val | Thr | Phe | Ala | Ala | Ala | Pro | Asp | Arg | Glu | Gly | Leu | Thr | Xaa | Pro | Arg | |
| | | | | 165 | | | | | 170 | | | | | 175 | | |
| GGA | GAC | GAC | GGG | GCG | ACC | GAG | AGG | CAC | CCG | GAC | GGC | CGA | CGC | AAC | GCG | 1295 |
| Gly | Asp | Asp | Gly | Ala | Thr | Glu | Arg | His | Pro | Asp | Gly | Arg | Arg | Asn | Ala | |
| | | | 180 | | | | | 185 | | | | | 190 | | | |
| NCC | CCG | GGG | CCG | CCC | GCG | GGG | GCG | CCG | AGG | CAT | CCG | ACG | ACG | AAC | CTG | 1343 |
| Xaa | Pro | Gly | Pro | Pro | Ala | Gly | Ala | Pro | Arg | His | Pro | Thr | Thr | Asn | Leu | |
| | | 195 | | | | | 200 | | | | | 205 | | | | |
| AGC | ATC | GCG | CAT | CTG | CAC | AAC | GCG | TCC | GTG | ANC | CTG | CTG | GCC | GCC | AGG | 1391 |
| Ser | Ile | Ala | His | Leu | His | Asn | Ala | Ser | Val | Xaa | Leu | Leu | Ala | Ala | Arg | |
| | 210 | | | | | 215 | | | | | 220 | | | | | |
| GGC | CTG | CTA | CGG | ACT | CCG | GGT | CGG | TAC | GTG | TAC | CTC | TCC | CCG | TCG | GCC | 1439 |
| Gly | Leu | Leu | Arg | Thr | Pro | Gly | Arg | Tyr | Val | Tyr | Leu | Ser | Pro | Ser | Ala | |
| 225 | | | | | 230 | | | | | 235 | | | | | 240 | |
| TCG | ACG | TGG | CCC | GTG | GGC | GTC | TGG | ACG | ACG | GGG | CTG | GCG | TTC | GGG | | 1487 |
| Ser | Thr | Trp | Pro | Val | Gly | Val | Trp | Thr | Thr | Gly | Gly | Leu | Ala | Phe | Gly | |
| | | | | 245 | | | | | 250 | | | | | 255 | | |
| TGC | GAC | GCC | GCG | CTC | GTG | CGC | GCG | CGA | TAC | GGG | AAG | GGC | TTC | ATG | GGG | 1535 |
| Cys | Asp | Ala | Ala | Leu | Val | Arg | Ala | Arg | Tyr | Gly | Lys | Gly | Phe | Met | Gly | |
| | | | 260 | | | | | 265 | | | | | 270 | | | |
| CTC | GTG | ATA | TCG | ATG | CGG | GAC | AGC | CCT | CCG | GCC | GAG | ATC | ATA | GTG | GTG | 1583 |
| Leu | Val | Ile | Ser | Met | Arg | Asp | Ser | Pro | Pro | Ala | Glu | Ile | Ile | Val | Val | |
| | | 275 | | | | | 280 | | | | | 285 | | | | |

```
CCT  GCG  GAC  AAG  ACC  CTC  GCT  CGG  GTC  GGA  AAT  CCG  ACC  GAC  GAA  AAC   1631
Pro  Ala  Asp  Lys  Thr  Leu  Ala  Arg  Val  Gly  Asn  Pro  Thr  Asp  Glu  Asn
     290                 295                 300

GCC  CCG  CGT  GCT  CCC  CGC  GCT  CCG  GCC  GGC  CCC  AGG  TAT  CGC  GTC  TTT   1679
Ala  Pro  Arg  Ala  Pro  Arg  Ala  Pro  Ala  Gly  Pro  Arg  Tyr  Arg  Val  Phe
305                      310                 315                      320

GTC  CTG  GGG  GCC  CCG  ACG  CCC  GCC  GAC  AAC  GGC  NTC  GGC  GCT  GGA  CCC   1727
Val  Leu  Gly  Ala  Pro  Thr  Pro  Ala  Asp  Asn  Gly  Xaa  Gly  Ala  Gly  Pro
                    325                 330                      335

CCT  CGG  CGG  GTG  GCC  GGC  TAC  CCC  GAG  GAG  AGC  ACG  AAC  TAC  GCC  CAG   1775
Pro  Arg  Arg  Val  Ala  Gly  Tyr  Pro  Glu  Glu  Ser  Thr  Asn  Tyr  Ala  Gln
               340                 345                      350

TAT  ATG  TCG  CGG  GCC  TAT  GCG  GAG  TTT  TTG  GGG  GAG  GAC  CCG  GGC  TCC   1823
Tyr  Met  Ser  Arg  Ala  Tyr  Ala  Glu  Phe  Leu  Gly  Glu  Asp  Pro  Gly  Ser
          355                 360                 365

GGC  ACG  GAC  GAC  GCG  CGT  CCG  TCC  CTG  TTC  TGG  CGC  CTC  GCG  GGG  CTG   1871
Gly  Thr  Asp  Asp  Ala  Arg  Pro  Ser  Leu  Phe  Trp  Arg  Leu  Ala  Gly  Leu
     370                 375                 380

CTC  GCC  TCG  TCG  GGG  TTT  GCG  TTC  GTC  AAC  GCG  GCC  CAC  GCC  CAC  GAC   1919
Leu  Ala  Ser  Ser  Gly  Phe  Ala  Phe  Val  Asn  Ala  Ala  His  Ala  His  Asp
385                 390                 395                           400

GCG  ATT  CGC  CTC  TCC  GAC  CTG  CTG  GGT  TTT  TTG  GCC  CAC  TCG  CGC  GTG   1967
Ala  Ile  Arg  Leu  Ser  Asp  Leu  Leu  Gly  Phe  Leu  Ala  His  Ser  Arg  Val
                    405                 410                      415

CTG  GCC  GGC  CTG  GCC  GCC  CGG  GGA  GCA  GCG  GGC  TGC  GCG  GCC  GAC  TCG   2015
Leu  Ala  Gly  Leu  Ala  Ala  Arg  Gly  Ala  Ala  Gly  Cys  Ala  Ala  Asp  Ser
               420                 425                      430

GTG  TTC  CTG  AAC  GTG  TCC  GTG  TTG  GAC  CCG  GCG  GCC  CGT  CTG  CGG  CTG   2063
Val  Phe  Leu  Asn  Val  Ser  Val  Leu  Asp  Pro  Ala  Ala  Arg  Leu  Arg  Leu
          435                 440                      445

GAG  GCG  CGC  CTC  GGG  CAT  CTG  GTG  GCC  GCG  ATC  CTC  GAG  CGA  GAG  CAG   2111
Glu  Ala  Arg  Leu  Gly  His  Leu  Val  Ala  Ala  Ile  Leu  Glu  Arg  Glu  Gln
     450                 455                 460

AGC  CTG  GCG  GCG  CAC  GCG  CTG  GGC  TAT  CAG  CTG  GCG  TTC  GTG  TTG  GAC   2159
Ser  Leu  Ala  Ala  His  Ala  Leu  Gly  Tyr  Gln  Leu  Ala  Phe  Val  Leu  Asp
465                 470                 475                           480

AGC  CCC  GCG  GCC  TAT  GGC  GGG  TTG  GCC  CCG  AGC  GCG  GCC  CGC  CTG  ATC   2207
Ser  Pro  Ala  Ala  Tyr  Gly  Gly  Leu  Ala  Pro  Ser  Ala  Ala  Arg  Leu  Ile
               485                 490                      495

GAC  GCC  CTT  GTT  ACC  GCG  CAG  TTT  CTC  GGC  GGC  CGC  GTA  ACC  GCC  CCG   2255
Asp  Ala  Leu  Val  Thr  Ala  Gln  Phe  Leu  Gly  Gly  Arg  Val  Thr  Ala  Pro
          500                 505                      510

ATG  GTC  CGC  CGA  GCG  CTG  TTT  TAC  GCC  ACG  GCC  GTC  CTC  CGG  GCG  CCG   2303
Met  Val  Arg  Arg  Ala  Leu  Phe  Tyr  Ala  Thr  Ala  Val  Leu  Arg  Ala  Pro
               515                 520                      525

TTC  CTG  GCG  GGC  GTG  CCC  TCG  GCC  GGG  CAG  CGG  GAA  CGC  CCG  CGG  GGC   2351
Phe  Leu  Ala  Gly  Val  Pro  Ser  Ala  Gly  Gln  Arg  Glu  Arg  Pro  Arg  Gly
530                 535                      540

CTC  CTC  ATA  ACC  ACG  GCC  CTG  TGT  ACG  TCC  GAC  GTC  GCC  GCG  GCG  ACC   2399
Leu  Leu  Ile  Thr  Thr  Ala  Leu  Cys  Thr  Ser  Asp  Val  Ala  Ala  Ala  Thr
545                 550                 555                           560

CAC  GCC  GAT  CTC  CGG  GCC  GCG  CTA  CGC  AGG  ACC  GAC  CAC  CAG  AAA  AAC   2447
His  Ala  Asp  Leu  Arg  Ala  Ala  Leu  Arg  Arg  Thr  Asp  His  Gln  Lys  Asn
               565                 570                      575

CTC  TTC  TGG  CTC  CCG  GAC  CAC  TTT  TCC  CCA  TGC  GCA  CGT  TCC  CTG  CCG   2495
Leu  Phe  Trp  Leu  Pro  Asp  His  Phe  Ser  Pro  Cys  Ala  Arg  Ser  Leu  Pro
          580                 585                      590

TTC  GAT  CTC  GCC  GAG  GGC  GGG  TTC  ATC  CTG  GAC  GCG  CTG  GCC  ATG  GCC   2543
Phe  Asp  Leu  Ala  Glu  Gly  Gly  Phe  Ile  Leu  Asp  Ala  Leu  Ala  Met  Ala
          595                 600                      605
```

| | | | | | | | | | | | | | | | | |
|---|---|---|---|---|---|---|---|---|---|---|---|---|---|---|---|---|
| ACC | CGA | TCC | GAC | ATC | CCG | GCG | GAC | GTC | ATG | GCA | CAA | CAG | ACC | CGC | GGC | 2591 |
| Thr | Arg | Ser | Asp | Ile | Pro | Ala | Asp | Val | Met | Ala | Gln | Gln | Thr | Arg | Gly | |
| 610 | | | | 615 | | | | | 620 | | | | | | | |
| GTG | GCC | TCC | GCT | CTC | ACG | CNC | TGG | GCG | ACT | CAC | AAC | GCC | CTG | ATC | CGC | 2639 |
| Val | Ala | Ser | Ala | Leu | Thr | Xaa | Trp | Ala | Thr | His | Asn | Ala | Leu | Ile | Arg | |
| 625 | | | | | 630 | | | | | 635 | | | | | 640 | |
| GCC | TTC | GTC | CCG | GAG | GCC | ACC | CAC | CAG | TGT | AGC | GGC | CCG | TCG | CAC | AAC | 2687 |
| Ala | Phe | Val | Pro | Glu | Ala | Thr | His | Gln | Cys | Ser | Gly | Pro | Ser | His | Asn | |
| | | | | 645 | | | | | 650 | | | | | 655 | | |
| GNG | GAG | CCC | CGG | ATC | CTC | GTG | CCC | ATC | ACC | CAC | AAC | GCC | AGC | TAC | GTC | 2735 |
| Xaa | Glu | Pro | Arg | Ile | Leu | Val | Pro | Ile | Thr | His | Asn | Ala | Ser | Tyr | Val | |
| | | | 660 | | | | | 665 | | | | | 670 | | | |
| GTC | ACC | CAC | TAC | CCC | CCT | TGC | CCC | CGC | GGG | ATC | GGA | TAC | AAG | CTT | ACG | 2783 |
| Val | Thr | His | Tyr | Pro | Pro | Cys | Pro | Arg | Gly | Ile | Gly | Tyr | Lys | Leu | Thr | |
| | | 675 | | | | | 680 | | | | | 685 | | | | |
| GGC | GTT | GAC | GTC | CGC | CGC | CCG | CTG | TTT | ATC | ACC | TAT | CTC | ACC | GCC | ACC | 2831 |
| Gly | Val | Asp | Val | Arg | Arg | Pro | Leu | Phe | Ile | Thr | Tyr | Leu | Thr | Ala | Thr | |
| | | 690 | | | | 695 | | | | | 700 | | | | | |
| TGC | GAA | GGG | CAC | GCG | CGG | GAG | ATT | GAG | CCG | CCG | CGG | CTG | GTG | CGC | ACC | 2879 |
| Cys | Glu | Gly | His | Ala | Arg | Glu | Ile | Glu | Pro | Pro | Arg | Leu | Val | Arg | Thr | |
| 705 | | | | 710 | | | | | 715 | | | | | 720 | | |
| GAA | AAC | CGG | CGC | GAC | CTC | GGC | CTC | GTG | GGG | GCC | GTG | TTT | CTG | CGC | TAC | 2927 |
| Glu | Asn | Arg | Arg | Asp | Leu | Gly | Leu | Val | Gly | Ala | Val | Phe | Leu | Arg | Tyr | |
| | | | | 725 | | | | | 730 | | | | | 735 | | |
| ACC | CCG | GCC | GGG | GAG | GTC | ATG | TCG | GTG | CTG | CTG | GTG | GAC | ACG | GAT | GCC | 2975 |
| Thr | Pro | Ala | Gly | Glu | Val | Met | Ser | Val | Leu | Leu | Val | Asp | Thr | Asp | Ala | |
| | | | 740 | | | | | 745 | | | | | 750 | | | |
| ACC | CAA | CAG | CAG | CTG | GCC | CAG | GGG | CCG | GTG | GCG | GGC | ACC | CCG | AAC | GTG | 3023 |
| Thr | Gln | Gln | Gln | Leu | Ala | Gln | Gly | Pro | Val | Ala | Gly | Thr | Pro | Asn | Val | |
| | | 755 | | | | | 760 | | | | | 765 | | | | |
| TTT | TCC | AGC | GAC | GTG | CCG | TCC | GTG | GCC | CTG | TTG | TTG | TTC | CCC | AAC | GGA | 3071 |
| Phe | Ser | Ser | Asp | Val | Pro | Ser | Val | Ala | Leu | Leu | Leu | Phe | Pro | Asn | Gly | |
| | 770 | | | | | 775 | | | | | 780 | | | | | |
| ACT | GTG | ATT | CAT | CTG | CTG | GCC | TTT | GAC | ACG | CTG | CCC | ATC | GCC | ACC | ATC | 3119 |
| Thr | Val | Ile | His | Leu | Leu | Ala | Phe | Asp | Thr | Leu | Pro | Ile | Ala | Thr | Ile | |
| 785 | | | | | 790 | | | | | 795 | | | | | 800 | |
| GCC | CCC | GGG | TTT | CTG | GCC | GCG | TCC | GCG | CTG | GGG | GTC | GTT | ATG | ATT | ACC | 3167 |
| Ala | Pro | Gly | Phe | Leu | Ala | Ala | Ser | Ala | Leu | Gly | Val | Val | Met | Ile | Thr | |
| | | | 805 | | | | | 810 | | | | | 815 | | | |
| GCG | GCC | CTG | GCG | GGC | ATC | CTC | AGG | GTG | GTC | CGA | ACG | TGC | GTC | CCA | TTT | 3215 |
| Ala | Ala | Leu | Ala | Gly | Ile | Leu | Arg | Val | Val | Arg | Thr | Cys | Val | Pro | Phe | |
| | | | 820 | | | | | 825 | | | | | 830 | | | |
| TTG | TGG | AGA | CGC | GAA | TAAACGGGTG | TGTGGACGCA | GCGGCGTCCA | GCCCAACCCA | | | | | | | | 3270 |
| Leu | Trp | Arg | Arg | Glu | | | | | | | | | | | | |
| | | 835 | | | | | | | | | | | | | | |

| | | | | |
|---|---|---|---|---|
| ACCGACTCCC | TCCGTGTCCG | CGGTCTGTTT | GTTATTGTGT | CCGCCGTGGC | TCCGCTACCG | 3330 |
| CCTCTGTTCC | TTTCCCTTCT | CCATTCCTGT | TTCCTTTCCT | TCCCCCCCCC | CCATAGTCCC | 3390 |
| CCGTATAGGC | ATACAACGGC | ATCCGTGGGT | TAGAAAACGA | CTGCACTTTA | TTGGGATATC | 3450 |
| TCACACAGAC | TGGCCGTGCT | GGGCGCGAGC | CAGGCAAACG | GTAAGCAGCG | CGTCCAGGTA | 3510 |
| CCCGGCGGTT | CGCGTGCGGC | CAGCCGCCCC | CGCCGGCCCG | CGGTCAAACG | CGGACATCCG | 3570 |
| GTCGACGTCC | CCCACGGTCA | GGACCAGGGA | CGTCACGCCC | GTCAGGCGCN | CGGTATGCGT | 3630 |
| GGCCGCGGCC | AGGCGTCCGT | GGCCGGCGTA | CAACACGCCC | AGGAACGCGC | CGAGGTACAT | 3690 |
| GACGTGCTCG | GGCGAGACGG | ACCCCCCCGG | GGTCAGGCGT | TGCGAGTCCA | CAAAGCGCAG | 3750 |
| CAGGGCGGCG | CTGTCGGCCC | GCGACGTCGC | TCCCCACCGG | CACGTCCTTG | GCGGGAGGA | 3810 |
| GGTCGAACAT | GAGGAGCTGC | TCGCGA | | | | 3836 |

( 2 ) INFORMATION FOR SEQ ID NO:2:

( i ) SEQUENCE CHARACTERISTICS:
        ( A ) LENGTH: 837 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Gly Pro Gly Leu Trp Val Val Met Gly Val Leu Val Gly Val Ala
 1               5                  10                  15

Gly Gly His Asp Thr Tyr Trp Thr Glu Gln Ile Asp Pro Trp Phe Leu
            20                  25                  30

His Gly Leu Gly Leu Ala Arg Thr Tyr Trp Arg Asp Thr Asn Thr Gly
         35                  40                  45

Arg Leu Trp Leu Pro Asn Thr Pro Asp Asp Gln Arg Pro Pro Ala Arg
     50                  55                  60

Thr Leu Gly Ala Pro Gly Gln Leu Asn Leu Thr Thr Ala Ser Val Pro
 65                  70                  75                  80

Met Leu Arg Trp Tyr Ala Glu Arg Phe Cys Phe Val Leu Val Thr Thr
                 85                  90                  95

Ala Glu Phe Pro Arg Asp Pro Gly Gln Leu Leu Tyr Ile Pro Lys Thr
                100                 105                 110

Tyr Leu Leu Gly Arg Pro Arg Asn Ala Ser Leu Pro Glu Leu Pro Glu
            115                 120                 125

Ala Gly Pro Thr Ser Arg Pro Pro Ala Glu Val Thr Gln Leu Lys Gly
        130                 135                 140

Leu Leu His Asn Pro Gly Ala Ser Ala Met Leu Arg Ser Arg Ala Trp
145                 150                 155                 160

Val Thr Phe Ala Ala Ala Pro Asp Arg Glu Gly Leu Thr Leu Pro Arg
                165                 170                 175

Gly Asp Asp Gly Ala Thr Glu Arg His Pro Asp Gly Arg Arg Asn Ala
            180                 185                 190

Ala Pro Gly Pro Pro Ala Gly Ala Pro Arg His Pro Thr Thr Asn Leu
        195                 200                 205

Ser Ile Ala His Leu His Asn Ala Ser Val Ser Leu Leu Ala Ala Arg
    210                 215                 220

Gly Leu Leu Arg Thr Pro Gly Arg Tyr Val Tyr Leu Ser Pro Ser Ala
225                 230                 235                 240

Ser Thr Trp Pro Val Gly Val Trp Thr Thr Gly Gly Leu Ala Phe Gly
                245                 250                 255

Cys Asp Ala Ala Leu Val Arg Ala Arg Tyr Gly Lys Gly Phe Met Gly
            260                 265                 270

Leu Val Ile Ser Met Arg Asp Ser Pro Pro Ala Glu Ile Ile Val Val
        275                 280                 285

Pro Ala Asp Lys Thr Leu Ala Arg Val Gly Asn Pro Thr Asp Glu Asn
    290                 295                 300

Ala Pro Arg Ala Pro Arg Ala Pro Ala Gly Pro Arg Tyr Arg Val Phe
305                 310                 315                 320

Val Leu Gly Ala Pro Thr Pro Ala Asp Asn Gly Val Gly Ala Gly Pro
                325                 330                 335

Pro Arg Arg Val Ala Gly Tyr Pro Glu Glu Ser Thr Asn Tyr Ala Gln
            340                 345                 350

Tyr Met Ser Arg Ala Tyr Ala Glu Phe Leu Gly Glu Asp Pro Gly Ser
```

|     |     |     | 355 |     |     |     | 360 |     |     |     | 365 |     |     |
| --- | --- | --- | --- | --- | --- | --- | --- | --- | --- | --- | --- | --- | --- |

Gly Thr Asp Asp Ala Arg Pro Ser Leu Phe Trp Arg Leu Ala Gly Leu
        370                 375                 380

Leu Ala Ser Ser Gly Phe Ala Phe Val Asn Ala His Ala His Asp
385                 390                 395                 400

Ala Ile Arg Leu Ser Asp Leu Leu Gly Phe Leu Ala His Ser Arg Val
                405                 410                 415

Leu Ala Gly Leu Ala Ala Arg Gly Ala Gly Cys Ala Ala Asp Ser
                420                 425                 430

Val Phe Leu Asn Val Ser Val Leu Asp Pro Ala Ala Arg Leu Arg Leu
        435                 440                 445

Glu Ala Arg Leu Gly His Leu Val Ala Ala Ile Leu Glu Arg Glu Gln
        450                 455                 460

Ser Leu Ala Ala His Ala Leu Gly Tyr Gln Leu Ala Phe Val Leu Asp
465                 470                 475                 480

Ser Pro Ala Ala Tyr Gly Gly Leu Ala Pro Ser Ala Ala Arg Leu Ile
                485                 490                 495

Asp Ala Leu Val Thr Ala Gln Phe Leu Gly Gly Arg Val Thr Ala Pro
                500                 505                 510

Met Val Arg Arg Ala Leu Phe Tyr Ala Thr Ala Val Leu Arg Ala Pro
                515                 520                 525

Phe Leu Ala Gly Val Pro Ser Ala Gly Gln Arg Glu Arg Pro Arg Gly
        530                 535                 540

Leu Leu Ile Thr Thr Ala Leu Cys Thr Ser Asp Val Ala Ala Ala Thr
545                 550                 555                 560

His Ala Asp Leu Arg Ala Ala Leu Arg Arg Thr Asp His Gln Lys Asn
                565                 570                 575

Leu Phe Trp Leu Pro Asp His Phe Ser Pro Cys Ala Arg Ser Leu Pro
        580                 585                 590

Phe Asp Leu Ala Glu Gly Gly Phe Ile Leu Asp Ala Leu Ala Met Ala
        595                 600                 605

Thr Arg Ser Asp Ile Pro Ala Asp Val Met Ala Gln Gln Thr Arg Gly
        610                 615                 620

Val Ala Ser Ala Leu Thr Arg Trp Ala Thr His Asn Ala Leu Ile Arg
625                 630                 635                 640

Ala Phe Val Pro Glu Ala Thr His Gln Cys Ser Gly Pro Ser His Asn
                645                 650                 655

Gly Glu Pro Arg Ile Leu Val Pro Ile Thr His Asn Ala Ser Tyr Val
                660                 665                 670

Val Thr His Tyr Pro Pro Cys Pro Arg Gly Ile Gly Tyr Lys Leu Thr
                675                 680                 685

Gly Val Asp Val Arg Arg Pro Leu Phe Ile Thr Tyr Leu Thr Ala Thr
        690                 695                 700

Cys Glu Gly His Ala Arg Glu Ile Glu Pro Pro Arg Leu Val Arg Thr
705                 710                 715                 720

Glu Asn Arg Arg Asp Leu Gly Leu Val Gly Ala Val Phe Leu Arg Tyr
                725                 730                 735

Thr Pro Ala Gly Glu Val Met Ser Val Leu Leu Val Asp Thr Asp Ala
                740                 745                 750

Thr Gln Gln Gln Leu Ala Gln Gly Pro Val Ala Gly Thr Pro Asn Val
        755                 760                 765

Phe Ser Ser Asp Val Pro Ser Val Ala Leu Leu Leu Phe Pro Asn Gly
        770                 775                 780

| Thr | Val | Ile | His | Leu | Leu | Ala | Phe | Asp | Thr | Leu | Pro | Ile | Ala | Thr | Ile |
|---|---|---|---|---|---|---|---|---|---|---|---|---|---|---|---|
| 785 | | | | | 790 | | | | | 795 | | | | | 800 |

| Ala | Pro | Gly | Phe | Leu | Ala | Ala | Ser | Ala | Leu | Gly | Val | Val | Met | Ile | Thr |
|---|---|---|---|---|---|---|---|---|---|---|---|---|---|---|---|
| | | | | 805 | | | | | 810 | | | | | 815 | |

| Ala | Ala | Leu | Ala | Gly | Ile | Leu | Arg | Val | Val | Arg | Thr | Cys | Val | Pro | Phe |
|---|---|---|---|---|---|---|---|---|---|---|---|---|---|---|---|
| | | | 820 | | | | | 825 | | | | | 830 | | |

| Leu | Trp | Arg | Arg | Glu |
|---|---|---|---|---|
| | | | | 835 |

( 2 ) INFORMATION FOR SEQ ID NO:3:

( i ) SEQUENCE CHARACTERISTICS:
        ( A ) LENGTH: 3762 base pairs
        ( B ) TYPE: nucleic acid
        ( C ) STRANDEDNESS: both
        ( D ) TOPOLOGY: linear ( x i ) SEQUENCE DESCRIPTION: SEQ ID NO:3:

```
CTGCAGGGCG   GCGGGTCGTG   GCGGGAGGAT   TGGGGACAGC   TTTCGGGGC   GGCCGTGCCG        60
CCCCAGGGTG   CCGAGCCCCA   GAGCAACGCG   GGCCCACGAC   CCCATATCGG   GGACACGTTA       120
TTTACCCTGT   TTCGGGCCCC   CGAGTTGCTG   GCCCCCAACG   GCGACCTGTA   TAACGTGTTT       180
GCCTGGGCTT   TGGACGTCTT   GGCCAAACGC   CTCCGTCCCA   TGCATGTCTT   TATCCTGGAT       240
TACGACCAAT   CGCCCGCCGG   CTGCCGGGAC   GCCCTGCTGC   AACTTACCTC   CGGGATGGTC       300
CAGACCCACG   TCACCACCCC   AGGCTCCATA   CCGACGATCT   GCGACCTGGC   GCGCACGTTT       360
GCCCGGGAGA   TCCGGGAGCC   TAACTGAAAC   ACGGAAGGAG   ACAATACCGG   AAGGAACCCG       420
CGCTATGACG   GCAATAAAAA   GACAGAATAA   AACGCACGGG   TGTTGGGTCG   TTTGTTCATA       480
AACGCGGGGT   TCGGTCCCAG   GGCTGGCACT   CTGTCGATAC   CCCACCGAGA   CCCCATTGGG       540
ACCAATACGC   CCGCGTTTCT   TCCTTTTCCC   CACCCCAACC   CCCAAGTTCG   GGTGAAGGCC       600
CAGGGCTCGC   AGCCAACGTC   GGGGCGGCAA   GCCCTGCCAT   AGCCACGGGC   CCCGTGGGTT       660
AGGGACGGGG   TCCCCCATGG   GGAATGGTTT   ATGGTTCGTG   GGGGTTATTA   TTTTGGGCGT       720
TGCGTGGGGT   CAGGTCCACG   ACTGGACTGA   GCAGACAGAC   CCATGGTTTT   TGGATGGCCT       780
GGGCATGGAC   CGCATGTACT   GGCGCGACAC   GAACACCGGG   CGTCTGTGGC   TGCCAAACAC       840
CCCCGACCCC   CAAAAACCAC   CGCGCGGATT   TCTGGCGCCG   CCGGACGAAC   TAAACCTGAC       900
TACGGCATCT   CTGCCCCTTC   TTCGCTGGTA   CGAGGAGCGC   TTTTGTTTTG   TATTGGTCAC       960
CACGGCCGAG   TTTCGCGGG    ACCCCGGCCA   GCTGCTTTAC   ATCCGAAGA    CCTACCTGCT      1020
CGGCCGGCCC   CCGAACGCGA   GCCTGCCCGC   CCCACCACG    GTCGAGCCGA   CCGCCCAGCC      1080
TCCCCCCTCG   GTCGCCCCCC   TTAAGGGTCT   CTTGCACAAT   CCAGCCGCCT   CCGTGTTGCT      1140
GCGTTCCCGG   GCCTGGGTAA   CGTTTTCGGC   CGTCCCTGAC   CCCGAGGCCC   TGACGTTCCC      1200
GCGGGGAGAC   AACGTGGCGA   CGGCGAGCCA   CCCGAGCGGG   CCGCGTGATA   CCCGCCCCCC      1260
CGACCGCCGG   TTGGGGCCCG   GCGGCACCCG   ACGACGGAGC   TGGACATCAC   GCACCTGCAC      1320
AACGCGTCCA   CGACCTGGTT   GGCCACCCGG   GGCCTGTTGA   GATCCCAGG    TAGGTACGTG      1380
TATTTCTCCC   CGTCGGCCTC   GACGTGGCCC   GTGGGCATCT   GGACGACGGG   GGAGCTGGTG      1440
CTCGGGTGCG   ATGCCGGGGT   GGTGCGCGCG   CGCTACGGGC   GGGAATTCAT   GGGGCTCGTG      1500
ATATCCATGC   ACGACAGCCC   TCCGGTGGAA   GTGATGGTGG   TCCCCGCGGG   CCAGACGCTA      1560
GATCGGGTCG   GGGACCCCGC   GGACGAAAAC   CCCCCGGGGG   CTCTTCCCGG   GCCCCGGGC      1620
GGCCCCCGGT   ATCGGGTCTT   TGTCCTAGGG   TCCCTGACGC   GGGCCGACAA   CGGCTCCGCG      1680
CTGGACGCCC   TCCGCCGCGT   GGGCGGCTAC   CCGGAGGAGG   GCACGAACTA   CGCCCAGTTC      1740
```

-continued

| | | | | | | |
|---|---|---|---|---|---|---|
| CTGTCGCGGG | CATACGCGGA | GTTTTTCTCG | GGGGACGCGG | GCGCCGAGCA | GGGCCCGCGC | 1800 |
| CCCCCTCTCT | TCTGGCGCCT | AACGGGGCTG | CTCGCGACGT | CGGGTTTTGC | TTTCGTGAAC | 1860 |
| GCCGCCCACG | CAAACGGCGC | GGTCTGCCTC | TCCGACCTGC | TAGGCTTTTT | GGCCCACTCG | 1920 |
| CGCGCGCTTG | CCGGGTTGGC | CGCCCGCGCG | GCCGCGGGCT | GTGCCGCGGA | TTCTGTGTTT | 1980 |
| TTTAATGTGT | CAGTCTTGGA | TCCCACGGCC | CGCCTGCAGC | TAGAGGCTCG | GCTCCAGCAC | 2040 |
| CTGGTGGCCG | AGATTCTGGA | GCGCGAACAG | AGCTTGGCAT | TACACGCGCT | GGGCTATCAG | 2100 |
| CTGGCCTTCG | TGCTGGATAG | CCCCTCGGCG | TACGACGCAG | TGGCGCCCAG | CGCAGCCCAT | 2160 |
| CTCATCGACG | CCCTGCTATG | CCCGAGTTTC | TAGGGGCCG  | CGTGCTGACC | ACCCCGGTCG | 2220 |
| TCCACCGGGC | GCTATTTTAC | GCCTCGGCTG | TCCTCCGGCA | GCCGTTCTTG | GCTGGCGTCC | 2280 |
| CCTCGGCGGT | GCAGCGGGAA | CGCGCCCGCC | GGACCCTTCT | GATAGCCTCG | GCCCTGTGTA | 2340 |
| CGTCCGACGT | CGCCGCAGCG | ACCAACGCCG | ACCTCCGGAC | CGCGCTGGCC | CGGGCCGACC | 2400 |
| ACCAGAAAAC | CCTCTTTTGG | CTTCCGGACC | ACTTTTCGCC | ATGCGCGGCC | TCCCTGCGCT | 2460 |
| TTGATCTAGA | CGAGAGCGTG | TTTATCCTGG | ACGCGCTGGC | TCAAGCCACC | CGATCCGAGA | 2520 |
| CCCCGGTCGA | AGTCCTGGCC | CAGCAGACCC | ACGGCCTCGC | CTCGACCCTG | ACGCGTTGGG | 2580 |
| CACACTACAA | CGCCCTGATC | CGCGCCTTCG | TCCCTGAGGC | CTCACATCGG | TGCGGGGGGC | 2640 |
| AGTCTGCCAA | CGTCGAGCCA | CGGATCCTGG | TACCCATCAC | CCACAACGCC | AGCTACGTCG | 2700 |
| TCACCCACTC | CCCTCTGCCC | CGGGGGATCG | GCTACAAGCT | CACCGGCGTC | GACGTCCGAC | 2760 |
| GCCCACTGTT | CCTAACCTAC | CTCACCGCGA | CATGCGAAGG | CTCCACCCGG | GATATCGAGT | 2820 |
| CCAAGCGGCT | GGTGCGCACC | CAAAACCAGC | GCGACCTGGG | GCTCGTGGGG | GCCGTGTTTA | 2880 |
| TGCGCTACAC | CCCGGCCGGG | GAGGTCATGT | CTGTGTTGCT | GGTGGATACG | GACAACACAC | 2940 |
| AGCAGCAAAT | CGCCGCCGGG | CCGACGGAGG | GCGCCCCAAG | CGTGTTTTCG | AGCGACGTGC | 3000 |
| CGTCCACGGC | CTTGTTGCTA | TTTCCAAACG | GAACCGTCAT | TCATTTGCTA | GCCTTTGACA | 3060 |
| CGCAGCCCGT | GGCCGCAATT | GCGCCCGGGT | TTCTGGCCGC | CTCTGCGCTG | GGCGTGGTTA | 3120 |
| TGATTACCGC | CGCCCTGGCT | GGCATCCTAA | AGGTTCTCCG | GACAAGTGTC | CCGTTTTTTT | 3180 |
| GGAGACGCGA | ATAAAGTGGG | CGTGGCTTCG | GCCGTTTCTC | CGCCCGACCG | AATAAACTGT | 3240 |
| AACCGTGTCT | GTGGTTTGTT | TGTTCAGGCC | CCGGTGGTGC | CGCTCCCCCA | GCCCCTCTTT | 3300 |
| GCTTTCCCTC | CCCCCCCCCC | GGAGAGGCGT | CCATTGACAC | ACAAGGGTGT | AGTAGCGATA | 3360 |
| TACGTTTATT | GGGGTCTTTT | ACACAGACTG | TCCGTGTTGG | GAGCGAGCGA | GACGAACGGT | 3420 |
| AAGAAGCACA | TCCAGGTACC | CGGCGGCCCG | CGTGCGGCTG | GCCGCGCCCG | CCGCTCCGCG | 3480 |
| GTCAAACGCG | GAAAGACGGT | CCACGTCACC | CACCGCTAGC | ACCAGGAGG  | TCACCCCTGT | 3540 |
| CAGCCGCGCG | GTGTGCGTGG | CTGCGGACAT | GCGCCCGCGG | CCAGCGTACA | GCACGCTCAG | 3600 |
| GAACGCACCA | AGGTACGCGA | CGTGCTCGGG | GGAGATCACC | CCCCGGGGA  | CGGCGAGACG | 3660 |
| TTGCGATTCT | ATAAAGCGCA | GCAGAGCGGT | GCTGTCGGCC | TGCACGTCGC | TTCCCACCGG | 3720 |
| CACGTCCTTT | GGGGGGAGAA | GGTCGAACAT | GAGAGCTGCT | CG         |            | 3762 |

( 2 ) INFORMATION FOR SEQ ID NO:4:

( i ) SEQUENCE CHARACTERISTICS:
        ( A ) LENGTH: 838 amino acids
        ( B ) TYPE: amino acid
        ( C ) STRANDEDNESS: both
        ( D ) TOPOLOGY: linear ( x i ) SEQUENCE DESCRIPTION: SEQ ID NO:4:

```
Met Gly Asn Gly Leu Trp Phe Val Gly Val Ile Ile Leu Gly Val Ala
1               5                   10                  15

Trp Gly Gln Val His Asp Trp Thr Glu Gln Thr Asp Pro Trp Phe Leu
            20                  25                  30

Asp Gly Leu Gly Met Asp Arg Met Tyr Trp Arg Asp Thr Asn Thr Gly
            35                  40                  45

Arg Leu Trp Leu Pro Asn Thr Pro Asp Pro Gln Lys Pro Pro Arg Gly
        50                  55                  60

Phe Leu Ala Pro Pro Asp Glu Leu Asn Leu Thr Thr Ala Ser Leu Pro
65                  70                  75                  80

Leu Leu Arg Trp Tyr Glu Glu Arg Phe Cys Phe Val Leu Val Thr Thr
                85                  90                  95

Ala Glu Phe Pro Arg Asp Pro Gly Gln Leu Leu Tyr Ile Pro Lys Thr
                100                 105                 110

Tyr Leu Leu Gly Arg Pro Pro Asn Ala Ser Leu Pro Ala Pro Thr Thr
            115                 120                 125

Val Glu Pro Thr Ala Gln Pro Pro Ser Val Ala Pro Leu Lys Gly
            130                 135                 140

Leu Leu His Asn Pro Ala Ser Val Leu Leu Arg Ser Arg Ala Trp
145                 150                 155                 160

Val Thr Phe Ser Ala Val Pro Asp Pro Glu Ala Leu Thr Phe Pro Arg
                165                 170                 175

Gly Asp Asn Val Ala Thr Ala Ser His Pro Ser Gly Pro Arg Asp Thr
            180                 185                 190

Pro Pro Pro Arg Pro Pro Val Gly Ala Arg Arg His Pro Thr Thr Glu
            195                 200                 205

Leu Asp Ile Thr His Leu His Asn Ala Ser Thr Thr Trp Leu Ala Thr
    210                 215                 220

Arg Gly Leu Leu Arg Ser Pro Gly Arg Tyr Val Tyr Phe Ser Pro Ser
225                 230                 235                 240

Ala Ser Thr Trp Pro Val Gly Ile Trp Thr Thr Gly Glu Leu Val Leu
                245                 250                 255

Gly Cys Asp Ala Ala Leu Val Arg Ala Arg Tyr Gly Arg Glu Phe Met
            260                 265                 270

Gly Leu Val Ile Ser Met His Asp Ser Pro Val Glu Val Met Val
        275                 280                 285

Val Pro Ala Gly Gln Thr Leu Asp Arg Val Gly Asp Pro Ala Asp Glu
    290                 295                 300

Asn Pro Pro Gly Ala Leu Pro Gly Pro Pro Gly Gly Pro Arg Tyr Arg
305                 310                 315                 320

Val Phe Val Leu Gly Ser Leu Thr Arg Ala Asp Asn Gly Ser Ala Leu
            325                 330                 335

Asp Ala Leu Arg Arg Val Gly Gly Tyr Pro Glu Glu Gly Thr Asn Tyr
            340                 345                 350

Ala Gln Phe Leu Ser Arg Ala Tyr Ala Glu Phe Phe Ser Gly Asp Ala
        355                 360                 365

Gly Ala Glu Gln Gly Pro Arg Pro Pro Leu Phe Trp Arg Leu Thr Gly
        370                 375                 380

Leu Leu Ala Thr Ser Gly Phe Ala Phe Val Asn Ala Ala His Ala Asn
385                 390                 395                 400

Gly Ala Val Cys Leu Ser Asp Leu Leu Gly Phe Leu Ala His Ser Arg
            405                 410                 415

Ala Leu Ala Gly Leu Ala Ala Arg Gly Ala Ala Gly Cys Ala Ala Asp
            420                 425                 430
```

```
Ser Val Phe Phe Asn Val Ser Val Leu Asp Pro Thr Ala Arg Leu Gln
        435                 440                 445
Leu Glu Ala Arg Leu Gln His Leu Val Ala Glu Ile Leu Glu Arg Glu
450                 455                 460
Gln Ser Leu Ala Leu His Ala Leu Gly Tyr Gln Leu Ala Phe Val Leu
465                 470                 475                 480
Asp Ser Pro Ser Ala Tyr Asp Ala Val Ala Pro Ser Ala Ala His Leu
                485                 490                 495
Ile Asp Ala Leu Tyr Ala Glu Phe Leu Gly Gly Arg Val Leu Thr Thr
            500                 505                 510
Pro Val Val His Arg Ala Leu Phe Tyr Ala Ser Ala Val Leu Arg Gln
            515                 520                 525
Pro Phe Leu Ala Gly Val Pro Ser Ala Val Gln Arg Glu Arg Ala Arg
        530                 535                 540
 Arg Ser Leu Leu Ile Ala Ser Ala Leu Cys Thr Ser Asp Val Ala Ala
545                 550                 555                 560
Ala Thr Asn Ala Asp Leu Arg Thr Ala Leu Ala Arg Ala Asp His Gln
                565                 570                 575
Lys Thr Leu Phe Trp Leu Pro Asp His Phe Ser Pro Cys Ala Ala Ser
            580                 585                 590
Leu Arg Phe Asp Leu Asp Glu Ser Val Phe Ile Leu Asp Ala Leu Ala
        595                 600                 605
Gln Ala Thr Arg Ser Glu Thr Pro Val Glu Val Leu Ala Gln Gln Thr
610                 615                 620
His Gly Leu Ala Ser Thr Leu Thr Arg Trp Ala His Tyr Asn Ala Leu
625                 630                 635                 640
Ile Arg Ala Phe Val Pro Glu Ala Ser His Arg Cys Gly Gly Gln Ser
                645                 650                 655
Ala Asn Val Glu Pro Arg Ile Leu Val Pro Ile Thr His Asn Ala Ser
            660                 665                 670
Tyr Val Val Thr His Ser Pro Leu Pro Arg Gly Ile Gly Tyr Lys Leu
        675                 680                 685
Thr Gly Val Asp Val Arg Arg Pro Leu Phe Leu Thr Tyr Leu Thr Ala
    690                 695                 700
Thr Cys Glu Gly Ser Thr Arg Asp Ile Glu Ser Lys Arg Leu Val Arg
705                 710                 715                 720
Thr Gln Asn Gln Arg Asp Leu Gly Leu Val Gly Ala Val Phe Met Arg
                725                 730                 735
Tyr Thr Pro Ala Gly Glu Val Met Ser Val Leu Val Asp Thr Asp
            740                 745                 750
Asn Thr Gln Gln Gln Ile Ala Ala Gly Pro Thr Glu Gly Ala Pro Ser
        755                 760                 765
Val Phe Ser Ser Asp Val Pro Ser Thr Ala Leu Leu Leu Phe Pro Asn
    770                 775                 780
Gly Thr Val Ile His Leu Leu Ala Phe Asp Thr Gln Pro Val Ala Ala
785                 790                 795                 800
Ile Ala Pro Gly Phe Leu Ala Ala Ser Ala Leu Gly Val Val Met Ile
                805                 810                 815
Thr Ala Ala Leu Ala Gly Ile Leu Lys Val Leu Arg Thr Ser Val Pro
            820                 825                 830
Phe Phe Trp Arg Arg Glu
        835
```

( 2 ) INFORMATION FOR SEQ ID NO:5:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

TCAGTTAACG CCTCTGTTCC TTTCCCTTC        29

( 2 ) INFORMATION FOR SEQ ID NO:6:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

TCAGAATTCG AGCAGCTCCT CATGTTCGAC        30

( 2 ) INFORMATION FOR SEQ ID NO:7:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:7:

TCAAAGCTTC TGCAGCGCGG CGGGAGGTGG        30

( 2 ) INFORMATION FOR SEQ ID NO:8:

( i ) SEQUENCE CHARACTERISTICS:
        ( A ) LENGTH: 29 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:8:

TCAGTTAACC GTCGTCCGG CTGCCAGTC        29

( 2 ) INFORMATION FOR SEQ ID NO:9:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:9:

TCAGTTAACG GACAGCATGG CCAGGTCAAG        30

( 2 ) INFORMATION FOR SEQ ID NO:10:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:10:

TCGAAGCTTC AGGGAGTGGC GCAGC        25

( 2 ) INFORMATION FOR SEQ ID NO:11:

```
        ( i ) SEQUENCE CHARACTERISTICS:
                ( A ) LENGTH: 29 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:11:

TCAGAATTCG   TTCCGGGAGC   AGGCGTGGA                                                                  29

( 2 ) INFORMATION FOR SEQ ID NO:12:

( i ) SEQUENCE CHARACTERISTICS:
                ( A ) LENGTH: 57 base pairs
                ( B ) TYPE: nucleic acid
                ( C ) STRANDEDNESS: single
                ( D ) TOPOLOGY: linear ( x i ) SEQUENCE DESCRIPTION: SEQ ID NO:12:

TCAGTTAACT   GCACTAGTTT   TAATTAATAC   GTATGCCGTC   CGTCCCGGCT   GCCAGTC                              57
```